(12) United States Patent
Woolf et al.

(10) Patent No.: US 7,906,520 B2
(45) Date of Patent: Mar. 15, 2011

(54) METHODS FOR TREATING PAIN

(75) Inventors: Clifford J. Woolf, Newton, MA (US);
Michael Costigan, Somerville, MA (US); Robert Griffin, Boston, MA (US);
Irmgard Tegeder, Frankfurt (DE)

(73) Assignee: The General Hospital Corporation, Boston, MA (US)

( * ) Notice: Subject to any disclaimer, the term of this patent is extended or adjusted under 35 U.S.C. 154(b) by 1668 days.

(21) Appl. No.: 10/987,289

(22) Filed: Nov. 12, 2004

(65) Prior Publication Data
US 2005/0197341 A1 Sep. 8, 2005

Related U.S. Application Data

(60) Provisional application No. 60/520,536, filed on Nov. 13, 2003.

(51) Int. Cl.
*A61K 31/519* (2006.01)
(52) U.S. Cl. .................. 514/264.1; 514/265.1
(58) Field of Classification Search ............ 514/265.1, 514/264.1
See application file for complete search history.

(56) References Cited

U.S. PATENT DOCUMENTS

| | | | | |
|---|---|---|---|---|
| 3,892,844 | A | * | 7/1975 | Erlemann et al. ........... 424/59 |
| 4,772,606 | A | * | 9/1988 | Sircar et al. ............ 514/263.22 |
| 5,449,688 | A | | 9/1995 | Wahl et al. |
| 5,698,408 | A | | 12/1997 | Rokos |
| 5,874,433 | A | | 2/1999 | Gross |
| 5,877,176 | A | | 3/1999 | Gross |
| 6,274,581 | B1 | | 8/2001 | Gross |
| 6,346,519 | B1 | | 2/2002 | Petrus |
| 6,410,729 | B1 | | 6/2002 | Spohr et al. |
| 6,451,788 | B1 | | 9/2002 | Horrobin et al. |
| 6,593,331 | B2 | | 7/2003 | Camborde et al. |
| 2001/0011146 | A1 | | 8/2001 | Joh et al. |
| 2003/0124174 | A1 | | 7/2003 | Galer |
| 2003/0133951 | A1 | | 7/2003 | Coe et al. |

FOREIGN PATENT DOCUMENTS

| | | |
|---|---|---|
| WO | WO 95/13803 | 5/1995 |
| WO | WO 98/35055 | 8/1998 |
| WO | WO 00/33830 | 6/2000 |
| WO | WO 00/37653 | 6/2000 |
| WO | WO 02/04452 | 1/2002 |

OTHER PUBLICATIONS

Niedbala et al., "Nitric oxide mediates neuropathic pain behavior in peripherally denervated rats," Neurosci Lett. 188:57-60, 1995.

(Continued)

*Primary Examiner* — San-ming Hui
(74) *Attorney, Agent, or Firm* — Clark & Elbing LLP

(57) ABSTRACT

The present invention features methods and compositions for preventing, reducing, or treating a traumatic, metabolic or toxic peripheral nerve lesion or pain including, for example, neuropathic pain, inflammatory and nociceptive pain by administering to a mammal in need thereof a compound that reduces the expression or activity of BH4. According to this invention, this reduction may be achieved by reducing the enzyme activity of any of the BH4 synthetic enzymes, such as GTP cyclohydrolase (GTPCH), sepiapterin reductase (SPR), or dihydropteridine reductase (DHPR); by antagonizing the cofactor function of BH4 on BH4-dependent enzymes; or by blocking BH4 binding to membrane bound receptors. The compounds of the invention may be administered alone or in combination with a second therapeutic agent.

39 Claims, 32 Drawing Sheets

OTHER PUBLICATIONS

Psarakis et al., "Analgesia induced by N-acetylserotonin in the central nervous system," Life Sci. 42:1109-16, 1988.

Yamamoto et al., "Inhibitory effect of 8-azuguanine on the development of tolerance in the analgesic action of morphine," Jpn J Pharmacol. 17:140-2, 1967.

Translation of communication from the Japanese Patent Office in Japanese Patent Application No. 2006-539848 dated Jun. 23, 2010.

Brautigam et al., "Apomorphine does not decrease tissue levels of tetrahydrobiopterin in vivo," Eur J Pharmacol. 127:143-6 (1986).

Ishii et al., "Acceleration of oxidative stress-induced endothelial cell death by nitric oxide synthase dysfunction accompanied with decrease in tetrahydrobiopterin content," Life Sci. 61:739-47 (1997).

Schoedon et al., "Modulation of human endothelial cell tetrahydrobiopterin synthesis by activating and deactivating cytokines: new perspectives on endothelium-derived relaxing factor," Biochem Biophys Res Commun. 196:1343-8 (1993).

Suzuki et al., "Decrease in tetrahydrobiopterin content and neurotransmitter amine biosynthesis in rat brain by an inhibitor of guanosine triphosphate cyclohydrolase," Brain Res. 446:1-10 (1988).

Werner et al., "Identification of the 4-amino analogue of tetrahydrobiopterin as a dihydropteridine reductase inhibitor and a potent pteridine antagonist of rat neuronal nitric oxide synthase," Biochem J. 320:193-6 (1996).

Search Report from European Application No. 04810728.8, mailed May 7, 2010.

Aley et al., "Nitric Oxide Signaling in Pain and Nociceptor Sensitization in the Rat," J Neurosci 18:7008-7014 (1998).

Alhaider et al., "Differential Roles of 5-Hydroxytryptamine$_{1A}$ and 5-Hydroxytryptamine$_{1B}$ Receptor Subtypes in Modulating Spinal Nociceptive Transmission in Mice," J Pharmacol Exp Ther 265:378-385 (1993).

Bader et al., "Crystal Structure of Rat GTP Cyclohydrolase I Feedback Regulatory Protein, GFRP," J Mol Biol 312:1051-1057 (2001).

Bennett, G.J., "An Animal Model of Neuropathic Pain: A Review," Muscle Nerve 16:1040-1048 (1993).

Blau et al., "Antenatal Diagnosis of Tetrahydrobiopterin Deficiency by Quantification of Pterins in Amniotic Fluid and Enzyme Activity in Fetal and Extrafetal Tissue," Clin Chim Acta 226:159-169 (1994).

Bodnar et al., "Reductions in Pain Thresholds and Morphine Analgesia Following Intracerebroventricular Parachlorophenylalanine," Pharmacol Biochem Behav 21:79-84 (1984).

Bräutigam et al., "Determination of Reduced Biopterins by High Pressure Liquid Chromatography and Subsequent Electrochemical Detection," Hoppe Seylers Z Physiol Chem 363:341-343 (1982).

Costigan et al., "Replicate High-Density Rat Genome Oligonucleotide Microarrays Reveal Hundreds of Regulated Genes in the Dorsal Root Ganglion After Peripheral Nerve Injury," BMC Neuroscience 3:16 (2002).

Curtius et al., "Tetrahydrobiopterin Biosynthesis. Studies with Specifically Labeled ($^2$H)NAD(P)H and $^2$H$_2$O and of the Enzymes Involved," Eur J Biochem 148:413-419 (1985).

Decosterd et al., "Spared Nerve Injury: An Animal Model of Persistent Peripheral Neuropathic Pain," Pain 87:149-158 (2000).

Duch et al., "Endocrine-Dependent Regulation of Tetrahydrobiopterin Levels and Guanosine Triphosphate Cyclohydrolase Activity," Mol Cell Endocrinol 47:209-216 (1986).

Fauci et al., Harrison's Online: Chapter 12: Pain: Pathophysiology and Management, 2003.

Fukushima et al., "Analysis of Reduced Forms of Biopterin in Biological Tissues and Fluids," Anal Biochem 102:176-188 (1980).

Fukushima et al., "Chromatographic Analysis of Pteridines," Methods Enzymol 66:429-436 (1980).

Geller et al., "GTP Cyclohydrolase I Is Coinduced in Hepatocytes Stimulated to Produce Nitric Oxide," Biochem Biophys Res Commun 276:633-641 (2000).

Giannini et al., "Methotrexate in Resistant Juvenile Rheumatoid Arthritis. Results of the U.S.A.-U.S.S.R. Double-Blind, Placebo-Controlled Trial," N Engl J Med 326:1043-1049 (1992).

Gühring et al., "Suppressed Injury-Induced Rise in Spinal Prostaglandin E$_2$ Production and Reduced Early Thermal Hyperalgesia in iNOS-Deficient Mice," J Neurosci 20:6714-6720 (2000).

Handy et al., "Effects of Selective Inhibitors of Neuronal Nitric Oxide Synthase on Carrageenan-Induced Mechanical and Thermal Hyperalgesia," Neuropharmacology 37:37-43 (1998).

Hao et al., "Treatment of a Chronic Allodynia-Like Response in Spinally Injured Rats: Effects of Systemically Administered Nitric Oxide Synthase Inhibitors," Pain 66:313-319 (1996).

Harada et al., "Feedback Regulation Mechanisms for the Control of GTP Cyclohydrolase I Activity," Science 260:1507-1510 (1993).

Hattori, "Diseases and Pathophysiology Arising from Biopterin Dysregulation," J Med Sci 22:95-100 (2002).

Hoffmeister, R.T., "Methotrexate Therapy in Rheumatoid Arthritis: 15 Years Experience," Am J Med 75:69-73 (1983).

Huisman et al., "Anti-Inflammatory Effects of Tetrahydrobiopterin on Early Rejection in Renal Allografts: Modulation of Inducible Nitric Oxide Synthase," FASEB J 16:1135-1137 (2002).

Kaneko et al., "Determination of Tetrahydrobiopterin in Murine Locus Coeruleus by HPLC with Fluorescence Detection," Brain Res Brain Res Protoc 8:25-31 (2001).

Kapatos et al., "GTP Cyclohydrolase I Feedback Regulatory Protein Is Expressed in Serotonin Neurons and Regulates Tetrahydrobiopterin Biosynthesis," J Neurochem 72:669-675 (1999).

Kim et al., "An Experimental Model for Peripheral Neuropathy Produced by Segmental Spinal Nerve Ligation in the Rat," Pain 50:355-363 (1992).

Kolinsky et al., "The Mechanism of Potent GTP Cyclohydrolase I Inhibition by 2,4-Diamino-6-Hydroxypyrimidine. Requirement of the GTP Cyclohydrolase I Feedback Regulatory Protein," J Biol Chem 279:40677-40682 (2004).

Koshimura et al., "Characterization of a Dopamine-Releasing Action of 6R-L-erythro-Tetrahydrobiopterin: Comparison with a 6S-Form," J Neurochem 65:827-830 (1995).

Lawand et al., "Blockade of Joint Inflammation and Secondary Hyperalgesia by L-NAME, a Nitric Oxide Synthase Inhibitor," Neuroreport 8:895-899 (1997).

Levy et al., "Local Nitric Oxide Synthase Activity in a Model of Neuropathic Pain," Eur J Neurosci 10:1846-1855 (1998).

Levy et al., "Transient Action of the Endothelial Constitutive Nitric Oxide Synthase (ecNOS) Mediates the Development of Thermal Hypersensitivity Following Peripheral Nerve Injury," Eur J Neurosci 12:2323-2332 (2000).

Lindqvist et al., "Neuropeptide- and Tyrosine Hydroxylase-Immunoreactive Nerve Fibers in Painful Morton's Neuromas," Muscle Nerve 23:1214-1218 (2000).

Ma et al., "Chronic Constriction Injury of Sciatic Nerve Induces the Up-Regulation of Descending Inhibitory Noradrenergic Innervation to the Lumbar Dorsal Horn of Mice," Brain Res 970:110-118 (2003).

Ma et al., "Partial Sciatic Nerve Transection Induced Tyrosine Hydroxidase Immunoreactive Axon Sprouting around Both Injured and Spared Dorsal Root Ganglion Neurons Which Project to the Gracile Nucleus in Middle-Aged Rats," Neurosci Lett 275:117-120 (1999).

Maita et al., "Crystal Structure of the Stimulatory Complex of GTP Cyclohydrolase I and Its Feedback Regulatory Protein GFRP," Proc Natl Aced Sci USA 99:1212-1217 (2002).

Mataga et al., "6R-Tetrahydrobiopterin Perfusion Enhances Dopamine, Serotonin, and Glutamate Outputs in Dialysate from Rat Striatum and Frontal Cortex," Brain Res 551:64-71 (1991).

McCleane, G., "The Pharmacological Management of Neuropathic Pain: A Review," online Publication [www.priory.com/anaes/neuropathic.htm], 2003.

Meller et al., "Nitric Oxide Mediates the Thermal Hyperalgesia Produced in a Model of Neuropathic Pain in the Rat," Neuroscience 50:7-10 (1992).

Minami et al., "L-NAME, an Inhibitor of Nitric Oxide Synthase, Blocks the Established Allodynia Induced by Intrathecal Administration of Postaglandin E$_2$," Neurosci Lett 201:239-242 (1995).

Moali et al., "Oxidations of N$^\omega$-Hydroxyarginine Analogues and Various N-Hydroxyguanidines by NO Synthase II: Key Role of Tetrahydrobiopterin in the Reaction Mechanism and Substrate Selectivity," *Chem Res Toxicol* 14:202-210 (2001).

Nagatsu et al., "Radioimmunoassay for Biopterin in Body Fluids and Tissues," *Anal Biochem* 110:182-189 (1981).

Ochi et al., "FR143166 Attenuates Spinal Pain Transmission Through Activation of the Serotonergic System," *Eur J Pharmacol* 452:319-324 (2002).

Ohue et al., "A Novel Action of 6*R*-L-*erythro*-5,6,7,8-tetrahydrobiopterin, a Cofactor for Hydroxylases of Phenylalanine, Tyrosine and Tryptophan: Enhancement of Acetylcholine Release in Vivo in the Rat Hippocampus," *Neurosci Lett* 128:93-96 (1991).

O'Neil et al., "RNA-Mediated Interference as a Tool for Identifying Drug Targets," *Am J Pharmacogenomics* 1:45-53 (2001).

Ota et al., "Tetrahydrobiopterin Biosynthesis Enhanced by Lipopolysaccharide Stimulation in Murine Neuroblastoma Cell Line N1E-115," *J Neurochem* 67:2540-2548 (1996).

Ponzone et al., "Combined Phenylalanine-Tetrahydrobiopterin Loading Test in GTP Cyclohydrolase 1 Deficiency," *Eur J Pediatr* 153:616 (1994).

Powers et al., "Estimation of Tetrahydrobiopterin and Other Pterins in Plasma by Isocratic Liquid Chromatography with Electrochemical and Fluorimetric Detection," *J Chromatogr* 432:321-328 (1988).

Psarakis et al., "Analgesia Induced by N-Acetylserotonin in the Central Nervous System," *Life Sci* 42:1109-1116 (1988).

Rebelo et al., "Biosynthesis of Pteridines. Reaction Mechanism of GTP Cyclohydrolase I," *J Mol Biol* 326:503-516 (2003).

Rebrin et al., "Catalytic Characterization of 4a-Hydroxytetrahydropterin Dehydratase," *Biochemistry* 34:5801-5810 (1995).

Renodon-Cornière et al., "Efficient Formation of Nitric Oxide from Selective Oxidation of *N*-Aryl *N'*-Hydroxyguanidines by Inducible Nitric Oxide Synthase," *Biochemistry* 38:4663-4668 (1999).

Roche et al., "A Nitric Oxide Synthesis Inhibitor (L-NAME) Reduces Licking Behavior and Fos-labeling in the Spinal Cord of Rats during Formalin-Induced Inflammation," *Pain* 66:331-341 (1996).

Seltzer et al., "A Novel Behavioral Model of Neuropathic Pain Disorders Produced in Rats by Partial Sciatic Nerve Injury," *Pain* 43:205-218 (1990).

Shiraki et al., "Stimulating Effect of 6*R*-Tetrahydrobiopterin on $CA^{2+}$ Channels in Neurons of Rat Dorsal Motor Nucleus of the Vagus," *Biochem Biophys Res Commun* 221:181-185 (1996).

Smith et al., "New Inhibitors of Sepiapterin Reductase. Lack of an Effect of Intracellular Tetrahydrobiopterin Depletion upon in Vitro Proliferation of Two Human Cell Lines," *J Biol Chem* 267:5599-5607 (1992).

Stea et al., "Separation of Unconjugated Pteridines by High-Pressure Cation-Exchange Liquid Chromatography," *J Chromatogr* 168:385-393 (1979).

Stein et al., "Unilateral Inflammation of the Hindpaw in Rats as a Model of Prolonged Noxious Stimulation: Alterations in Behavior and Nociceptive Thresholds," *Pharmacol Biochem Behav* 31:445-451 (1988).

Tegeder et al., "Dual Effects of Spinally Delivered 8-Bromo-Cyclic Guanosine Mono-Phosphate (8-bromo-cGMP) in Formalin-Induced Nociception in Rats," *Neurosci Lett* 332:146-150 (2002).

Thöny et al., "Tetrahydrobiopterin Biosynthesis, Regeneration and Functions," *Biochem J* 347:1-16 (2000).

Viveros et al., "Biopterin Cofactor Biosynthesis: Independent Regulation of GTP Cyclohydrolase in Adrenal Medulla and Cortex," *Science* 213:349-350 (1981).

Watson, "Some Responses of Neurones of Dorsal Root Ganglia to Axotomy," *J Physiol* 231:41P-42P (1973).

Weinblatt et al., "Efficacy of Low-Dose Methotrexate in Rheumatoid Arthritis," *N Engl J Med* 312:818-822 (1985).

Weinstein et al., "Low-Dose Methotrexate Treatment of Rheumatoid Arthritis. Long-Term Observations," *Am J Med* 79:331-337 (1985).

Werner et al., "Determination of Tetrahydrobiopterin Biosynthetic Activities by High-Performance Liquid Chromatography with Fluorescence Detection," *Methods Enzymol.* 281:53-61 (1997).

Werner et al., "High-Performance Liquid Chromatographic Methods for the Quantification of Tetrahydrobiopterin Biosynthetic Enzymes," *J Chromatogr B Biomed Appl* 684:51-58 (1996).

Werner et al., "Synthesis and Characterization of $^3$H-Labelled Tetrahydrobiopterin," *Biochem J* 304:189-193 (1994).

Werner-Felmayer et al., "Tetrahydrobiopterin Biosynthesis, Utilization and Pharmacological Effects," *Curr Drug Metab* 3:159-173 (2002).

Williams et al., "Comparison of Low-Dose Oral Pulse Methotrexate and Placebo in the Treatment of Rheumatoid Arthritis. A Controlled Clinical Trial," *Arthritis Rheum* 28:721-730 (1985).

Woolf et al., "Nerve Growth Factor Contributes to the Generation of Inflammatory Sensory Hypersensitivity," *Neuroscience* 62:327-331 (1994).

Xie et al., "GTP Cyclohydrolase I Inhibition by the Prototypic Inhibitor 2,4-Diamino-6-Hydroxypyrimidine. Mechanisms and Unanticipated Role of GTP Cyclohydrolase I Feedback Regulatory Protein," *J Biol Chem* 273:21091-21098 (1998).

Yamaguchi et al., "Antinociceptive Synergistic Interaction between Morphine and $n^\omega$-Nitro L-Arginine Methyl Ester on Thermal Nociceptive Tests in the Rats," *Can J Anaesth* 43:975-981 (1996).

Yoneyama et al., "Decameric GTP Cyclohydrolase I Forms Complexes with Two Pentameric GTP Cyclohydrolase I Feedback Regulatory Proteins in the Presence of Phenylalanine or of a Combination of Tetrahydrobiopterin and GTP," *J Biol Chem* 273:20102-20108 (1998).

Yoneyama et al., "Ligand Binding to the Inhibitory and Stimulatory GTP Cyclohydrolase I/GTP Cyclohydrolase I Feedback Regulatory Protein Complexes," *Protein Sci* 10:871-878 (2001).

Yoneyama et al., "GTP Cyclohydrolase I Feedback Regulatory Protein-Dependent and -Independent Inhibitors of GTP Cyclohydrolase I," *Arch Biochem Biophys* 388:67-73 (2001).

Zorzi et al., "Detection of Sepiapterin in CSF of Patients with Sepiapterin Reductase Deficiency," *Mol Genet Metab* 75:174-177 (2002).

International Search Report mailed Aug. 31, 2006 (PCT/US04/37621).

\* cited by examiner

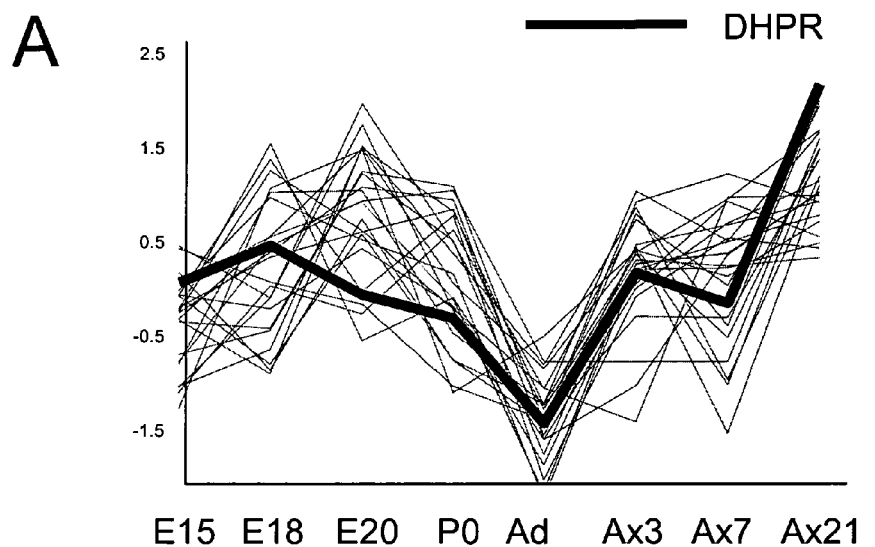
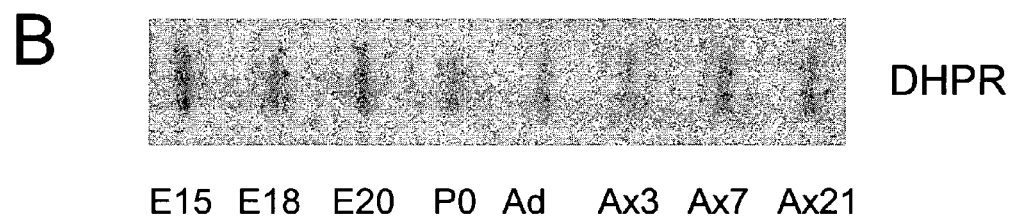
Figure 1

Catabolism of Tetrahydrobiopterin source: http://www.bh4.org/

FIGURE 3

|  | Naïve Signal | 3d Axotomy Signal | Fold | P value |
|---|---|---|---|---|
| GTP cyclohydrolase | 222 ± 12 | 1605 ± 94 | 7.2 | 0.006 |
| Sepiapterin reductase | 2475 ± 697 | 5043 ± 570 | 2.0 | 0.009 |
| Dihydropteridine Reductase | 4568 ± 320 | 5510 ± 384 | 1.2 | 0.03 |

DRG

DH

DRG-CFA

DH-CFA

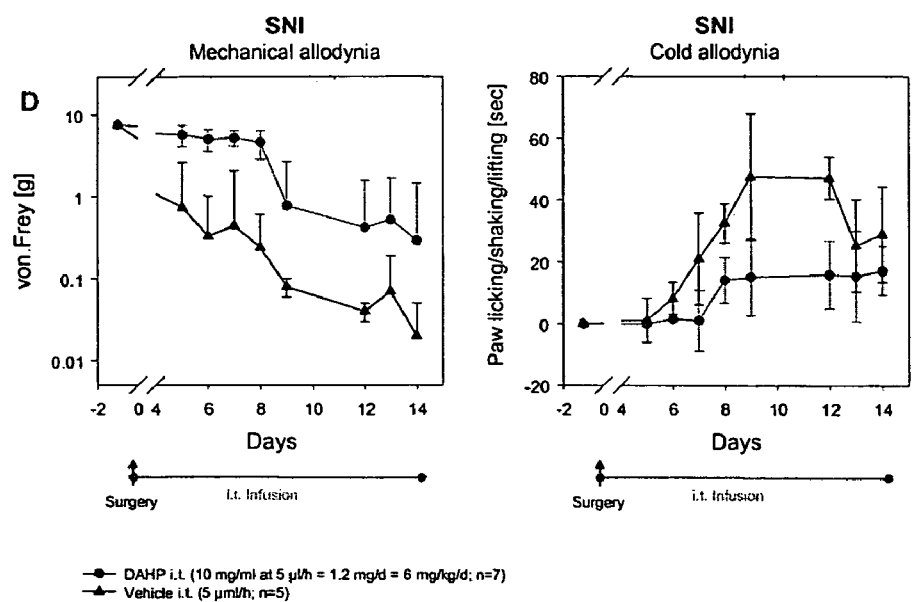
(Figure 8 ctd)

Figure 17

*Sepiapterin Reductase Inhibitors*

TABLE I
*Sepiapterin reductase inhibitors*

Assays were performed using bovine adrenal medullary sepiapterin reductase as described in the text. $K_i$ and $\alpha K_i$ are defined as previously described (33), where $K_i$ = the dissociation constant for EI and $\alpha K_i$ = the constant for the dissociation of I from ESI (E = enzyme, I = inhibitor, S = substrate). Inhibition patterns were analyzed for best fit to competitive, noncompetitive, or uncompetitive inhibition.

| Class | Compound no. | Structure | | | | | $\alpha K_i^*$ | $K_i$ |
|---|---|---|---|---|---|---|---|---|
| | | | | | | | $\mu M$ | |
| | | R | $R^1$ | $R^2$ | | | | |
| | 1 | HO | H | Me | | | | 0.12 |
| | 2 | H | H | Me | | | | 10 |
| | 3 | MeO | H | Me | | | | 30 |
| | 4 | HO | $CO_2H$ | Me | | | | >100 |
| | 5 | HO | H | $CH_2Cl$ | | | | 0.006 |
| | 6 | HO | H | $CH_2OMe$ | | | | 0.008 |
| | | R | $R^1$ | $R^2$ | $R^3$ | $R^4$ | | |
| | 7 | HO | HO | H | H | Me | | 0.4 |
| | 8 | HO | HO | H | H | -COMe | | 0.66 |
| | 9 | HO | HO | H | H | -CH(OH)Me | | 0.62 |
| | 10 | HO | HO | H | H | $-CH_2Cl$ | | 0.014 |
| | 11 | HO | HO | HO | H | Me | | 26 |
| | 12 | HO | HO | HO | Me | Me | | >100 |
| | 13 | H | HO | H | H | Me | | 0.13 |
| | 14 | HO | H | H | H | Me | | >100 |
| | 15 | H | H | H | H | Me | | >100 |
| | | R | $R^1$ | $R^2$ | | | | |
| | 16 | H | H | HO | | | 0.7 | 1 |
| | 17 | HO | HO | H | | | 27 | 16 |
| | 18 | | | | | | 350 | 20 |
| | | X | Y | | | | | |
| | 19 | $CH_2$ | NH | | | | 77 | 49 |
| | 20 | $CH_2$ | $CH_2$ | | | | 59 | 6 |
| | 21 | CH | CH | | | | 83 | 12 |

*Compounds for which $\alpha K_i$ is reported were found to best fit the noncompetitive inhibition model. All other compounds for which absolute $K_i$ values are reported were found to be strictly competitive with the substrate sepiapterin. In these cases, $\alpha$ would be infinite. Mixed inhibition is indicated for $\alpha$ greater than 1 and less than $\infty$.

(Smith GK et al. J Biol Chem 267(8)5599-5607)

Figure 19   Page 1 of 2

Potential GTPCH-I inhibitors (based on Yoneyama T et al., Arch Biochem Biophys. 2001 Apr 1;388(1):67-73

| Compound | Structure | IC50 [µM] | GFRP-dependence |
|---|---|---|---|
| 2,4-diamino-6-hydroxy-pyrimidine (syn. 2,6-diamino-4(1H)-pyrimidinone) (DAHP) $C_4H_6N_4O$ Molecular Weight: 126 | 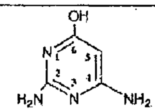 | 100-200 | yes |
| 2,4,5-triamino-6-hydroxy-pyrimidine $C_4H_8N_5O$ Molecular Weight: 142 | 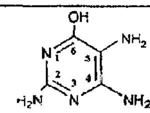 | 150-250 | yes |
| 2-amino-4-hydroxy-6-methylpyrimidine (syn. 6-Methylisocytosine) $C_5H_7N_3O$ Molecular Weight: 125 | 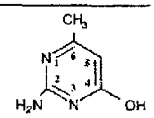 | no inhibition | |
| 4-amino-6-hydroxy-2-mercaptopyrimidine (syn. 6-Amino-2-thiouracil monohydrate) $C_4H_5N_3SO$ Molecular weight: 143 | 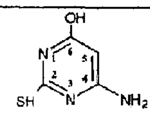 | no inhibition | |
| 2,4-diamino-6-mercaptopyrimidine $C_4H_6N_4S$ Molecular weight: 142 | 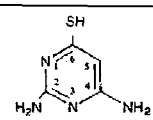 | no inhibition | |
| Guanine (syn. 2-Amino-6-hydroxypurine) $C_5H_5N_5O$ Molecular Weight: 151 | 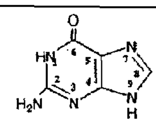 | 20-30 | yes |
| 6-Thioguanine (syn. 2-Amino-6-mercaptopurine) $C_5H_5N_5S$ Molecular Weight: 167 | 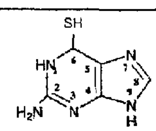 | no inhibition | |
| 1-Methylguanine (syn. 2-Amino-6-hydroxy-1-methylpurine) $C_6H_7N_5O$ Molecular Weight: 165 | 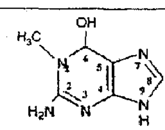 | no inhibition | |
| 8-Bromoguanine $C_5H_4BrN_5O$ Molecular Weight: 230 | 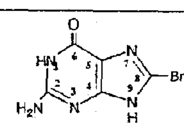 | 25-35 | yes |

FIGURE 19 Page 2 of 2

| | | | |
|---|---|---|---|
| 8-Hydroxyguanine<br>C₅H₆N₅O₂<br>Molecular Weight: 168 | (structure) | 15-20 | yes |
| 8-Methylguanine<br>C₆H₇N₅O<br>(7-Methylguanine, 9-Methylguanine)<br>Molecular Weight: 165 | (structure) | 30-45 | yes |
| 8-Mercaptoguanine<br>C₅H₆N₅SO<br>Molecular Weight: 184 | (structure) | 20-30 | no |
| 8-Azaguanine<br>(syn. 2-Amino-6-hydroxy-8-azapurine, 2-Amino-6-oxy-8-azapurine, Guanazolo)<br>C₄H₄N₆O<br>Molecular Weight: 152 | (structure) | 15-20 | no |
| 8-para-Chlorophenylthio-guanine | (structure) | n.t. | |
| 8-Aminophenylthio-guanine | (structure) | n.t. | |

Figure 20

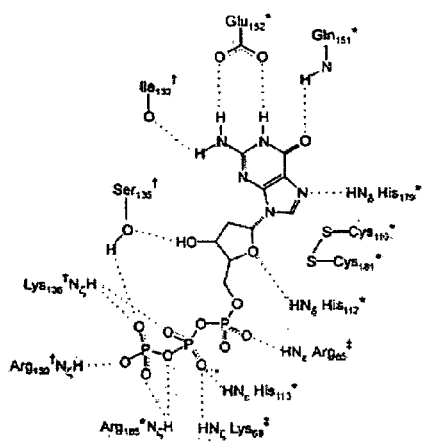

FIG. 5. Schematic representation of the interactions of active site residues with dGTP. Residues are labeled *, †, and ‡ to indicate their origin at three different CYH monomers. All residues involved in dGTP binding are highly conserved, except Lys-68, which is replaced by Ser and Thr in some sequences.

Table 3. Hydrogen bonds

| Guanine base (*GTP) | Protein |
|---|---|
| N1 | ᴬGlu152 O¹ |
| N2 | ᴬGlu152 O² |
|  | *Ile132 O |
| O6 | ᴬGln151N |
| N3 | ᴬLeu134N |
| Ribose (*GTP) |  |
| O2' | *Ser135N |
| O3' | *Ser135 O¹ |
| O5' | *Thr87 O¹ |
| Triphosphate (*GTP) |  |
| O1A | ᴾLys136 Nz |
| O2A | ᵅArg65 NH1 |
| O1G | ᵅArg139 NH1 |
|  | ᴬArg155 NH1 |
| O2G | ᵅArg139 NH1 |
|  | *Ser135 O' |
|  | ᴾLys136 Nz |
| O3G | ᴬArg155 NH2 |
|  | *Ser135 O' |

Hydrogen bonds established between the active site residues and the bound GTP substrate molecule, as observed on the crystallographic structure of the GTP cyclohydrolase I His113Ser mutant. Superscripts mark the molecular subunits.

Interaction of cyclohydrolase with GTP (catalytic center)
Dotted lines indicate hydrogen bonds.
Left: according to Nar H et al., Proc Natl Acad Sci U S A. 1995 Dec 19;92(26):12120-5
Right: according to Rebelo J et al., J Mol Biol. 2003 Feb 14;326(2):503-16

Figure 21

Interaction of cyclohydrolase with GFRP and phenylalanine

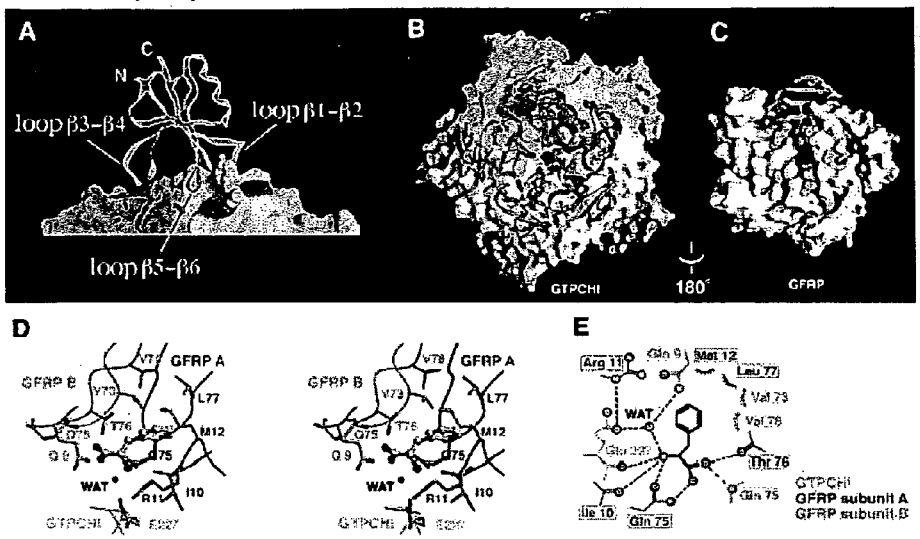

Fig. 5. The phenylalanine-binding sites at the interfaces between GFRP and GTPCHI. (A and B) The contacts between GFRP and GTPCHI are shown with ribbon models of the GFRP subunits and molecular surfaces of GTPCHI. (A) A close-up side view of one GFRP subunit (magenta) that makes contact with two GTPCHI subunits (green and light blue). (B) A top view of the GFRP pentamer on the GTPCHI decamer. In both panels, molecular surfaces colored in blue indicate the GTPCHI residues contacting GFRP. The bound phenylalanine molecules are shown as space-filled models (yellow). The tentative potassium ions are shown as red balls. (C) Five phenylalanine molecules bound to the stimulatory complex are depicted on the molecular surfaces of the GFRP pentamer with one GFRP monomer as a ribbon model (magenta). The bound phenylalanine molecules are shown as space-filled models (yellow). (D) A close-up stereoview of the phenylalanine-binding site located at the interfaces formed by two GFRP subunits (red and pale green) and one GTPCHI subunit (blue). The bound phenylalanine molecule is shown as a ball-and-stick model (yellow). The bridging water molecule is shown as a red ball with the label WAT. (E) Schematic representation of the GFRP- and GTPCHI-phenylalanine interactions. Broken lines indicate hydrogen bonds. The two GFRP subunits are colored in red and pale green, and one GTPCHI subunit is colored in blue. The bound phenylalanine molecule is shown in black lines. The bridging water molecule is labeled WAT.

According to Maita N et al., Proc Natl Acad Sci U S A. 2002 Feb 5;99(3):1212-7

Figure 23
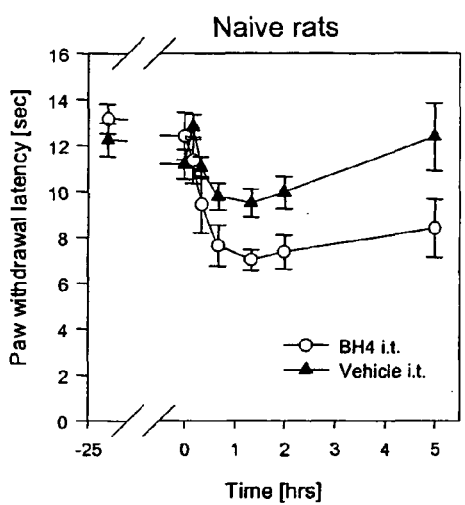
A
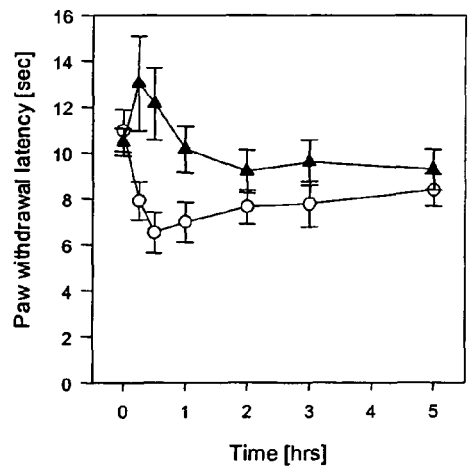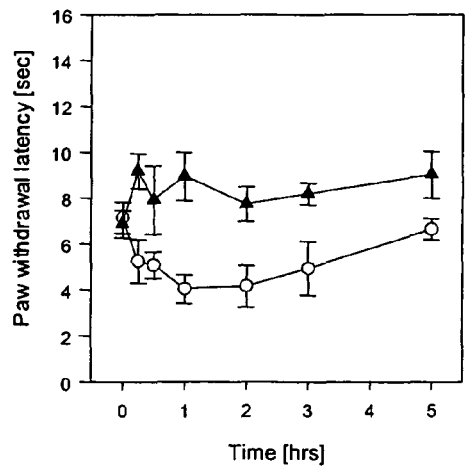
B    Chronic CFA-induced paw inflammation

Figure 24
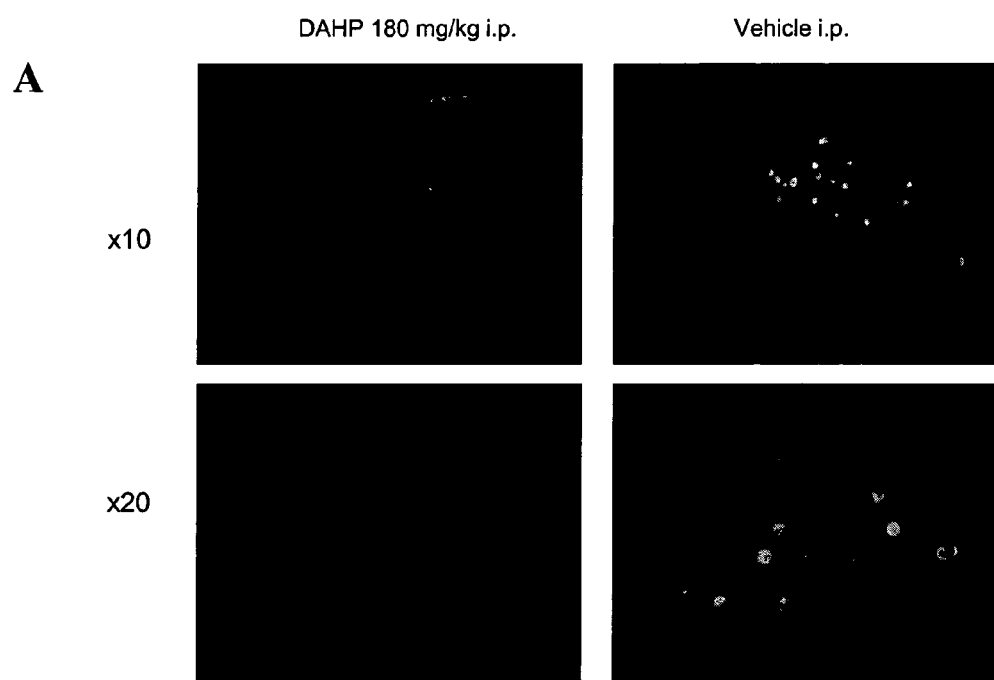
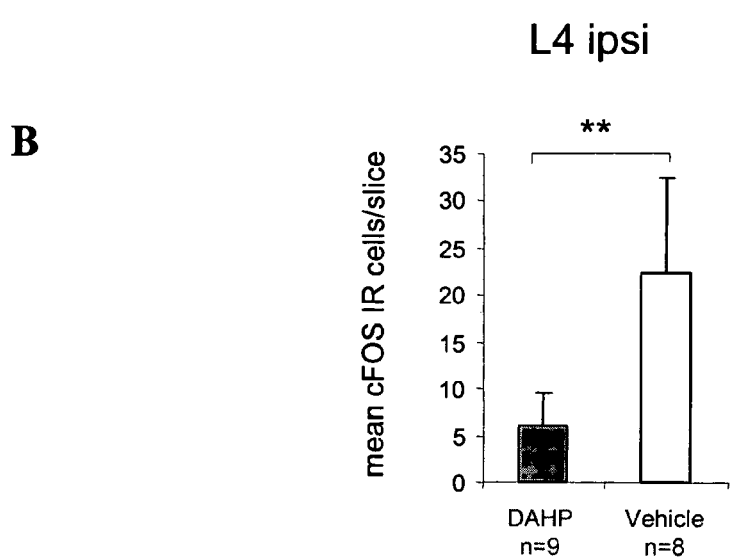

Figure 26
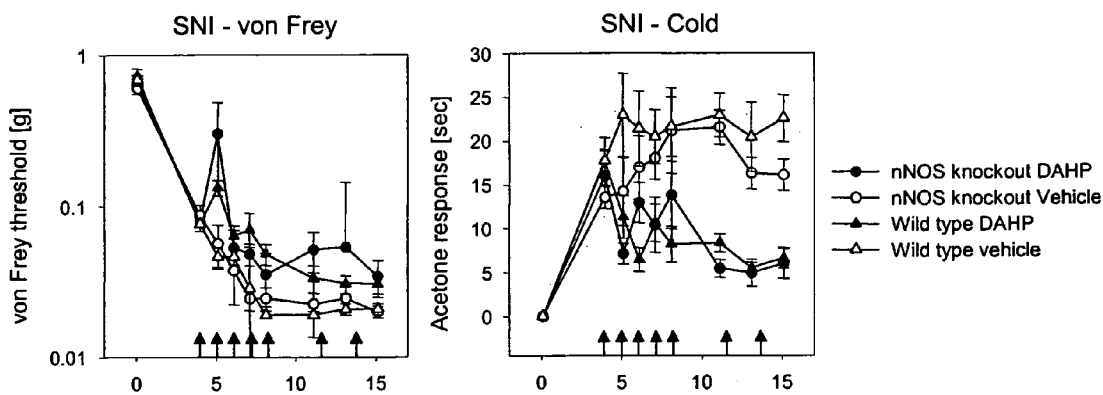
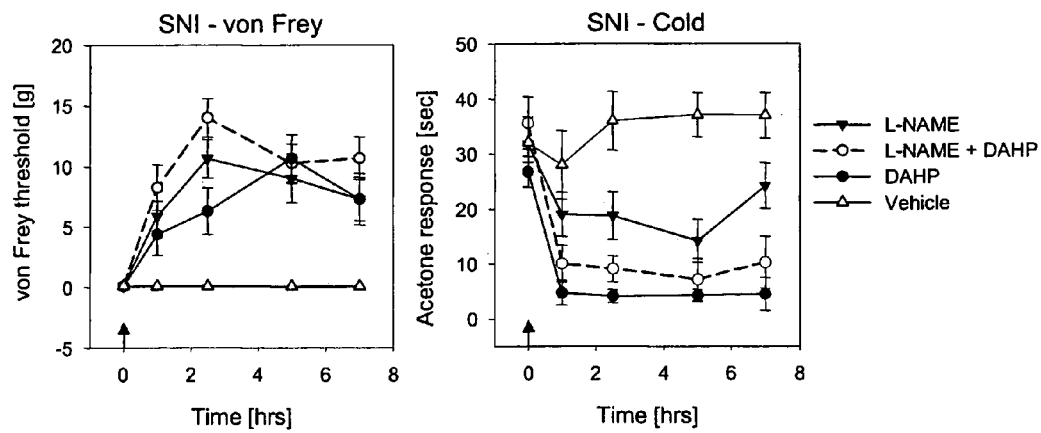

Figure 27
A
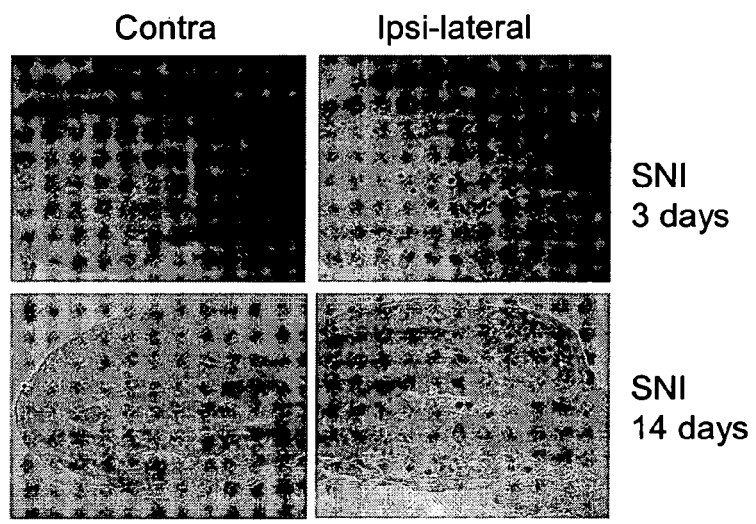
B
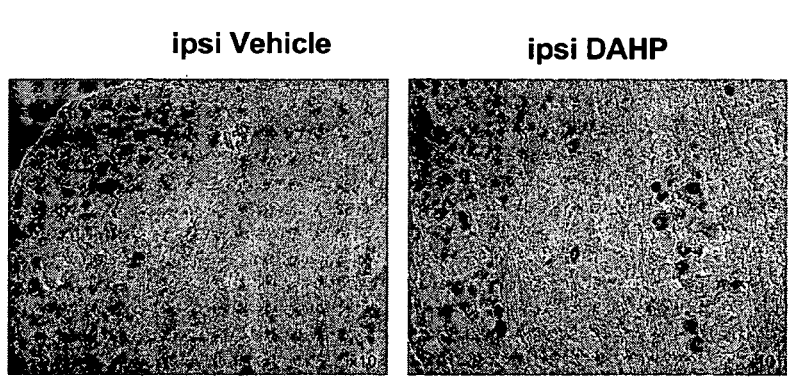

Figure 28
A
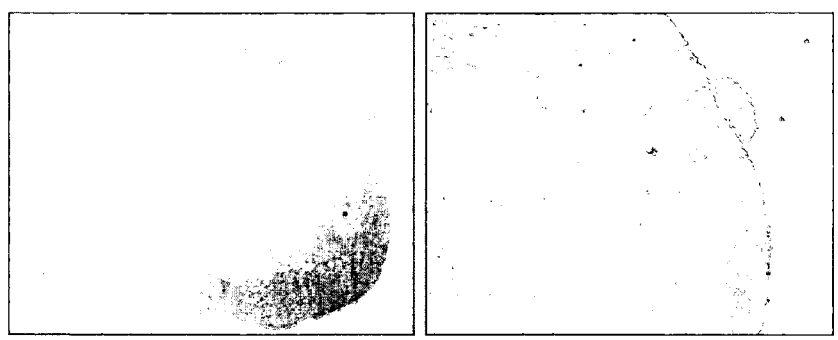
B
 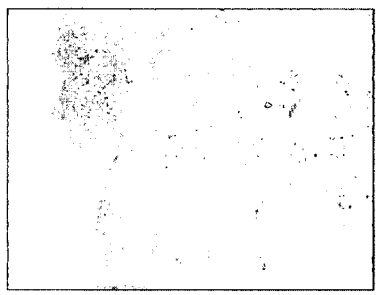

METHODS FOR TREATING PAIN

This application claims benefit of the filing date of the U.S. Provisional Application No. 60/520,536, filed Nov. 13, 2003, hereby incorporated by reference.

FIELD OF THE INVENTION

In general, the invention features methods for diagnosing, treating, reducing, or preventing pain.

BACKGROUND OF THE INVENTION

The sensation of pain is a common symptom that may be indicative of an underlying disease or injury, or the expression of an abnormal function within the nervous system. Pain is often the primary incentive for which treatment is sought.

Pain can take a variety of forms depending on its origin. Pain may be described as being peripheral neuropathic if the initiating injury occurs as a result of a complete or partial transection of a nerve or trauma to a nerve plexus. Alternatively, pain is described as being central neuropathic following a lesion to the central nervous system, such as a spinal cord injury or a cerebrovascular accident. Inflammatory pain is a form of pain that is caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness, associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. Nociceptive pain is the pain experienced in response to a noxious stimulus, such as a needle prick or during trauma or surgery. Functional pain refers to conditions in which there is no obvious peripheral pathology or lesion to the nervous system. This particular form of pain is generated by abnormal function of the nervous system and conditions characterized by such pain include fibromyalgia, tension-type headache, and irritable bowel syndrome. The different types of pain may coexist or pain may be transformed from inflammatory to neuropathic during the natural course of the disease, as in post-herpetic neuralgia.

Although one approach for the treatment of pain is the removal of the causative or etiological agent (disease modifying therapy), the pain often outlasts the duration of the initiating cause. Accordingly, symptomatic control is essential. In cases in which the sensation of pain becomes unbearable, rapid and effective analgesia is imperative (e.g., postoperative state, burns, trauma, cancer, and sickle cell crisis). Currently, there exist a wide variety of analgesic agents useful for the management of pain, including for example non-steroidal analgesic agents (NSAIDs), anticonvulsants, and opioid analgesics. Despite their efficacy, the chronic use of such agents is often not recommended because of the potential debilitating side effects, such as gastric irritation, toxicity to the liver, respiratory depression, sedation, psychotomimetic effects, constipation, nausea, tolerance, dependence, and the risk of abuse. Also, these agents are sometimes suboptimal, particularly for neuropathic and functional pain.

Thus, better therapeutic strategies are required for the treatment and management of pain.

SUMMARY OF THE INVENTION

In general, the present invention features methods for the diagnosis, treatment, reduction, and prevention of pain or of endogenous mechanisms that further increase a traumatic, metabolic or toxic peripheral nerve lesion in a mammal. According to this invention, a mammal (e.g., a human) is administered a composition (e.g., methotrexate) that reduces tetrahydrobiopterin (BH4) biological activity such that pain is reduced, prevented, or treated. Alternatively, pain may be reduced in the mammal being treated by decreasing the levels or activity of any one of the enzymes involved in the synthesis of BH4, i.e. BH4 synthetic enzymes. In this regard, BH4 synthesis may be reduced by decreasing the biological activity of at least one, two, three, or more than three of the following enzymes: sepiapterin reductase (SPR), Pyruvoyltetrahydropterin Synthase (PTPS), GTP cyclohydrolase (GTPCH), Pterin-4α-carbinolamine dehydratase, and dihydropteridine reductase (DHPR). Such activity may be reduced by at least 10%, 20%, 30%, 40%, 50%, 60%, 70%, 80%, 90% 95%, 99%, or even 100% relative to an untreated control. Alternatively, BH4 biological activity may be reduced by increasing the expression or GTPCH-binding or other biological activity of GTP cyclohydrolase feedback regulatory protein (GFRP). GFRP biological activity may be increased by administering a BH4 or phenylalanine analog that specifically binds to GFRP or a GTPCH:GFRP complex. Traumatic nerve lesions include those caused by mechanical insults and compressive injuries. Compressive injuries may be caused by external trauma or injury, or from internal conditions and disease states, such as a compression resulting from an infiltrative tumor. Metabolic nerve lesions amenable to treatment using the methods of this invention include, for example, diabetic peripheral neuropathies, heritable neuropathies, or neuropathies caused by infectious agents such as the human immunodeficiency virus (HIV). Toxic nerve lesions include, for example, those cause by other therapeutic agents (e.g., chemotherapeutics), or chemicals and environmental toxicants (e.g., heavy metals and organic solvents).

According to this invention, a reduction in pain may result, for example, from changes in the function of primary sensory neurons or neurons within the dorsal horn of the spinal cord, in the brainstem, or in the brain. Such changes may result, for example, from a reduction in the synthesis of BH4, leading to a reduction in the activity of various enzymes (e.g., nitric oxide synthase) that utilize BH4 as a cofactor and to a reduction in the activation of membrane-bound BH4-binding receptors following its release from cells. BH4 action on BH4-binding receptors may be inhibited or reduced by means of competitive or non-competitive BH4-like receptor antagonists. BH4 action on enzymes which use BH4 as a cofactor may be inhibited by means of BH4-like competitive antagonists. Such binding or activity may be reduced by at least 10%, 20%, 30%, 40%, 50%, 60%, 70%, 80%, 90% 95%, 99%, or even 100% relative to an untreated control.

Furthermore, levels of tetrahydrobiopterin (BH4), its precursors, or its metabolites may be measured in a biological sample obtained from a mammal (e.g., plasma, tissue sample, cerebrospinal fluid, synovial fluid, or tissue exudates) and, in turn, serve as diagnostic tools and as biomarkers of pain or nerve injury. Methods for measuring BH4 are described, for example, in Powers et al. (1988) *J Chromatogr* 432:321-328; Blau et al. (1994) *Clin Chim Acta* 226:159-169; Ponzone et al. (1994) *Eur J Pediatr* 153:616; Zorzi et al. (2002) *Mol Genet Metab* 75:174-177; and Shiraki et al. (1994) *Eur J Pediatr*

153:616. Optionally, an increase in levels or activities of any one of the BH4 synthetic enzymes may also diagnose pain in a mammal.

The methods of this invention are therefore useful for the diagnosis, treatment, reduction, or prevention of various forms of pain, for example, nociceptive pain, inflammatory pain, functional pain and neuropathic pain, all of which may be acute or chronic. Thus, the mammal being treated may be diagnosed as having peripheral diabetic neuropathy, compression neuropathy, post herpetic neuralgia, trigeminal or glossopharyngeal neuralgia, post traumatic or post surgical nerve damage, lumbar or cervical radiculopathy, AIDS neuropathy, metabolic neuropathy, drug induced neuropathy, complex regional pain syndrome, arachnoiditis, spinal cord injury, bone or joint injury, tissue injury, psoriasis, scleroderma, pruritis, cancer (e.g., prostate, colon, breast, skin, hepatic, or kidney), cardiovascular disease (e.g., myocardial infarction, angina, ischemic or thrombotic cardiovascular disease, peripheral vascular occlusive disease, or peripheral arterial occlusive disease), sickle cell anemia, migraine cluster or tension-type headaches, inflammatory conditions of the skin, muscle, or joints, fibromyalgia, irritable bowel syndrome, non cardiac chest pain, cystitis, pancreatitis, or pelvic pain. Alternatively, the pain for which treatment is being sought may be the result of a traumatic injury, surgery, burn of the cutaneous tissue (caused by a thermal, chemical, or radiation stimulus), or a sunburn.

According to this invention, the mammal being treated may be administered with a composition containing, for example, at least one of the following compounds: methotrexate, trimethoprim-sulfamethoxazole, 2,6 diamino hydroxypyrimidine (DAHP), Tetrahydro-L-biopterin, L-Sepiapterin, 7,8-dihydro-L-Biopterin, 6,7-dimethyltetrahydropterin hydrochloride, 8-bromo-cGMP, N-acetyl-serotonin (NAS), N-Chloroacetylserotonin, N-Methoxyacetylserotonin, and N-Chloroacetyldopamine.

Alternatively, the composition of the invention may contain a compound having the formula:

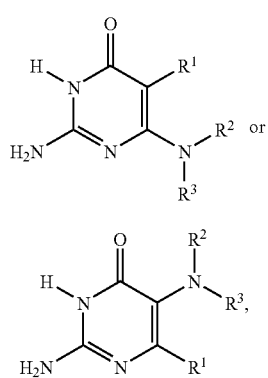

$R^1$ is a H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$. Each of $R^4$ and $R^5$ may be, independently, a H, $C_{1-6}$ alkyl, $C_{6-12}$ aryl, heteroaryl, $C_{1-4}$ alkaryl, or $C_{1-4}$ alkheteroaryl; $R^2$ may be a H, $C_{1-6}$ alkyl, $C_{6-12}$ aryl, heteroaryl, $C_{1-4}$ alkaryl, or $C_{1-4}$ alkheteroaryl; and $R^3$ may be a H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, where $R^6$ is a $C_{1-6}$ alkyl, $C_{6-12}$ aryl, heteroaryl, $C_{1-4}$ alkaryl, or $C_{1-4}$ alkheteroaryl, and each of $R^7$ and $R^8$ is, independently, a H, $C_{1-6}$ alkyl, $C_{6-12}$ aryl, heteroaryl, $C_{1-4}$ alkaryl, or $C_{1-4}$ alkheteroaryl.

Alternatively, $R^3$ may be as above and $R^1$ and $R^2$ together may be represented by

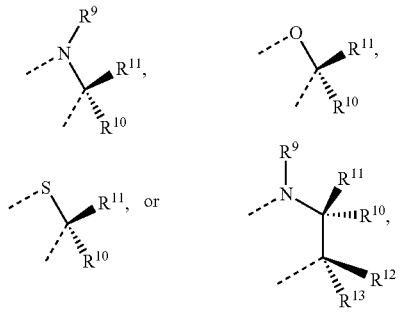

the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Optionally, $R^3$ may be as above and $R^1$ and $R^2$ together may be represented by

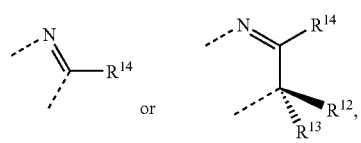

where the N of the $R^1/R^2$ linkage forms a bond to the pyrimidinone ring, each of $R^{12}$ or $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, such that each of $R^7$ and $R^8$ is, independently, a H, $C_1$-$C_6$ alkyl, $C_6$-$C_{12}$ aryl, heteroaryl, $C_1$-$C_4$ alkaryl, or $C_1$-$C_4$ alkheteroaryl.

As another alternative, $R^1$ and $R^2$ together may be represented by

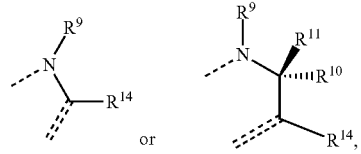

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing the $R^{14}$ and the nitrogen bearing $R^2$.

Optionally, the composition may have be a compound of formula (I), such that $R^1$ is a H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$. Accordingly, each of $R^4$ and $R^5$ may be, independently, a H, $C_{1-6}$ alkyl, $C_{6-12}$ aryl, heteroaryl, $C_{1-4}$ alkaryl, or $C_{1-4}$ alkheteroaryl, $R^2$ may be a H, $C_{1-6}$ alkyl, $C_{6-12}$ aryl, heteroaryl, $C_{1-4}$ alkaryl, or $C_{1-4}$ alkheteroaryl, and $R^3$ may be a H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, where $R^6$ is a $C_{1-6}$ alkyl, $C_{6-12}$ aryl, heteroaryl, $C_{1-4}$ alkaryl, or $C_{1-4}$ alkheteroaryl and each of $R^7$ and $R^8$ may be, independently, a H, $C_{1-6}$ alkyl, $C_{6-12}$ aryl, heteroaryl, $C_{1-4}$ alkaryl, or $C_{1-4}$ alkheteroaryl.

If desired, the composition contains a compound of formula:

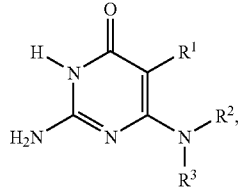
(I)

in which $R^1$ and $R^2$ together may be represented by

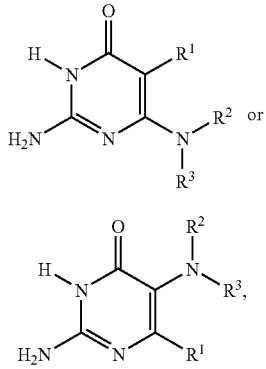
(I)
(II)

such that the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Alternatively, the composition contains a compound of formula:

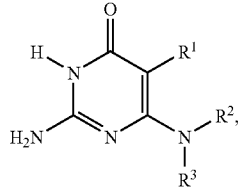
(I)

in which $R^3$ is as above and $R^1$ and $R^2$ together are represented by

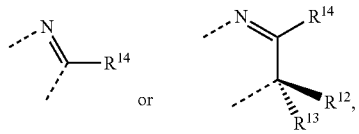

where the N of the $R^1/R^2$ linkage forms a bond to the pyrimidinone ring, each of $R^{12}$ and $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, where each of $R^4$, $R^7$ and $R^8$ is, independently, a H, $C_1$-$C_6$ alkyl, $C_6$-$C_{12}$ aryl, $C_1$-$C_4$ alkaryl, heteroaryl, or $C_1$-$C_4$ alkheteroaryl.

Alternatively, the composition contains a compound of formula:

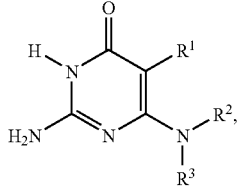
(I)

in which $R^1$ and $R^2$ together may be represented by

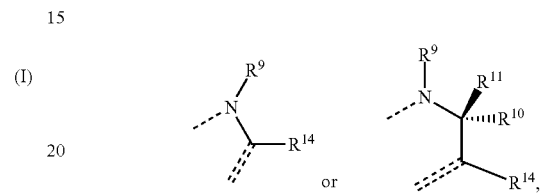

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$.

If the composition contains a compound of formula:

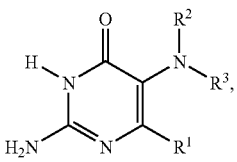
(II)

$R^1$ and $R^2$ together may be represented by

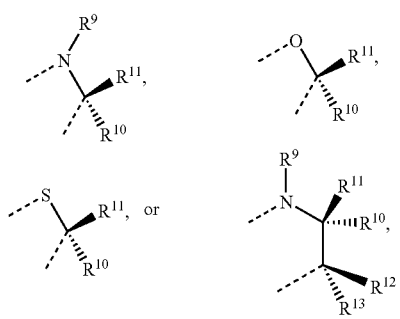

where the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Alternatively, the composition contains a compound of formula:

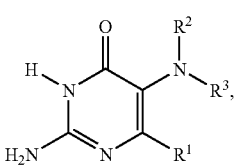
(II)

in which $R^3$ is as above and $R^1$ and $R^2$ together are represented by

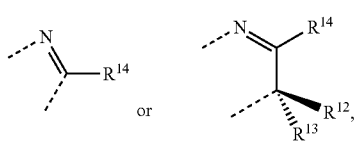

where the N of the $R^1/R^2$ linkage forms a bond to the pyrimidinone ring, each of $R^{12}$ and $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, such that each of $R^7$ and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl.

Optionally, the composition may contain a compound of formula:

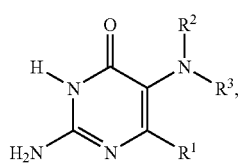

(II)

in which $R^1$ and $R^2$ together are represented by

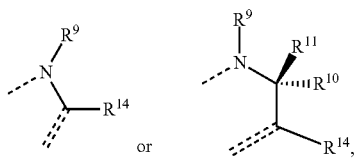

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$.

Exemplary compounds that may be contained within the composition of the invention include, for example:

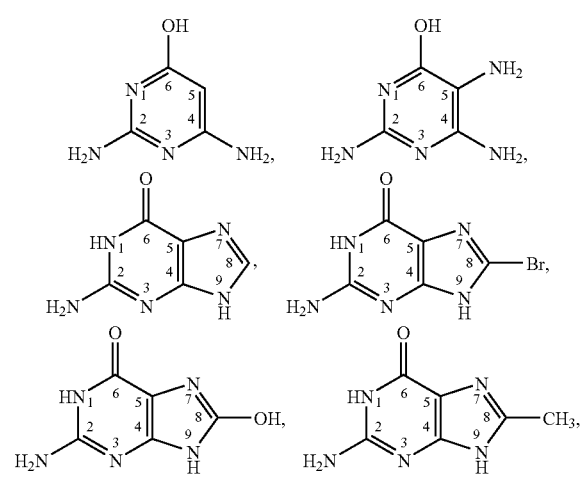

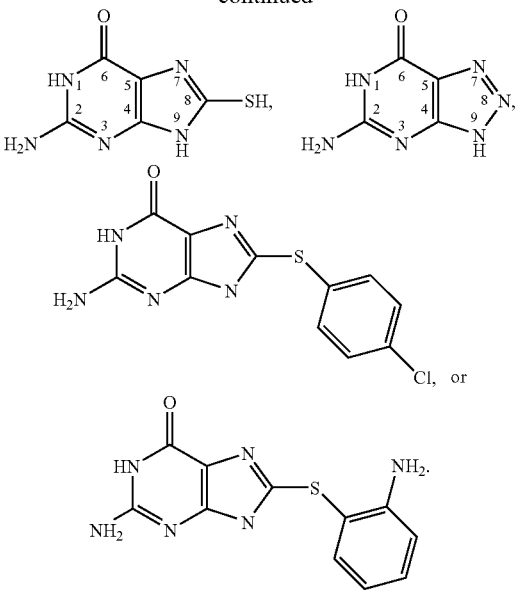

Furthermore, the composition of the invention may contain a compound having the formula:

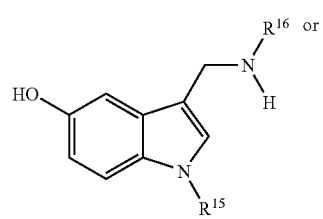

(III)

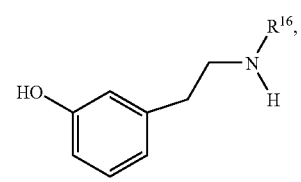

(IV)

in which $R^{15}$ is a H, $C_{1-6}$ alkyl, $C_{6-12}$ aryl, heteroaryl, $C_{1-4}$ alkaryl, or $C_{1-4}$ alkheteroaryl and $R^{16}$ is a H, $C_{1-6}$ alkyl, $C_{6-12}$ aryl, heteroaryl, $C_{1-4}$ alkaryl, $C_{1-4}$ alkheteroaryl, $CO_2R^{17}$, $CONR^{18}R^{19}$, $SO_2R^{17}$, or $SO_2NR^{18}R^{19}$. $R^{17}$ may be a $C_{1-6}$ alkyl, $C_{6-12}$ aryl, heteroaryl, $C_{1-4}$ alkaryl, or $C_{1-4}$ alkheteroaryl and each of $R^{18}$ and $R^{19}$ may be, independently, a H, $C_{1-6}$ alkyl, $C_{6-12}$ aryl, heteroaryl, $C_{1-4}$ alkaryl, or $C_{1-4}$ alkheteroaryl.

If desired, a second therapeutic agent, such as an analgesic agent, may be administered in combination with the composition of the invention, including for example, a non-steroidal anti-inflammatory agent (NSAIDs) (including acetaminophen, non-COX-2 selective agents, or COX-2 selective inhibitory drugs), opioid receptor agonist (e.g., morphine, codeine, hydrocodone, hydromorphone, levorphanol, methadone, meperidine, butorphanol, bupranorphine, nalbuphine, alfentanil, sufentanil, fentanyl, tramadol, pentazocine, propoxyphene, or oxycodone), tricyclic antidepressant (e.g., doxepin, amitriptyline, imipramine, nortriptyline, desipramine, or venlafaxine), SSRIs (e.g. paroxetine, sertraline, fluoxetine, or citalopram), anticonvulsants (e.g., phenytoin, carbamazepine, oxcarbazepine, lamotrigine, valproate, pregabalin, or gabapentin), voltage-gated sodium channel blockers, membrane stabilizers, nerve blockers (e.g. lidocaine, bupivicaine, prilocaine, or mexilitine), N-type calcium channel blockers (e.g ziconitide), serotonin receptor agonists such as 5-HT1D receptor agonists (e.g. sumatriptam, zolmatriptan, rizotriptan, naratriptan, almotriptan, or frovatriptan), steroids (e.g. cortisone, hydrocortisone, prednisolone, or methylprednisolone). According to this invention, the second therapeutic agent may or may not have a therapeutic effect (such as analgesia) when administered as a single agent but results in such an effect (or an additive or synergistic increase) when administered in combination with the composition of the invention. Other exemplary analgesic agents useful in the invention may include, for example, acetaminophen, acetylsalicylic acid, ibuprofen, naproxen, fenoprofen, indomethacin, ketorolac, rofecoxib, celecoxib, valdecoxib, paracoxib, clonazepam, diazepam, capsaicin, ketamine, clonidine, or baclofen.

Alternatively, the second therapeutic agent may be an inhibitor of any enzyme which utilizes BH4 as a cofactor including any of the following enzymes: all isoforms of nitric oxide synthase (NOS) such as eNOS, iNOS, or nNOS; tyrosine hydroxylase; tryptophan hydroxylase I (non-neuronal Tph1) and II (neuronal Tph2); phenylalanine hydroxylase; dopamine-β-hydroxylase; N-methyltransferase; and ether lipid oxidase. The second therapeutic agent may also include agents that inhibit direct effects of BH4 independent of its co-enzyme function, such as agents that interfere with BH4 binding to membrane bound receptors.

The composition of the invention and the second therapeutic agent may be administered together (as two separate formulations or a single formulation) or separately (e.g., within one hour, two hours, three hours, six hours, or twenty four hours of each other).

In another aspect, the invention features a method for diagnosing pain or a traumatic, metabolic or toxic peripheral nerve lesion in a mammal by measuring the levels of BH4, BH4 precursors, or intermediates (e.g., 7,8-dihydroneopterin triphosphate and 6-pyruvoyl tetrahydropterin), or BH4 metabolites (e.g., pterin, bipterin, 7,8 dihydropterin, 7,8 dihydroxanthopterin, xanthopterin, isoxanthopterin, leucopterin, or neopterin) in a biological sample of a mammal (e.g., in the serum, plasma, urine, cerebrospinal fluid, synovial fluid, tissue exudates, or tissue samples). According to this aspect of the invention, levels of BH4, BH4 precursors, BH4 intermediates, or BH4 metabolites serve as biomarkers of pain such that an increase in any of these molecules diagnoses pain in the mammal. Alternatively, the clinical diagnosis of pain may be supported in a mammal by measuring the level (e.g., mRNA or protein levels) or activity of any one of the BH4 synthetic enzymes (e.g., sepiapeterin reductase (SPR), Pyruvoyltetrahydropterin Synthase (PTPS), GTP cyclohydrolase (GTPCH), Pterin-4α-carbinolamine dehydratase, and dihydropteridine reductase (DHPR)) in the mammal. Similarly, the pain diagnosis is supported by determining an increase in the activity or level of such enzymes.

The present invention also provides a method for identifying a candidate compound for treating, reducing, or preventing pain or endogenous mechanisms that further increase a traumatic, metabolic or toxic peripheral nerve lesion in a mammal. The method involves the steps of: (a) contacting a cell synthesizing BH4 with a candidate compound; and (b) measuring the BH4 level or activity (e.g., ability to function as a co-factor or ability to bind membrane-bound receptors). A compound that decreases the level or activity of BH4 relative to the BH4 level or activity in a cell not contacted with the compound is identified as a candidate compound for treating, reducing, or preventing pain or a traumatic, metabolic or toxic peripheral nerve lesion in a mammal. Alternatively, the cell in step (a) may express any one of the BH4 synthetic enzymes (e.g., sepiapeterin reductase (SPR), Pyruvoyltetrahydropterin Synthase (PTPS), GTP cyclohydrolase (GTPCH), Pterin-4α-carbinolamine dehydratase, and dihydropteridine reductase (DHPR)) and, optionally, step (b) involves measuring the expression or biological activity of such enzymes to assess the inhibitory activity of the candidate compound. If desired, the BH4 synthetic enzyme may be a protein fusion gene. In preferred embodiments, step (b) involves the measurement of BH4 levels or activity, or alternatively, the measurement of the mRNA or protein levels or enzyme activity of one of the BH4 synthetic enzymes. Preferably, the cell is a mammalian cell (e.g., a human or rodent cell).

In a related aspect, the invention provides an alternative method for identifying a candidate compound for treating, reducing, or preventing pain or a traumatic, metabolic or toxic peripheral nerve lesion in a mammal. This method involves the steps of: (a) identifying a pteridine or specific BH4 binding site on a protein (e.g., a BH4-binding receptor or BH4-dependent enzyme); (b) contacting such a BH4 binding protein (receptor or enzyme) with a candidate compound; and (c) determining whether the candidate compound binds to the BH4 site on the protein and inhibits BH4 binding or activity on the protein (for example, by itself binding to the BH4 site). Compounds that inhibit BH4 activity or binding are identified as candidate compounds for treating, reducing, or preventing pain or a traumatic, metabolic or toxic peripheral nerve lesion. Optionally, this method may further involve contacting the candidate compound with any one of the enzymes that use BH4 as a cofactor (e.g., NOS) or membrane receptors that bind BH4 and determining whether the candidate compound binds and/or inhibits the activity of such an enzyme or receptor.

The invention also provides yet another method for identifying a candidate compound for treating, reducing, or preventing pain or a traumatic, metabolic or toxic a peripheral nerve lesion in a mammal. This method involves the steps of: (a) providing GTP cyclohydrolase (GTPCH), GTPCH Feedback Regulatory Protein (GFRP), and a candidate compound; (b) measuring the binding of the GTPCH and the GFRP; and (c) identifying a candidate compound as useful for treating, reducing, or preventing pain or a traumatic, metabolic or toxic peripheral nerve lesion, wherein the binding of the GTPCH and GFRP is increased in the presence of the candidate compound. In preferred embodiments, the GTPCH and GFRP are human proteins. In this method, the candidate compound may preferably bind to either GFRP or the GTPCH:GFRP complex.

In preferred embodiments, the method also tests the ability of the candidate compound to reduce the expression of one or all of the BH4 synthetic enzymes in a cell, for example, a mammalian cell such as a rodent or human cell leading to a reduction in BH4 levels. Most preferably, the BH4 synthetic enzyme gene is human sepiapterin reductase (SPR), Pyruvoyltetrahydropterin Synthase (PTPS), GTP cyclohydrolase I (GTPCH I), Pterin-4α-carbinolamine dehydratase, or dihydropteridine reductase (DHPR).

The present invention further includes kits for carrying out the methods of the invention. For example, the invention includes a kit containing a composition that reduces the level and activity of tetrahydrobiopterin (BH4) in an amount sufficient to treat, reduce, or prevent pain or a traumatic, metabolic or toxic peripheral nerve lesion as well as instructions for delivery of the composition to a mammal for treating, reducing, or preventing pain or a traumatic, metabolic or toxic peripheral nerve lesion.

The present invention further includes a diagnostic kit for the measurement of BH4, its precursors and intermediates (e.g., 7,8-dihydroneopterin triphosphate and 6-pyruvoyl tetrahydropterin), or metabolites (e.g., pterin, biopterin, 7,8 dihydropterin, 7,8 dihydroxanthopterin, xanthopterin, isoxanthopterin, leucopterin, and neopterin) from a biological sample of a mammal (e.g., serum, plasma, urine, cerebrospinal fluid, synovial fluid, tissue exudates, and tissue samples). For example, the invention includes a kit containing an antibody that is specific to BH4 as well as instructions for diagnosing pain in a mammal.

The invention also features methods for identifying a BH4 target protein. The first method consists of the steps of: (a) providing a sample and BH4; (b) contacting the sample with the BH4 under conditions that allow binding between the sample proteins and the BH4; and (c) assessing the binding of the BH4 to a sample protein by detecting the BH4, wherein a sample protein that binds to BH4 is identified as a BH4 target protein. In one embodiment, the assessing step (c) uses a detection method such as mass spectrometry, surface plasmon resonance microscopy, or atomic force microscopy. Biological samples which can be used in this method to identify BH4 target proteins may come from any source. Preferred samples are extracts prepared from mammalian nervous tissue such as, for example, nervous tissue containing the dorsal horn or the dorsal root ganglia. Preferably, samples contain membrane-bound proteins.

A second method for identifying a BH4 target protein contains the steps of (a) providing BH4 and an array, wherein the array consists of a plurality of immobilized purified protein species, wherein each of the protein species in the array is spatially separated from each of the other protein species; (b) contacting the array with the BH4 under conditions that allow binding between the protein species and the BH4; and (c) assessing the binding of the BH4 to the protein species, wherein a protein species that binds to the BH4 is identified as a BH4 target protein.

In preferred embodiments of either of the two foregoing methods, the BH4 is detectably labeled. Useful detectable labels include, for example, a radioisotope (e.g., tritium) or biotin. In other useful embodiments, the assessing step (c) requires the use of a BH4-specific antibody.

Finally, the invention features compositions for reducing BH4 biological activity. Compositions of the invention may have the formula:

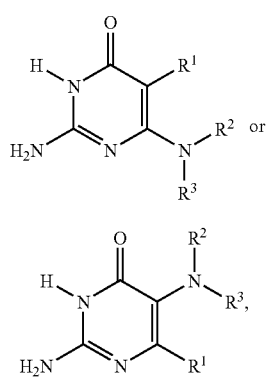

(I)

such that $R^1$ is a H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$. Each of $R^4$ and $R^5$ may be, independently, a H, $C_{1-6}$ alkyl, $C_{6-12}$ aryl, heteroaryl, $C_{1-4}$ alkaryl, or $C_{1-4}$ alkheteroaryl; $R^2$ may be a H, $C_{1-6}$ alkyl, $C_{6-12}$ aryl, heteroaryl, $C_{1-4}$ alkaryl, or $C_{1-4}$ alkheteroaryl; and $R^3$ may be a H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, where $R^6$ is a $C_{1-6}$ alkyl, $C_{6-12}$ aryl, heteroaryl, $C_{1-4}$ alkaryl, or $C_{1-4}$ alkheteroaryl, and each of $R^7$ and $R^8$ is, independently, a H, $C_{1-6}$ alkyl, $C_{6-12}$ aryl, heteroaryl, $C_{1-4}$ alkaryl, or $C_{1-4}$ alkheteroaryl.

Alternatively, $R^3$ may be as above and $R^1$ and $R^2$ together may be represented by

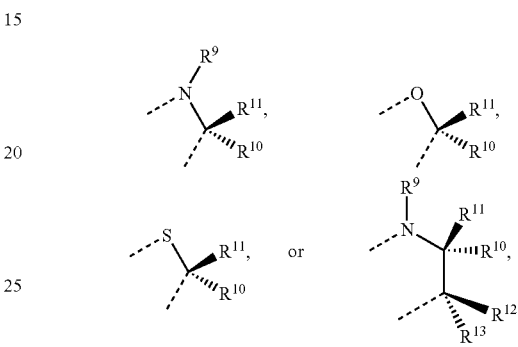

where the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Optionally, $R^3$ may be as above and $R^1$ and $R^2$ together may be represented by

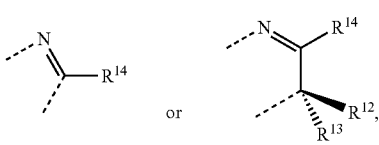

where the N of the $R^1/R^2$ linkage forms a bond to the pyrimidinone ring, each of $R^{12}$ or $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, such that each of $R^7$ and $R^8$ is, independently, a H, $C_1$-$C_6$ alkyl, $C_6$-$C_{12}$ aryl, heteroaryl, $C_1$-$C_4$ alkaryl, or $C_1$-$C_4$ alkheteroaryl.

As another alternative, $R^1$ and $R^2$ together may be represented by

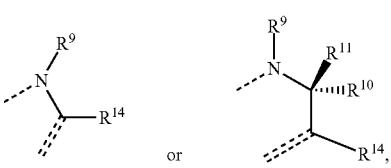

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing the $R^{14}$ and the nitrogen bearing $R^2$.

Optionally, the composition may have be a compound of formula (I), such that $R^1$ is a H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$. Accordingly, each of $R^4$ and $R^5$ may be, independently, a H, $C_{1-6}$ alkyl, $C_{6-12}$ aryl, heteroaryl, $C_{1-4}$ alkaryl, or $C_{1-4}$ alkheteroaryl, $R^2$ may be a H, $C_{1-6}$ alkyl, $C_{6-12}$ aryl, heteroaryl, $C_{1-4}$ alkaryl, or $C_{1-4}$ alkheteroaryl, and $R^3$ may be a H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, where $R^6$ is a $C_{1-6}$ alkyl, $C_{6-12}$ aryl, heteroaryl, $C_{1-4}$ alkaryl, or $C_{1-4}$ alkheteroaryl and each of $R^7$ and $R^8$ may be, independently, a H, $C_{1-6}$ alkyl, $C_{6-12}$ aryl, heteroaryl, $C_{1-4}$ alkaryl, or $C_{1-4}$ alkheteroaryl.

If desired, the composition contains a compound of formula:

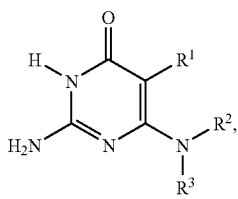

(I)

in which $R^1$ and $R^2$ together may be represented by

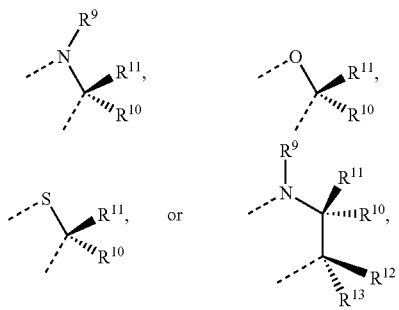

such that the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Alternatively, the composition contains a compound of formula:

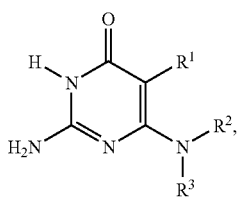

(I)

in which $R^3$ is as above and $R^1$ and $R^2$ together are represented by

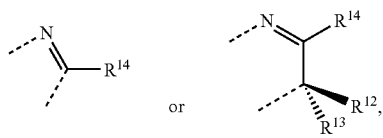

where the N of the $R^1/R^2$ linkage forms a bond to the pyrimidinone ring, each of $R^{12}$ and $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, where each of $R^4$, $R^7$ and $R^8$ is, independently, a H, $C_1$-$C_6$ alkyl, $C_6$-$C_{12}$ aryl, $C_1$-$C_4$ alkaryl, heteroaryl, or $C_1$-$C_4$ alkheteroaryl.

Alternatively, the composition contains a compound of formula:

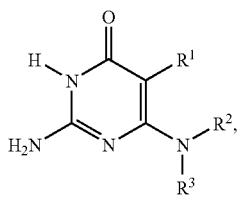

(I)

in which $R^1$ and $R^2$ together may be represented by

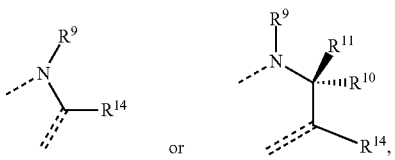

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$.

If the composition contains a compound of formula:

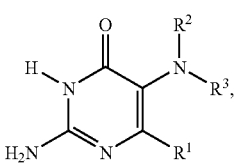

(II)

$R^1$ and $R^2$ together may be represented by

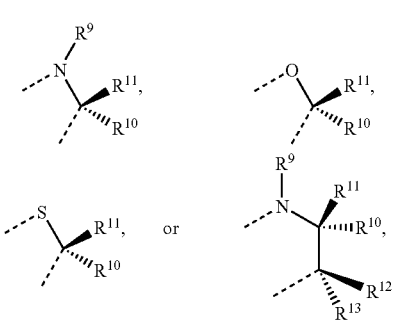

where the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Alternatively, the composition contains a compound of formula:

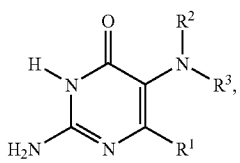

(II)

in which $R^3$ is as above and $R^1$ and $R^2$ together are represented by

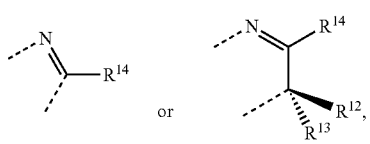

where the N of the $R^1/R^2$ linkage forms a bond to the pyrimidinone ring, each of $R^{12}$ and $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, such that each of $R^7$ and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl.

Optionally, the composition may contain a compound of formula:

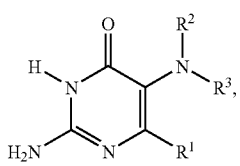

(II)

in which $R^1$ and $R^2$ together are represented by

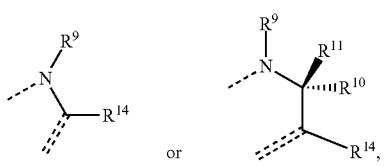

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$.

Exemplary compounds that may be contained within the composition of the invention include, for example:

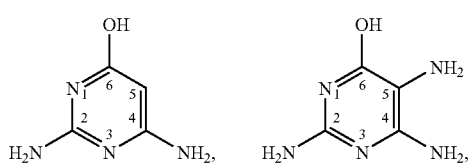

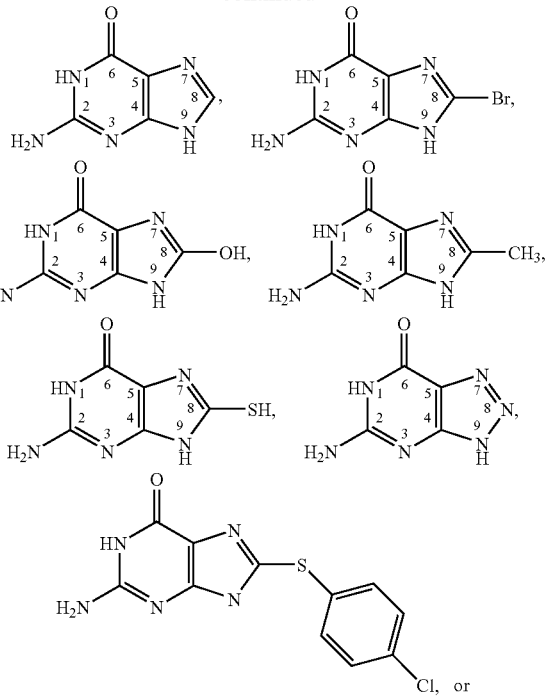

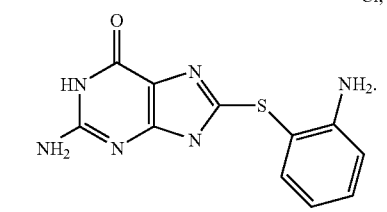

Furthermore, the composition of the invention may contain a compound having the formula:

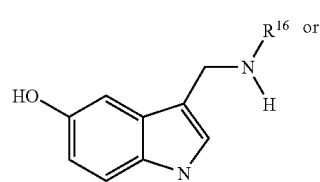

(III)

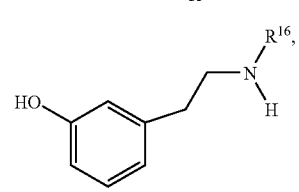

(IV)

in which $R^{15}$ is a H, $C_{1-6}$ alkyl, $C_{6-12}$ aryl, heteroaryl, $C_{1-4}$ alkaryl, or $C_{1-4}$ alkheteroaryl and $R^{16}$ is a H, $C_{1-6}$ alkyl, $C_{6-12}$ aryl, heteroaryl, $C_{1-4}$ alkaryl, $C_{1-4}$ alkheteroaryl, $CO_2R^{17}$, $CONR^{18}R^{19}$, $SO_2R^{17}$, or $SO_2NR^{18}R^{19}$. $R^{17}$ may be a $C_{1-6}$ alkyl, $C_{6-12}$ aryl, heteroaryl, $C_{1-4}$ alkaryl, or $C_{1-4}$ alkheteroaryl and each of $R^{18}$ and $R^{19}$ may be, independently, a H, $C_{1-6}$ alkyl, $C_{6-12}$ aryl, heteroaryl, $C_{1-4}$ alkaryl, or $C_{1-4}$ alkheteroaryl.

The compositions of the invention may be combined with any second therapeutic suitable for use in the above-described methods. The compositions alone or in combination with any second therapeutic may be present in a therapeutic composition in association with a pharmaceutically acceptable carrier or excipient.

By "BH4 synthetic enzyme fusion gene" is meant a promoter and/or all or part of a coding region of a BH4 synthetic enzyme (e.g., sepiapeterin reductase (SPR), Pyruvoyltetrahydropterin Synthase (PTPS), GTP cyclohydrolase (GTPCH), Pterin-4α-carbinolamine dehydratase, and dihydropteridine reductase (DHPR)) operably linked to a second, heterologous nucleic acid sequence. In preferred embodiments, the second, heterologous nucleic acid sequence is a reporter gene, that is, a gene whose expression may be assayed; exemplary reporter genes include, without limitation, those genes encoding glucuronidase (GUS), luciferase, chloramphenicol transacetylase (CAT), green fluorescent protein (GFP), alkaline phosphatase, and β-galactosidase.

By a "candidate compound" is meant a chemical, be it naturally-occurring or artificially-derived. Candidate compounds include, for example, peptides, polypeptides, synthetic organic molecules, naturally occurring organic molecules, nucleic acids, peptide nucleic acids, and components thereof.

By "dominant negative protein" is meant any polypeptide having at least 50%, 70%, 80%, 90%, 95%, or even 99% sequence identity to 10, 20, 35, 50, 100, 150, or more than 150 amino acids of the wild type protein to which the dominant negative protein corresponds. In addition to inactivating mutations, dominant negative proteins may consist of deletions or truncations of a wild-type molecule. For example, a dominant negative BH4 synthetic enzyme may be a truncated BH4 synthetic enzyme mutant that has a deletion such that it no longer functions to produce BH4 or its intermediates (e.g., 7,8-dihydroneopterin triphosphate and 6-pyruvoyl tetrahydropterin) including, for example, a GTPCH that has lost its catalytic activity, thereby disrupting the BH4 synthetic pathway.

By "opioid receptor agonist" is meant any naturally occurring, semi-synthetic, or synthetic compound that binds to the mu, kappa, or delta opioid receptor subtypes and mimics the function of opioids at these receptors. The opioid receptor agonist may be a peptide or a non-peptide compound. Preferably, opioid receptor agonists have a $K_d$ for at least one opioid receptor subtype of <1 µM, more preferably <100 nM, most preferably <10 nM, or even <1 nM. Opioid receptor agonists include generally, for example, members from the phenanthrene, phenyl heptylamine, phenylpiperidine, morphinan, and benzomorphan chemical families. Opioid receptor agonists include, for example, morphine, hydormorphone, oxymorphone, codeine, oxycodone, hydrocodone, methadone, meperidine, levorphanol, nalbuphine, sufentanil, alfentanil, buprenorphine, pentazocine, propoxyphene and butorphanol.

By "an effective amount" is meant an amount of a compound, alone or as part of a combination according to the invention, required to prevent, reduce, or eliminate the sensation of pain. The effective amount of active compound(s) used to practice the present invention for therapeutic treatment of pain varies depending upon the manner of administration, the age, and body weight, of the subject as well as the underlying pathology that is causing the pain. Ultimately, the attending physician or veterinarian will decide the appropriate amount and dosage regimen. Such amount is referred to as an "effective" amount.

By "pain" is meant all types of pain including, for example, peripheral and central neuropathic pain, functional pain, inflammatory pain or nociceptive pain, whether acute or chronic. Exemplary pain conditions include post-operative or post-traumatic pain, chronic lower back pain, pain of rheumatoid arthritis, osteoarthritis, fibromyalgia, cluster headaches, post-herpetic neuralgia, phantom limb pain, central stroke pain, dental pain, opioid-resistant pain, visceral pain, bone injury pain, labor pain, pain resulting from burns including sunburns, post-partum pain, migraine, tension type headache, angina pain, and genitourinary tract-related pain (e.g., cystitis).

By "reduce the tetrahydrobiopterin (BH4) biological activity" is meant to reduce a functional outcome associated with a biological activity attributed to BH4. Generally, the reduction of BH4 biological activity may be the result of, for example, a reduction in the amount (level) of the BH4 molecules and may be affected by reducing/inhibiting de novo BH4 synthesis, increasing/accelerating BH4 catabolism, or a combination of the two. Alternatively, the biological activity of BH4 may be reduced by inhibiting the effect of BH4 at a target molecule. For example, a competitive BH4 inhibitor that binds to a BH4 binding site on an effector protein (e.g, an enzyme) will reduce the biological activity. Non-competitive BH4 inhibitors are also included in this definition. Likewise, a BH4 binding molecule which effectively sequesters BH4 and prevents it from binding to an effector molecule also has the effect of reducing BH4 biological activity. Such reduction may be, for example, a decrease of least 10%, 20%, 30%, 40%, 50%, 60%, 70%, 80%, 90%, 100%, or greater than 100%, relative to control conditions. More specifically, BH4 level or activity may be decreased, for example, by reducing the enzyme activity of enzymes involved in the BH4 synthesis pathway, such as GTP cyclohydrolase (GTPCH), Sepiapterin Reductase (SPR), and Dihydropteridine reductase (DHPR). Preferably, such enzyme activity is reduced by at least 10%, 20%, 30%, 40%, 50%, 60%, 70%, 80%, 90%, 100%, or even greater than 100%, relative to a control. GTPCH may, for example, be inhibited by increasing the levels or binding activity of GTPCH Feedback Regulatory Protein (GFRP).

By "treating, reducing, or preventing pain" is meant preventing, reducing, or eliminating the sensation of pain in a subject before, during, or after it has occurred. As compared with an equivalent untreated control, such reduction or degree of prevention is at least 5%, 10%, 20%, 40%, 50%, 60%, 80%, 90%, 95%, or 100% as measured by any standard technique known in the art. To treat pain, according to the methods of this invention, the treatment does not necessarily provide therapy for the underlying pathology that is causing the painful sensation. Treatment of pain can be purely symptomatic.

By "diagnosing pain" is meant detecting pain caused by any stimulus in a mammal including damage to peripheral nerves. For example, pain may be diagnosed by detecting a surrogate marker that is associated or correlated with the sensation of pain. According to the invention, pain or a traumatic, metabolic or toxic peripheral nerve lesion is diagnosed by measuring and detecting an increase in the levels of BH4, BH4 intermediates, BH4 precursors, or BH4 metabolites in a biological sample from the mammal (e.g., serum, plasma, urine, cerebrospinal fluid, synovial fluid, tissue exudates, or tissue samples). Pain is diagnosed in a mammal if such levels are increased by at least 10%, 20%, 30%, 40%, 50%, 60%, 80%, 90%, 95%, 100, or more than 100% above a control. Alternatively, the levels or activity of any one of BH4 synthetic enzymes are measured and pain is diagnosed if an increase in the level or activity of a BH4 enzyme is detected. Desirably, such increase is at least 10%, 20%, 30%, 40%, 50%, 60%, 80%, 90%, 95%, 100%, or more than 100% above control conditions.

By "specific for" as used herein in reference to an antibody is meant an increased affinity of an antibody for a particular protein or antigen, relative to an equal amount of any other protein or antigen. For example, an antibody (e.g., a human monoclonal antibody) that is specific for BH4 desirably has an affinity for BH4 that is least 2-fold, 5-fold, 10-fold, 30-fold, or 100-fold greater than for an equal amount of any other antigen, including related antigens. Binding of an antibody to another protein or antigen may be determined as described herein, and by any number of standard methods in the art, e.g., Western analysis, ELISA, or co-immunoprecipitation.

By "substantially identical," when referring to a protein or polypeptide, is meant a protein or polypeptide exhibiting at least 75%, but preferably 85%, more preferably 90%, most preferably 95%, or even 99% identity to a reference amino acid sequence. For proteins or polypeptides, the length of comparison sequences will generally be at least 20 amino acids, preferably at least 30 amino acids, more preferably at least 40 amino acids, and most preferably 50 amino acids or the full length protein or polypeptide. Nucleic acids that encode such "substantially identical" proteins or polypeptides constitute an example of "substantially identical" nucleic acids; it is recognized that the nucleic acids include any sequence, due to the degeneracy of the genetic code, that encodes those proteins or polypeptides. In addition, a "substantially identical" nucleic acid sequence also includes a polynucleotide that hybridizes to a reference nucleic acid molecule under high stringency conditions.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65 C, or a buffer containing 48% formamide, 4.8×SSC, 0.2 M Tris-Cl, pH 7.6, 1×Denhardt's solution, 10% dextran sulfate, and 0.1% SDS, at a temperature of 42 C. Other conditions for high stringency hybridization, such as for PCR, Northern, Southern, or in situ hybridization, DNA sequencing, etc., are well known by those skilled in the art of molecular biology. See, e.g., F. Ausubel et al., *Current Protocols in Molecular Biology*, John Wiley & Sons, New York, N.Y., 1998, hereby incorporated by reference.

As used herein, the terms "alkyl" and the prefix "alk-" are inclusive of both straight chain and branched chain saturated or unsaturated groups, and of cyclic groups, including cycloalkyl and cycloalkenyl groups. Unless otherwise specified, acyclic alkyl groups contain 1 to 6 carbons. Cyclic groups can be monocyclic or polycyclic and preferably have 3 to 8 ring carbon atoms. Exemplary cyclic groups include cyclopropyl, cyclopentyl, cyclohexyl, and adamantyl groups. The alkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "aryl" is meant a carbocyclic aromatic ring or ring system. Unless otherwise specified, aryl groups contain 6 to 18 carbons. Examples of aryl groups include phenyl, naphthyl, biphenyl, fluorenyl, and indenyl groups.

By "heteroaryl" is meant an aromatic ring or ring system that contains at least one ring hetero-atom (e.g., O, S, Se. N, and P). Unless otherwise specified, heteroaryl groups contain 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

By "heterocycle" is meant a non-aromatic ring or ring system that contains at least one ring heteroatom (e.g., O, S, Se, N, and P). Unless otherwise specified, heterocyclic groups contain 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents including for example a $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (in which the alkyl group has 1 to 6 carbon atoms), and alkheteroaryl (in which the alkyl group has 1 to 6 carbon atoms).

By "alkoxy" is meant a chemical substituent of the formula —OR, where R is an alkyl group. By "aryloxy" is meant a chemical substituent of the formula —OR, where R is an aryl group. By "alkaryl" is meant a chemical substituent of the formula —RR, where R is an alkyl group and R is an aryl group. By "alkheteraryl" is meant a chemical substituent of the formula —RR, where R is an alkyl group and R is a heteroaryl group.

By "halide" or "halogen" or "halo" is meant bromine, chlorine, iodine, or fluorine.

Overall, the present invention provides significant advantages over standard therapies for the diagnosis, treatment, and prevention of pain. Based on our results, the administration of a therapeutic agent (e.g., methotrexate) that reduces the level or activity of BH4 attenuates pain in part by interfering with the activity of enzymes that utilize BH4 as a co-factor or membrane-bound receptors that bind to BH4 and modulate neuronal excitability or transmitter release. The present invention further allows the diagnosis of pain in a mammal by measuring and detecting an increase in the levels of BH4, BH4 intermediates, BH4 metabolites, or BH4 precursors, or alternatively, by measuring and detecting an increase in the activity or levels of any one the BH4 synthetic enzymes. In addition, the candidate compound screening methods provided by the present invention allow for the identification of novel therapeutics that modify the injury process and mitigate the symptoms by reducing the synthesis or action of BH4.

BRIEF DESCRIPTION OF THE DRAWINGS

FIG. 1A is a graph representing the microarray expression profile analysis of twenty-three genes, including Dihydropteridine reductase (DHPR), in the dorsal root ganglia (DRG) during development and adulthood, before and following peripheral nerve injury.

FIG. 1B represents a Northern slot blot analysis confirming mRNA regulation of DHPR in the dorsal root ganglia during development and in the adult, before and following peripheral nerve injury.

FIG. 3 is a table showing the change in expression levels of members of the BH4 synthetic pathway before and following peripheral nerve injury detected by microarrays.

FIG. 6A shows the expression profile in the DRG. Changes in the expression of BH4 synthetic enzymes in the dorsal horn are shown in FIG. 6B. The enzymes are present both in the DRG and dorsal horn.

In FIG. 8A, rats were treated with DAHP (180 mg/kg/d i.p.) for three days starting three days after surgery (early treatment). Nociceptive behavior was assessed daily before and after drug injection. In FIG. 8B, the treatment period was extended to five days (180 mg/kg/d i.p.) starting three days after surgery and pain behavior was assessed daily before and after drug injection and once every second day for an additional week after stopping the daily drug injections. In FIG. 8C, treatment with DAHP (180 mg/kg/d i.p. for 5 days) was started 17 days after surgery i.e. in the chronic phase without any treatment in the early phase. Nociceptive behavior was assessed once daily 3 h after drug injection. In FIG. 8D, animals received a continuous spinal infusion of DAHP (6 mg/kg/d) for 14 days. The infusion was started directly after surgery. Nociceptive behavior was assessed once daily.

FIG. 9A shows the threshold to mechanical stimuli applied with von Frey hairs (von Frey threshold). FIG. 9B shows the duration of paw licking, shaking and lifting following acetone application to the paw as a measure for cold allodynia. DAHP treatment (180 mg/kg/d i.p. for 5 days) was started 3 days after surgery and nociceptive behavior was assessed daily before and after drug injection and once every second day after stopping daily drug injections.

FIG. 11A shows the paw withdrawal latency in response to radiant heat (Hargreaves test) of the CFA treated, inflamed paw. On the left end of the graph, two doses of DAHP (180 mg/kg i.p.) were injected, the first 30 minutes before injection of CFA into the hindpaw, the second 4 hours after CFA (indicated with arrows D1 and D2). On the right, a single dose (dotted arrow D1) of DAHP (180 mg/kg i.p.) was injected 24 h after induction of paw inflammation without any treatment during the first 24 h following CFA injection. FIG. 11B shows the respective paw withdrawal latencies of the non-inflamed contralateral paw. In FIGS. 11C-11D, the effects of systemically administered DAHP (180 mg/kg i.p. single dose; 11C) are compared with the effects of a single intrathecal dose (1 mg/kg i.t.; 11D) which was administered via a lumbar spinal catheter. In both cases, treatment was started 24 hours after CFA injection into the hindpaw. Because of slightly different baseline levels (11C compared with 11D) effects of DAHP after i.p. and i.t. treatment are additionally presented as percentage change of paw withdrawal latency (FIG. 11E) to allow for a direct comparison of both routes of administration.

FIG. 14A shows the time course of DAHP plasma concentrations following i.p. injection of a single dose of 180 mg/kg at time "zero". In addition, concentrations of DAHP in cerebrospinal fluid (CSF) were determined at an early and late time point. In FIG. 14B, plasma concentrations were fitted according to a one-compartment PK model with first order input and first order elimination. PK parameters are presented where Cmax is the maximum concentration, tmax the time of the maximum concentration, k01 is the absorption rate constant, t1/2abs. represents the absorption half-life, k10 is the elimination rate constant, t1/2 el is the elimination half-life, and Cl is the clearance. In FIG. 14C, pooled plasma concentration and effect data of the CFA model were used to assess the PK/PD relationship employing a standard sigmoidal Emax model.

FIG. 15B shows the increase of the paw weight of the inflamed paw compared with the contralateral paw. Paw weight was determined 48 hours following CFA injection. The increase of the paw weight is a measure for the inflammatory paw edema.

In FIGS. 16A, and 16B the left panel shows the threshold to mechanical stimuli applied with von Frey hairs (von Frey threshold). The right panel shows the duration of paw licking, shaking and lifting following acetone application to the paw as a measure for cold allodynia. In FIG. 16A MTX (0.2 mg/kg/d) was injected i.p. once daily starting 5 days after SNI surgery. Nociceptive behavior was assessed once daily three hours after drug injection. In FIG. 16B, MTX was administered as continuous intrathecal infusion (0.1 mg/kg/d for 14 days) starting right after SNI surgery. Nociceptive behavior was assessed once daily. FIGS. 16C and 16D show the body weight gain of animals during systemic (16C) and intrathecal (16D) MTX treatment. Determination of the weight gain was used to assess general well-being and potential toxic effects of MTX.

FIG. 17 is a table showing various sepiapterin reductase inhibitors (Smith et al., (1992) *J Biol Chem* 267: 5599-5607).

FIG. 19 is a table representing potential GTPCH inhibitors.

FIG. 20 shows the structure of GTPCH and the binding of its substrate to the catalytic center of the enzyme. Hydrogen bonds between aminoacids of GTPCH and the substrate GTP are shown as dotted lines.

FIG. 21 shows the interaction of GTPCH-I with the feedback regulatory protein (GFRP) and binding site of phenylalanine in the interface of both proteins. The binding site of BH4 and GFRP-dependent GTPCH-I inhibitors is thought to be similar to that of phenylalanine.

FIGS. 23A and 23B are a series of graphs demonstrating the pro-nociceptive effects of BH4. FIG. 23A demonstrates that intrathecal administration of BH4 reduces the paw withdrawal latency to a thermal (heat) stimulus in naïve rats. FIG. 23B demonstrates the pro-nociceptive effects of BH4 in animals having a pre-existing thermal hypersensitivity (ipsilateral) compared to controls (contralateral). Hypersensitivity was induced using the CFA model of paw inflammation. In these experiments, BH4 was injected at time "zero" after measurement of baseline paw withdrawal latency.

FIG. 24A is a series of photo micrographs showing cFos immunoreactivity in ipsilateral dorsal horn neurons two hours after formalin injection in DAHP and vehicle-treated rats. FIG. 24B is a bar graph quantifying the number of cFos immunoreactive cell bodies observed under each condition.

FIG. 26A is a series of graphs demonstrating that there is no significant difference between wild-type and nNOS knockout mice, using the SNI model either with or without treatment using DAHP, in response to mechanical or thermal (cold) stimuli. In this figure, closed circles represent nNOS knockout mice with DAHP; open circles, nNOS knock out mice with vehicle; closed triangles, wild type mice with DAHP; and open triangles, wild type mice with vehicle. FIG. 26B is a series of line graphs demonstrating that L-NAME, a NOS inhibitor, does not enhance the anti-nociceptive effects of DAHP to mechanical or thermal (cold) stimuli in the SNI model. In this figure, closed triangles represent L-NAME administration; open circles, L-NAME+DAHP administration; closed circles, DAHP administration; and open triangles, vehicle administration. L-NAME was administered at 25 mg/kg, i.p., single dose, and DAHP was administered at 120 mg/kg, i.p., single dose. The antinociceptive efficacy of this high L-NAME dose is weaker (about 50%) than that of a moderate dose of DAHP.

FIG. 27A is a series of photomicrographs of in situ hybridization of GTPCH-I in the ipsilateral (lesioned) and contralateral (control) dorsal root ganglia 3 days (top panel) and 14 days (bottom panel) after SNI surgery. FIG. 27B is a series of photomicrographs of GTPCH-I in situ hybridization 14 days after SNI surgery and treatment with either DAHP or vehicle control. These data demonstrate that DAHP does not affect GTPCH-1 expression in the SNI model.

FIG. 28A is a series of photomicrographs demonstrating that GTPCH-1 mRNA is not normally expressed in the spinal cord but, three days after SNI surgery, isolated GTPCH-1-expressing motor neurons could be observed. FIG. 28B is a series of photomicrographs demonstrating that GFRP is expressed in isolated DRG neurons, but that the expression pattern does not change three days after SNI surgery.

DETAILED DESCRIPTION

In general, the present invention features methods and compounds for treating, reducing, or preventing pain or a traumatic, metabolic or toxic peripheral nerve lesion by administering to a mammal a therapeutically effective amount of a composition that reduces the level or activity of tetrahydrobiopterin (BH4). The invention also provides methods for diagnosing pain or a traumatic, metabolic or toxic peripheral nerve lesion in a mammal by detecting an increase in the levels of BH4, BH4 intermediates, BH4 precursors, or BH4 metabolites in a biological sample obtained from a mammal (e.g., serum, plasma, urine, cerebrospinal fluid, synovial fluid, tissue exudates, or tissue samples). Alternatively, pain may be diagnosed by detecting an increase in the activity or levels of any one of the BH4 synthetic enzymes. In yet another general embodiment, the invention provides methods for identifying novel therapeutics for pain based on their ability to decrease the level or activity of BH4 or its synthetic enzymes or its ability to interfere with binding of BH4 to a BH4 receptor or BH4-dependent enzyme.

Figure 2A:
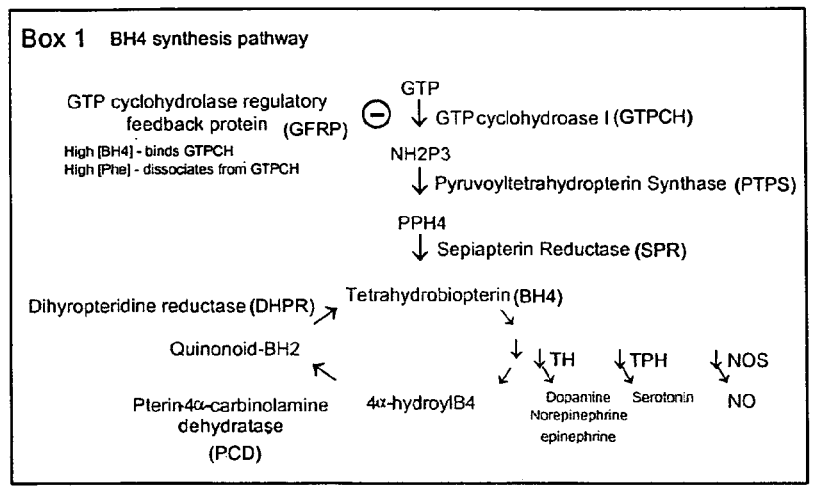
FIG. 2A is a schematic diagram outlining the Tetrahydrobiopterin (BH4) synthesis pathway.
Figure 2B:
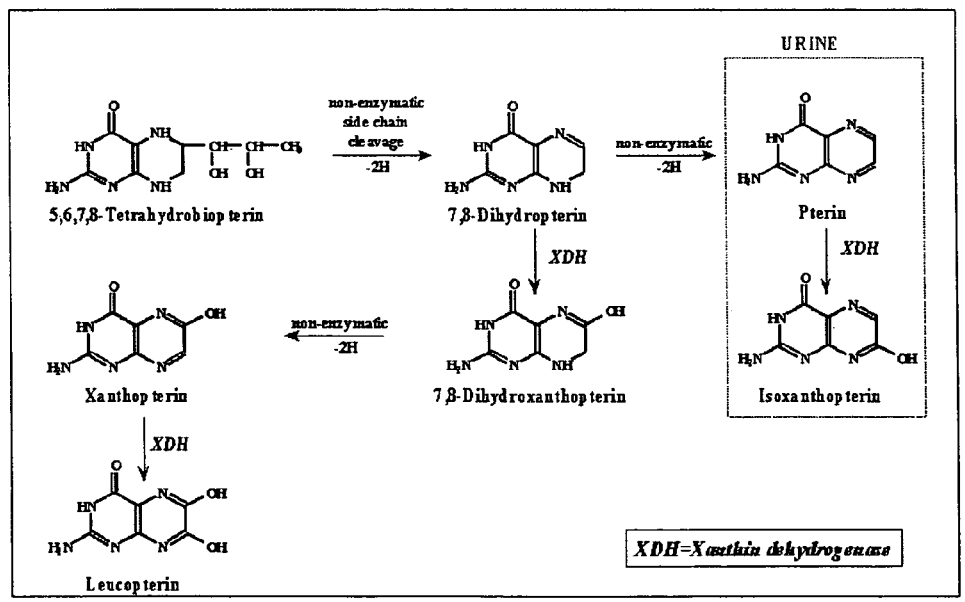
FIG. 2B is a schematic diagram showing the catabolism of tetrahydrobiopterin.

The invention stems from our discovery that inhibiting the synthesis of BH4 by interfering with the biological activity of any of the enzymes involved in the synthesis of BH4 (e.g., GTP cyclohydrolase (GTPCH), Sepiapterin Reductase (SPR), and Dihydropteridine reductase (DHPR), see FIG. 2A) results in prevention, treatment, and reduction in pain, i.e. analgesia. To this end, we show that the administration of 2,4 diamino 6-hydroxypyrimidine (DAHP), an inhibitor of GTPCH; Methotrexate (MTX), an inhibitor of DHPR; or N-acetyl-serotonin (NAS), an inhibitor of SPR, results in profound analgesia in various rat models of acute post-injury pain hypersensitivity, peripheral neuropathic and inflammatory pain, and without an effect on basal pain sensitivity, sedative effect, or gross disruption of motor function. This reduction in pain is mediated, at least in part, by the interference with or by a reduction in the activity of various enzymes for which BH4 is a key co-factor. Such enzymes include, for example, nitric oxide synthases and catecholamine synthetic enzymes. In addition, the reduction in the levels of BH4 may also reduce its release from cells in the nervous system and its direct actions, for example on neurotransmitter release or ion channel activity which may be mediated through BH4 binding to membrane bound receptors that modify neuronal function.

The methods of this invention are therefore useful for the diagnosis, treatment, reduction, or prevention of various forms of clinical pain, namely inflammatory pain, functional pain and neuropathic pain, whether acute or chronic. Exemplary conditions that may be associated with pain include, for example, soft tissue, joint, bone inflammation and/or damage (e.g., acute trauma, osteoarthritis, or rheumatoid arthritis), myofascial pain syndromes (fibromylagia), headaches (including cluster headache, migraine and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures). The present invention is also useful for the treatment, reduction, or prevention of musculo-skeletal pain (after trauma, infections, and exercise), neuropathic pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, metabolic disorders, hereditary conditions, infections, vasculitis and autoimmune diseases, central nervous system pain, such as pain due to spinal cord or brain stem damage, cerebrovascular accidents, tumors, infections, demyelinating diseases including multiple sclerosis, low back pain, sciatica, and post-operative pain. Conditions that are amenable to treatment according to the present invention are described in detail, for example, in U.S. Ser. No. 10/348,381 as well as U.S. Pat. Nos. 6,593,331 and 6,593,331, all of which are hereby incorporated by reference.

Briefly, we conducted a cluster analysis of changes in expression of developmentally- and peripheral nerve injury-regulated genes in the dorsal root ganglion using high-density oligonucleotide microarrays. Interestingly, we found that a particular cluster of genes was characterized by high levels of expression during development, down-regulation during adulthood, and induction following nerve injury. Such exemplary genes include DHPR (a member of the BH4 synthetic pathway).

A triplicate analysis of lumbar DRG microarrays three days post-axotomy (sciatic nerve transection) further revealed that three of the approximately 200 genes that were up-regulated were members of the BH4 synthetic pathway (e.g., GTPCH, SPR and DHPR). Their induction under such conditions was validated by Northern blot analysis, Northern slot blots, in situ hybridization, and Western blot analysis. We further confirmed that three of the four members of the BH4 synthetic pathway were up-regulated in primary sensory neurons after peripheral nerve injury in at least three models of peripheral neuropathic pain and that this was concomitant with an increase in BH4 levels in the dorsal root ganglion. Furthermore, using DAHP (a GTPCH inhibitor) as well as various other inhibitors of BH4 synthetic enzymes (e.g., NAS and methotrexate), we showed that inhibition of the BH4 synthetic pathway induces analgesia in numerous neuropathic pain models as well as in inflammatory pain and a post-injury pain hypersensitivity model. The analgesic action could be demonstrated after systemic delivery and intrathecal delivery. The latter indicates an action on the nervous system including the DRG and spinal cord. The degree of analgesia matched, or in the case of the spared nerve injury peripheral neuropathic pain model, was far greater than that achieved by any of the conventionally used analgesics, including morphine, gabapentin, carbamazepine, amytryptiline, and rofecoxib.

Therapeutic Agents
Inhibitors of the BH4 Pathway

BH4 is enzymatically synthesized de novo from guanosine 5'-triphosphate (GTP) via two intermediates, 7,8-dihydroneopterin triphosphate and 6-pyruvoyl tetrahydropterin (see FIG. 2A). According to the present invention, the administration of any agent that inhibits or modulates the biological activity of at least one, two, three, or more than three of any of the BH4 synthetic enzymes shown in FIG. 2A to reduce BH4 synthesis induces analgesia. Such enzymes include, for example, sepiapeterin reductase (SPR), Pyruvoyltetrahydropterin Synthase (PTPS), GTP cyclohydrolase (GTPCH), Pterin-4α-carbinolamine dehydratase, and dihydropteridine reductase (DHPR). The analgesic effect that results from the reduction in BH4 levels is caused, at least in part, by a reduction in the biological activity of enzymes for which BH4 is a co-factor and of membrane-bound receptors to which BH4 binds.

In this regard, BH4 is an essential cofactor of several enzymes (e.g., the hydroxylases of the three aromatic amino acids phenylalanine, tyrosine, and tryptophan; ether lipid oxidase; and the three nitric oxide synthase (NOS) isoenzymes, eNOS, iNOS, and nNOS) and therefore plays a key role in a number of biological processes, including neurotransmitter formation and signaling in pain pathways. Indeed, a number of enzymes that are regulated by BH4 have previously been involved in pain and include for example, NOS (Meller et al. (1992) *Neuroscience* 50:7-10; Minami et al., (1995) *Neurosci. Lett.* 201:239-242; Yamaguchi and Naito (1996) *Can. J. Anaesth.* 43:975-981; Aley et al., (1998) *J. Neurosci.* 18:7008-7014; Handy and Moore (1998) *Neuropharmacology* 37:37-43; Levy and Zochodne (1998) *Eur. J. Neurosci.* 10:1846-1855; Guhring et al. (2000) *J. Neurosci.* 20:6714-6720; Levy et al. (2000) *Eur J Neurosci* 12:2323-2332, tyrosine hydroxylase (Ma and Bisby (1999) *Neurosci Lett* 275:117-120; Lindqvist et al. (2000) *Muscle Nerve* 23:1214-1218) and tryptophan hydroxylase.

According to the present invention, an inhibitor of the BH4 pathway is any agent having the ability to reduce the production or the activity of BH4 by at least 10%, 20%, 30%, 40%, 50%, 60%, 70%, 80%, 90%, or 100% relative to an untreated control cell as determined by any standard method in the art, including those described herein. Alternatively, the inhibitor may treat, prevent, or reduce pain when administered to a mammal by at least 10%, 20%, 30%, 40%, 50%, 60%, 70%, 80%, 90%, or 100% relative to an untreated control. Such reduction or prevention in pain may be measured by any technique known in the art such as those described herein. Exemplary compounds that may be used according to this invention include DAHP, an inhibitor of GTPCH; MTX, an inhibitor of DHPR; NAS, an inhibitor of SPR; Tetrahydro-L-biopterin, L-Sepiapterin, 7,8-dihydro-L-Biopterin, 6,7-dimethyltetrahydropterin hydrochloride, N-acetyl-serotonin (NAS), N-Chloroacetylserotonin, N-Methoxyacetylserotonin, N-Chloroacetyldopamine, as well as any of the compounds identified by any of the screening methods of the invention. Other agents that may be used are described further below.

Optionally, the BH4 inhibitor may be a small molecule antagonist or an antisense to any of the BH4 synthetic enzymes. RNA interference (RNAi) may also be used to target the BH4 synthetic pathway as it provides a powerful method of gene silencing in eukaryotic cells including mammalian cells such as the primary sensory neurons of the present invention. The basic technique of RNAi involves introducing sequence-specific double-stranded RNA into neurons in order to generate a nonheritable, epigenetic knock-out of gene function that phenocopies a null mutation in the targeted gene. RNA interference has previously been described (O'Neil N J, et al., *Am J Pharmacogenomics* (2001): 45-53).

Alternatively, the analgesic agent may be a dominant negative protein or a nucleic acid encoding a dominant negative protein that interferes with the biological activity of BH4 or any of the BH4 synthetic enzymes. A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative BH4 synthetic enzyme may have mutation such that it no longer able to produce BH4.

According to this invention, the dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein to dorsal root ganglia or the spinal cord using, for example, microinjection techniques.

Inhibitors of GTP Cyclohydrolase I (GTPCH)

The rate-limiting enzyme in BH4 de novo biosynthesis is GTP cyclohydrolase I (GTPCH), which converts GTP to 7,8-dihydroneopterin triphosphate (see FIG. 2A). Over time, the accumulation of BH4 causes a feedback inhibition of GTPCH, in a reaction mediated by the GTPCH Feedback Regulatory Protein (GFRP). In the presence of phenylalanine, GFRP induces a feed-forward activation of GTPCH activity by enhancing GTP binding (Maita et al., (2002) *Proc. Natl. Acad. Sci. U.S.A.* 99: 1212-1217). However, in the presence of BH4, GFRP induces feedback inhibition of GTPCH enzyme activity (Yoneyama and Hatakeyama, (1998) *J. Biol. Chem.* 273:20102:20108); Yoneyama and Hatakeyama, (2001) *Protein Sci.* 10: 981-878) such that BH4 production is auto-inhibited.

Accordingly, any agent that inhibits GTPCH activity can efficiently reduce the production of BH4 and in turn, induce analgesia. GTPCH inhibitors may compete with the substrate GTP for binding to the catalytic center of the enzyme (FIG. 20). Alternatively, GTPCH inhibitors (for example BH4 analogs) may inhibit BH4 production by binding to the GTPCH/GFRP complex (FIG. 21) and thereby mimic the feedback inhibition of BH4. Although GFRP mRNA is abundant in brainstem neurons, it remains undetectable in dopamine neurons of the midbrain and in norepinephrine neurons of the locus coeruleus (Kapatos et al., (1999) *J. Neurochem.* 72: 669-675). Thus, the GFRP-dependency of GTPCH inhibitors may confer specificity and simultaneously avoid dopamine-related side effects.

Here, we have shown, for example, that the specific GTPCH inhibitor, 2,4-Diamino-6-hydroxypyrimidine (DAHP), induces analgesia in various neuropathic pain and inflammatory models (see FIGS. 8-13). DAHP-mediated inhibition of GTPCH is mediated by GFRP-dependent (at low concentrations) and GFRP-independent (at higher concentrations) mechanisms. Accordingly, DAHP mimics BH4 in its indirect mechanism of GTPCH inhibition at low concentrations. At higher concentrations DAHP competes with the physiological GTPCH-substrate, guanosine-triphosphate (GTP) for binding to the catalytic site (Xie et al., (1998) *J. Biol. Chem.* 273:21091-21098).

Biochemical and crystallographic studies on the interaction of GTPCH with GTP reveal that hydrogen bonds are formed between highly conserved amino acids found within the active site of GTPCH and the pyrimidine portion of guanine i.e. the nitrogen atoms at position 1, 2 and 3 and the oxygen at position 6, respectively (see FIG. 20) (Rebelo et al., (2003) *J. Mol. Biol.* 326: 503-516). This particular portion of the guanine structure exactly matches the pyrimidine structure of DAHP as well as a portion of the pteridine structure of tetrahydrobiopterin (BH4), which is the end product of the enzymatic cascade.

Figure 18:
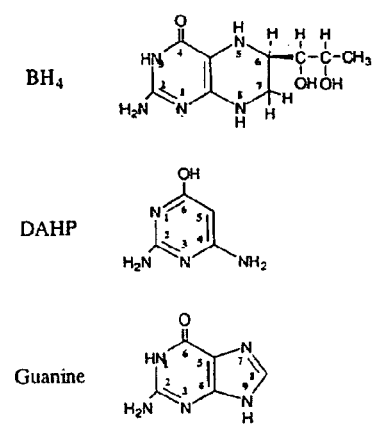
FIG. 18 shows the chemical structures of BH4, guanine, and DAHP

The structural homology between DAHP, guanine, and BH4 (see FIG. 18) indicates that it is the pyrimidine portion in these molecules that is likely to be crucial for binding to GTPCH. Analysis of various pyrimidine-molecules with modifications at these sites reveals that alterations at position 2, 4 and 6 are associated with a reduction or loss of GTPCH inhibitory activity (Yoneyama et al. (2001) *Arch. Biochem. Biophys.* 388: 67-73) (see FIG. 19). On the other hand, guanine itself (i.e. part of the physiological substrate) and guanine analogs with modifications at position 7 or 8 inhibit GTPCH with a higher potency (approximately 10 fold higher than DAHP) (Yoneyama et al., supra) (FIG. 19). Thus, drugs containing a 5-membered ring like guanine (thus also sharing higher similarity with BH4) have an increased inhibitory effect. Interestingly, BH4 is about 10 times more potent than guanine analogs (Yoneyama et al., supra) (FIG. 19) and 100 times more potent than DAHP, therefore suggesting that the side chain attached to C-6 of BH4 confers further potency and/or specificity. This is supported by the finding that an 6S-BH4 enantiomer and an analog of BH4 with no side chain at C-6 are more than one order of magnitude less effective than BH4 (Harada et al. (1993) *Science* 260:1507-1510). Accordingly, the potency of DAHP can be increased, for example, by increasing its structural similarity to BH4 while retaining substitutions or modifications that prevent its use as a cofactor for BH4-dependent enzymes (e.g., tyrosine, phenylalanine, and tryptophan hydroxylases; glycerol ether monooxygenases; and nitric oxide synthases (which utilize various N-alkyl and N-aryl-hydroxyguanidines such as N-(4-Chlorophenyl)N'-hydroxyguanidine as substrates for the production of nitric oxide (Moali et al. (2001) *Chem. Res. Toxicol.* 14:202-210; Renodon-Corniere et al., (1999) *Biochemistry* 38: 4663-8)).

In light of the above, the mammal being treated according to the present invention may be administered with a composition containing a compound having the formula:

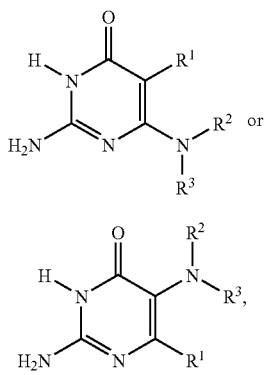

such that $R^1$ is a H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$. Each of $R^4$ and $R^5$ may be, independently, a H, $C_{1-6}$ alkyl, $C_{6-12}$ aryl, heteroaryl, $C_{1-4}$ alkaryl, or $C_{1-4}$ alkheteroaryl; $R^2$ may be a H, $C_{1-6}$ alkyl, $C_{6-12}$ aryl, heteroaryl, $C_{1-4}$ alkaryl, or $C_{1-4}$ alkheteroaryl; and $R^3$ may be a H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, where $R^6$ is a $C_{1-6}$ alkyl, $C_{6-12}$ aryl, heteroaryl, $C_{1-4}$ alkaryl, or $C_{1-4}$ alkheteroaryl, and each of $R^7$ and $R^8$ is, independently, a H, $C_{1-6}$ alkyl, $C_{6-12}$ aryl, heteroaryl, $C_{1-4}$ alkaryl, or $C_{1-4}$ alkheteroaryl.

Alternatively, $R^3$ may be as above and $R^1$ and $R^2$ together may be represented by

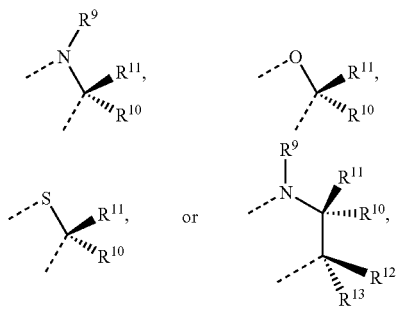

where the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Optionally, $R^3$ may be as above and $R^1$ and $R^2$ together may be represented by

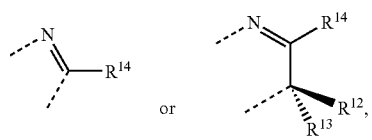

where the N of the $R^1/R^2$ linkage forms a bond to the pyrimidinone ring, each of $R^{12}$ or $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, such that each of $R^7$ and $R^8$ is, independently, a H, $C_1$-$C_6$ alkyl, $C_6$-$C_{12}$ aryl, heteroaryl, $C_1$-$C_4$ alkaryl, or $C_1$-$C_4$ alkheteroaryl.

As another alternative, $R^1$ and $R^2$ together may be represented by

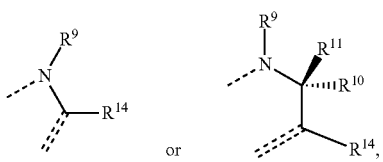

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing the $R^{14}$ and the nitrogen bearing $R^2$.

Optionally, the composition may have be a compound of formula (I), such that $R^1$ is a H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$. Accordingly, each of $R^4$ and $R^5$ may be, independently, a H, $C_{1-6}$ alkyl, $C_{6-12}$ aryl, heteroaryl, $C_{1-4}$ alkaryl, or $C_{1-4}$ alkheteroaryl, $R^2$ may be a H, $C_{1-6}$ alkyl, $C_{6-12}$ aryl, heteroaryl, $C_{1-4}$ alkaryl, or $C_{1-4}$ alkheteroaryl, and $R^3$ may be a H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2$ $NR^7R^8$, where R is a $C_{1-6}$ alkyl, $C_{6-12}$ aryl, heteroaryl, $C_{1-4}$ alkaryl, or $C_{1-4}$ alkheteroaryl and each of $R^7$ and $R^8$ may be, independently, a H, $C_{1-6}$ alkyl, $C_{6-12}$ aryl, heteroaryl, $C_{1-4}$ alkaryl, or $C_{1-4}$ alkheteroaryl.

If desired, the composition contains a compound of formula:

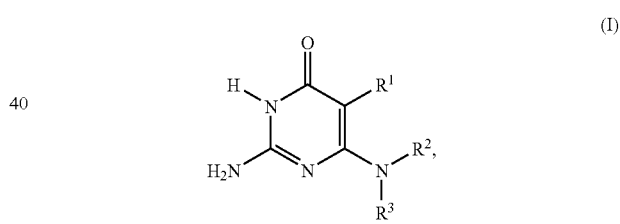

in which $R^1$ and $R^2$ together may be represented by

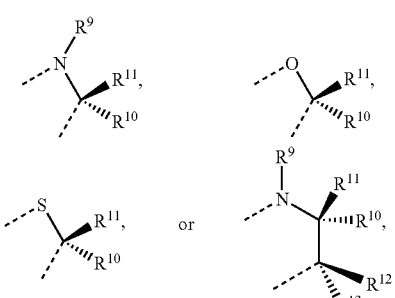

such that the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Alternatively, the composition contains a compound of formula:

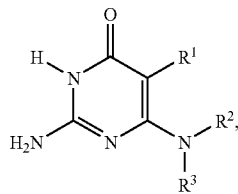

(I)

in which $R^3$ is as above and $R^1$ and $R^2$ together are represented by

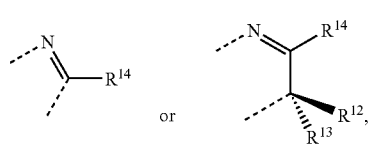

where the N of the $R^1/R^2$ linkage forms a bond to the pyrimidinone ring, each of $R^{12}$ and $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, where each of $R^4$, $R^7$ and $R^8$ is, independently, a H, $C_1$-$C_6$ alkyl, $C_6$-$C_{12}$ aryl, $C_1$-$C_4$ alkaryl, heteroaryl, or $C_1$-$C_4$ alkheteroaryl.

Alternatively, the composition contains a compound of formula:

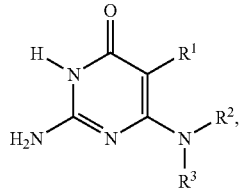

(I)

in which $R^1$ and $R^2$ together may be represented by

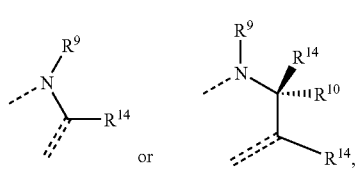

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$.

If the composition contains a compound of formula:

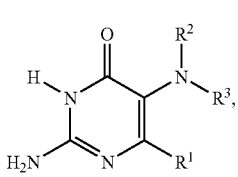

(II)

$R^1$ and $R^2$ together may be represented by

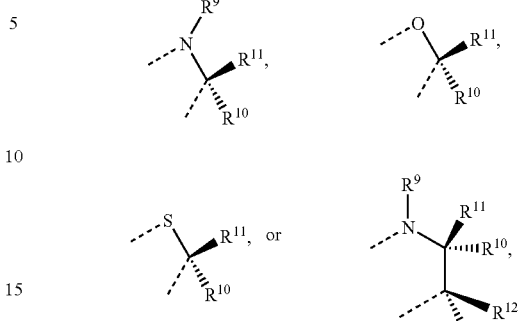

where the N, O, or S of the $R^1/R^2$ linkage forms a bond to the pyrimidinone ring and each of $R^9$, $R^{10}$, $R^{11}$, $R^{12}$, and $R^{13}$ is, independently, a H, $C_{1-6}$ alkyl, $C_{6-12}$ aryl, heteroaryl, $C_{1-4}$ alkaryl, or $C_{1-4}$ alkheteroaryl.

Alternatively, the composition contains a compound of formula:

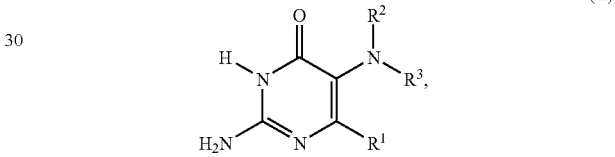

(II)

in which $R^3$ is as above and $R^1$ and $R^2$ together are represented by

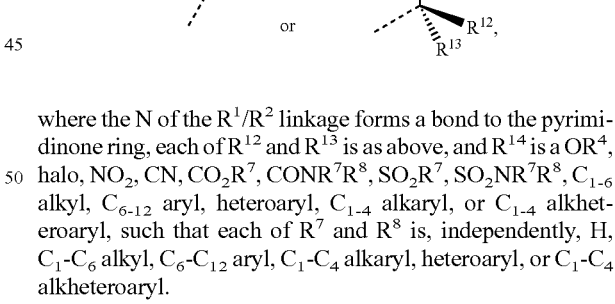

where the N of the $R^1/R^2$ linkage forms a bond to the pyrimidinone ring, each of $R^{12}$ and $R^{13}$ is as above, and $R^{14}$ is a $OR^4$, halo, $NO_2$, CN, $CO_2R^7$, $CONR^7R^8$, $SO_2R^7$, $SO_2NR^7R^8$, $C_{1-6}$ alkyl, $C_{6-12}$ aryl, heteroaryl, $C_{1-4}$ alkaryl, or $C_{1-4}$ alkheteroaryl, such that each of $R^7$ and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl.

Optionally, the composition may contain a compound of formula:

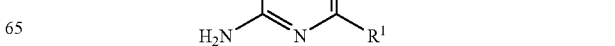

(II)

in which $R^1$ and $R^2$ together are represented by

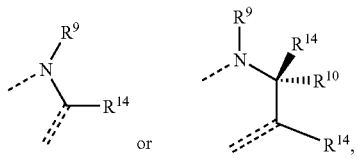

where the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$.

Exemplary compounds that may be contained within the composition of the invention include, for example:

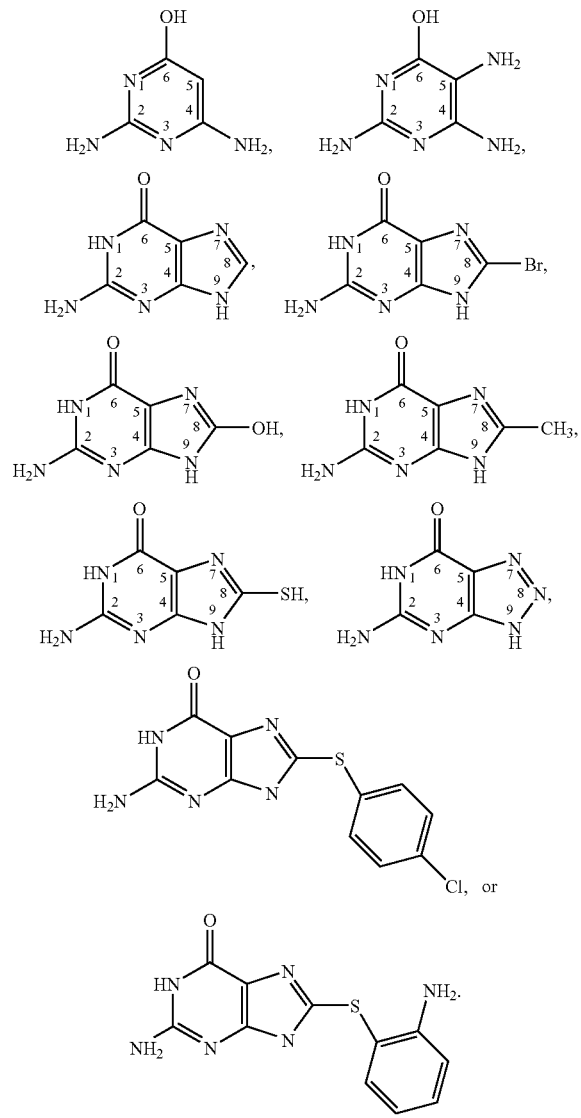

These compounds are shown in FIG. 19.

Furthermore, the composition of the invention may contain a compound having the formula:

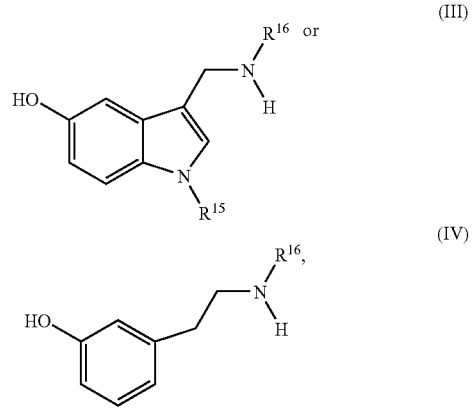

in which $R^{15}$ is a H, $C_{1-6}$ alkyl, $C_{6-12}$ aryl, heteroaryl, $C_{1-4}$ alkaryl, or $C_{1-4}$ alkheteroaryl and $R^{16}$ is a H, $C_{1-6}$ alkyl, $C_{6-12}$ aryl, heteroaryl, $C_{1-4}$ alkaryl, $C_{1-4}$ alkheteroaryl, $CO_2R^{17}$, $CONR^{18}R^{19}$, $SO_2R^{17}$, or $SO_2NR^{18}R^{19}$. $R^{17}$ may be a $C_{1-6}$ alkyl, $C_{6-12}$ aryl, heteroaryl, $C_{1-4}$ alkaryl, or $C_{1-4}$ alkheteroaryl and each of $R^{18}$ and $R^{19}$ may be, independently, a H, $C_{1-6}$ alkyl, $C_{6-12}$ aryl, heteroaryl, $C_{1-4}$ alkaryl, or $C_{1-4}$ alkheteroaryl.

Further exemplary compounds include Tetrahydro-L-biopterin (BH4.2HCl, a reduced pterin that is a noncompetitive inhibitor of GTP cyclohydrolase I with a Ki of 15.7 µM); L-Sepiapterin (a reduced pterin that is 12 times more potent than oxidized pterins as a GTP cyclohydrolase I inhibitor and has an IC50 of 12.7±1.8 µM); 7,8-dihydro-L-Biopterin (BH2, a metabolic end product of GTP cyclohydrolase I in vitro, which functions as a noncompetitive inhibitor of GTP cyclohydrolase I (Ki of 14.4 µM) and is approximately 12 times more potent as an inhibitor than oxidized pterins, folates, and aminopterins); and 6,7-dimethyltetrahydropterin hydrochloride (a noncompetitive inhibitor of GTP cyclohydrolase I (IC50 of 76 to 112 µM)). As discussed above, the inhibition of GTPCH may also be accomplished using inhibitors that act on GTPCH in a GFRP-independent GTP competitive fashion (e.g., guanine derivatives as shown in FIG. 19 and as described above).

Activators of GTPCH Feedback Regulatory Protein (GFRP)

GFRP is the endogenous inhibitor of BH4 synthesis by GTPCH. The binding of GFRP to GTPCH is, itself, a BH4-dependent event, making GFRP a negative feedback regulator of BH4 production. It has recently been discovered that DAHP, a molecule that is structurally similar to BH4, binds to GFRP and promotes GTPCH inhibition (Kolinsky et al., *J. Biol. Chem.*, Manuscript M405370200, Jul. 29, 2004). Thus, molecules that mimic the actions of BH4 and/or DAHP at GFRP by enhancing the binding of GFRP to GTPCH and inhibiting the production of BH4 are useful in the methods of this invention. Alternatively, molecules that facilitate the binding of GFRP and GTPCH, but not through a binding at the BH4 site on GFRP are also useful. Such molecules include, for example, bi-functional antibodies or cross-linking agents.

Inhibitors of Sepiapterin Reductase

Figure 15:
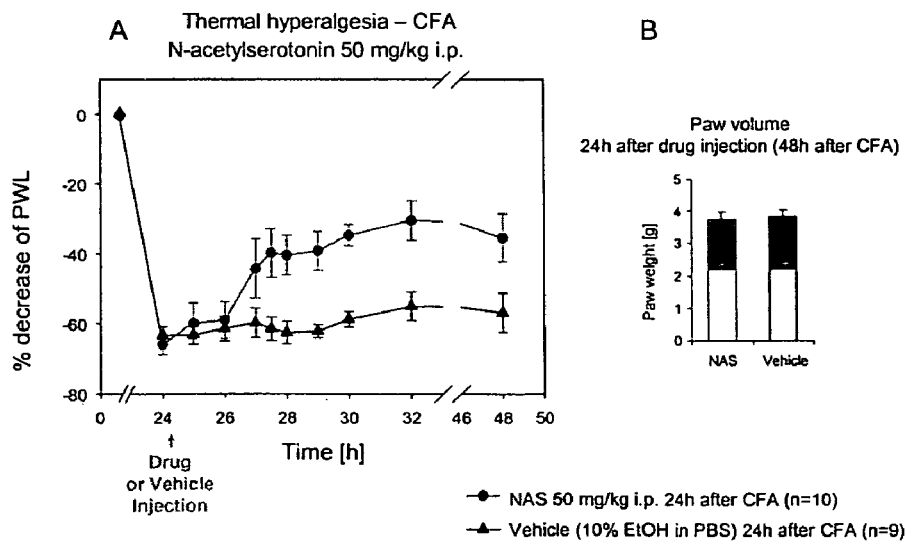
FIGS. 15A and 15B show the effect of the sepiapterin reductase inhibitor, N-acetyl-serotonin (NAS) on thermal hyperalgesia in the CFA model. The paw withdrawal latency (PWL) to radiant heat (Hargreaves test) is a measure for the heat sensitivity. NAS treatment (single dose of 50 mg/kg i.p.) was started 24 hours after CFA injection into the hindpaw. Data are presented as percentage change of the PWL compared with the PWL of the non-inflamed contralateral paw.
Figure 16:
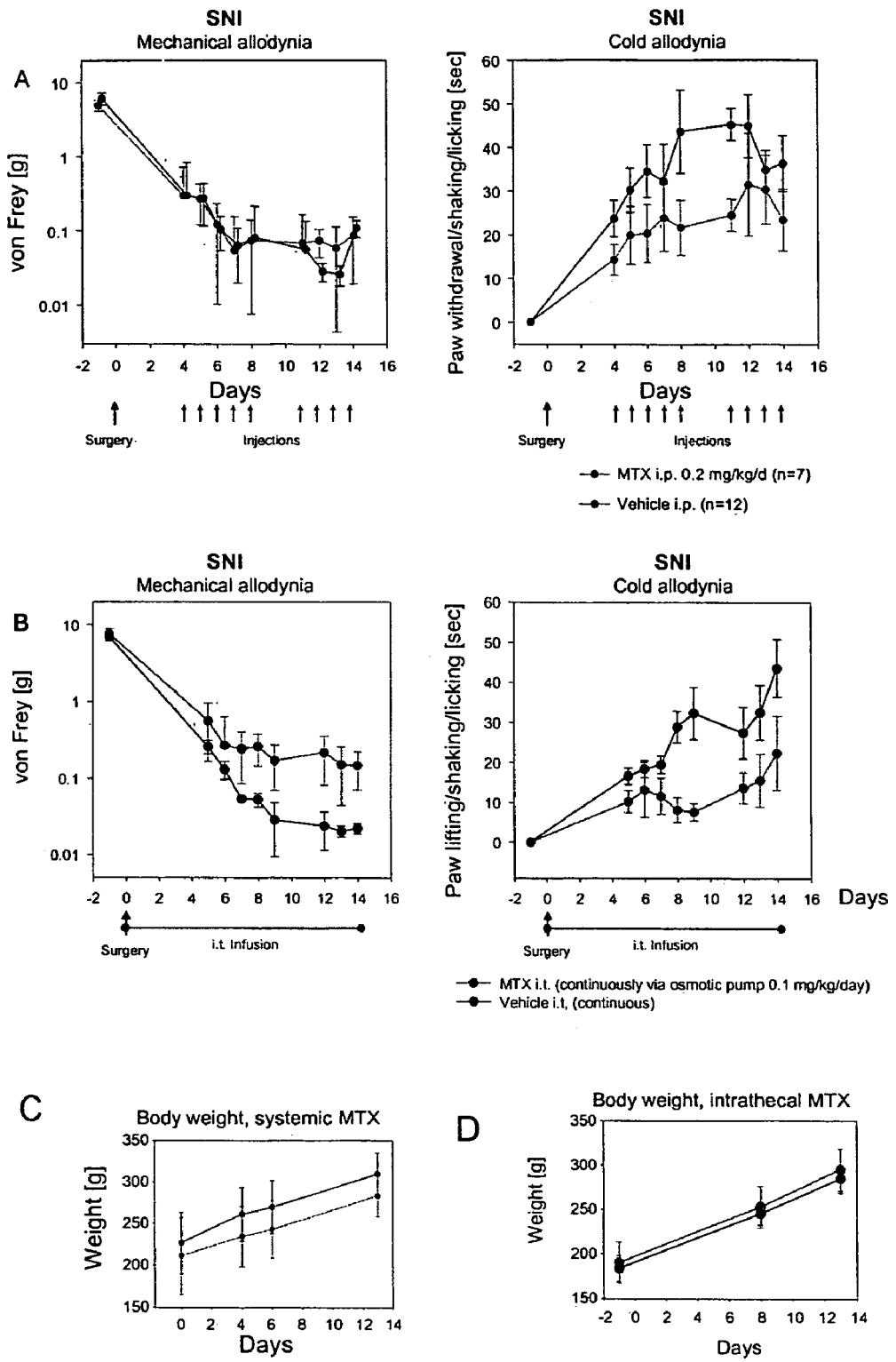
FIGS. 16A-16D show the effects of systemic (16A) and intrathecal (16B) treatment with methotrexate (MTX) on the nociceptive behavior in the SNI model of neuropathic pain.

Sepiapterin Reductase (SPR) functions as the final synthetic enzyme in the BH4 pathway. Here, we show that NAS (50 mg/kg i.p., an inhibitor of SPR, produces analgesia in a model of inflammatory pain (FIGS. 15A and 15B). Other sepiapterin reductase inhibitors with increased potency include N-Chloroacetylserotonin, N-Methoxyacetylserotonin, and N-Chloroacetyldopamine.

Inhibitors of Dihydropteridine Reductase (DHPR)

The BH4 salvage arm, which involves DHPR, allows a recycling of oxidized BH4 without de novo synthesis. The inhibition of DHPR, which is upregulated in DRGs and the spinal cord following nerve injury, induces analgesia by inhibiting the recycling of BH4 from BH2. For example, the administration of methotrexate (MTX, also known as amethopterin hydrate (0.1 mg/kg/d as continuous intrathecal infusion or 0.2 mg/kg i.p. once daily) results in pain reduction without directly affecting BH4 de novo synthesis (see FIGS. 16A-16F). MTX is an inhibitor of dihydrofolate reductase and has been approved for use in humans as an immunosuppressant. It is typically used at low dosages for the treatment of rheumatoid arthritis (Weinstein et al. (1985) *Am J Med* 79: 331-7, Williams et al. (1985) *Arthritis Rheum;* 28: 721-30, Weinblatt et al. (1985) *N Engl J Med* 312: 818-22, Hoffmeister et al. (1983) *Am J Med* 75: 69-73, Giannini et al. (1992) *N Engl J Med* 326: 1043-9). While systemically administered MTX primarily reaches peripheral targets and DRGs, MTX delivered spinally targets the spinal cord and DRGs. Systemically administered MTX (at low doses) does not penetrate the blood brain barrier because it is a substrate for ATP-binding cassette (ABC) transporters (probenicid-sensitive multi-drug resistance protein (MRP) 1-3). Consequently, systemic treatment with MTX may require the co-administration with probenicid or other inhibitors of MRPs or organic anion transporters to ensure that MTX reaches the spinal cord and brain.

If desired, analgesia may be induced by simultaneously blocking both parts of the BH4 pathway, namely the biosynthesis and the salvage pathways, to achieve an additive effect. For example, the reduction in pain may be significantly enhanced by blocking BH4 synthesis by simultaneously inhibiting GTPCH using DAHP and DHPR using methotrexate (or other DHPR inhibitors that achieve higher concentration in the central nervous system).

Inhibitors of Pterin-4α-carbinolamine dehydratase (PCD)

Quinoid dihydropterin products are strong inhibitors of the Pterin-4α-carbinolamine dehydratase (PCD) (having KI's of about one half of their respective Km's) and may therefore be used according to the present invention. (Rebrin et al. (1995) *Biochemistry* 34: 5801-10).

Second Therapeutic Agents

The composition of the present invention may be administered either alone or in combination with a second therapeutic agent, such as an analgesic agent used in the treatment of nociception, inflammatory, functional or neuropathic pain. According to this invention, the second therapeutic agent may or may not produce a therapeutic effect when administered on its own, but results in such an effect (e.g., pain reduction) when administered with the composition of the invention.

Exemplary analgesic agents include, nonsteroidal anti-inflammatory agents (NSAIDs) (e.g. rofexocib, celecoxib, valdecoxib, paracoxib, salicylic acid, acetominophen, diclofenac, piroxican indomethacin, ibuprofen, and naproxen), opioid analgesics (e.g., propoxyphene, meperidine, hydromoiphone, hydrocodone, oxycodone, morphine, codeine, and tramodol), NMDA antagonist analgesics (e.g., 2-piperdino-1 alkanol derivatives, ketamine, dextormethorphan, eliprodil, or ifenprodil), anesthetic agents (e.g., nitrous oxide, halothane, fluothane) local anesthetics (lidocaine, etidocaine, ropivacaine, chloroprocaine, sarapin, and bupivacaine), benzodiazepines (diazepam, chlordiazepoxide, alprazolam, and lorazepam), capsaicin, tricyclic antidepressants (e.g., amitriptyline, perphanazine, protriptyline, tranylcypromine, imipramine, desimipramine, and clomipramine), skeletal muscle relaxant analgesics (flexeril, carisoprodol, robaxisal, norgesic, and dantrium), migraine therapeutic agents (e.g., elitriptan, sumatriptan, rizatriptan, zolmitriptan, and naratriptan), anticonvulsants (e.g., phenytoin, lamotrigine, pregabalin, carbamazepine, oxcarbazepine, topiramate, valproic acid, and gabapentin), baclofen, clonidine, mexilitene, diphenyl-hydramine, hydroxysine, caffeine, prednisone, methylprednisone, decadron, paroxetine, sertraline, fluoxetine, tramodol, ziconotide, levodopa.

If desired, the mammal being treated may be administered with more than one agent that inhibits the production of BH4. Optionally, the composition of the invention may contain more than one such inhibitor. Alternatively, the mammal may further be administered with specific inhibitors of enzymes that function downstream of BH4, in addition to the composition of the invention. Such inhibitors are described below.

BH4-Dependent Enzymes

BH4 is an essential cofactor of several enzymes, i.e. the hydroxylases of the three aromatic amino acids phenylalanine, tyrosine, and tryptophan; ether lipid oxidase; and of the three nitric oxide synthase (NOS) isoenzymes. Thus, BH4 plays a key role in a number of biological processes including neurotransmitter formation and signaling pathways.

Nitric oxide (NO) is released from nociceptive neurons following NMDA receptor stimulation and diffuses back to the presynaptic neuron where it causes further glutamate release by stimulating the guanylyl cyclase/cGMP/cGMP dependent kinase pathway. Furthermore, NO modulates excitability of the postsynaptic neuron. Inhibitors of NO synthase, such as L-NAME ($N^G$-Nitro-L-arginine-methyl ester), reduce inflammatory hyperalgesia and neuropathic allodynia in various models and accordingly, may be administered with or admixed in the composition of the invention. Given that drugs, which block the activity of all NOS enzymes, are generally more effective than specific inhibitors of either neuronal NOS (nNOS) or inducible NOS (iNOS), both enzymes are most likely involved in pain. nNOS is constitutively expressed in neurons and upregulated after peripheral nociceptive stimulation. iNOS is upregulated in the spinal cord after peripheral nociceptive stimulation particularly in glial cells and produces much higher NO levels than nNOS. Although endothelial nitric oxide synthase (eNOS) is primarily expressed in endothelial cells, studies in knockout mice have shown that this enzyme also contributes to pain modulation. All of these enzymes are dependent on BH4, employing it as a cofactor. Inhibitors of the NOS pathway that may be used to induce analgesia include inhibitors of NOS-1 (nNOS) such as N-Methyl-L-arginine (M 7033), N-Nitro-L-arginine (N 5501), 7-Nitroindazole (N 7778), 1-(2-Trifluoromethylphenyl) imidazole (T 7313), L-Thiocitrulline, S-Methyl-L-thiocitrulline (M 5171); inhibitors of NOS-2 (iNOS), such as Aminoguanidine (A 8835, A 7009), S-Benzylisothiourea (B 9138), 1-(2-Trifluoromethylphenyl)imidazole (T 7313), L-N6-(1-Iminoethyl)lysine (I 8021), and 1400W (W 4262); and inhibitors of NOS-3 (eNOS) include N-Methyl-L-arginine (M 7033), N-Nitro-L-arginine (N 5501), N-Iminoethyl-L-ornithine (I 8768), and 7-Nitroindazole (N 7778).

Tyrosine hydroxylase catalyses the first step in cathecholamine synthesis, i.e., the production of dopamine from the amino acid tyrosine in a reaction that requires the presence of BH4. Tryptophan hydroxylase is the key enzyme in serotonin synthesis. Noradrenaline and serotonin act as neurotransmitters in descending inhibitory neurons arising from the locus coeruleus and nucleus raphe magnus, respectively. Reduction of co-factor availability for these enzymes may therefore result in an increase of pain. To overcome this potential disadvantage, the composition of the present invention may be administered in combination with a 5HT receptor agonist and/or a centrally acting alpha receptor agonist such as clonidine. Various 5HT-1 agonists have antinociceptive effects when administered alone such as the 5-HT-1B agonists m-trifluoromethylphenyl-piperazine (TFMPP) and 7-trifluoromethyl-4(4-methyl-1-piperazinyl)-pyrrolo(1,2-1a)quinoxaline (CGS 12066B) (Alhaider et al., (1993) *J Pharmacol Exp Ther.* 265:378-85) or the 5HT-2A agonist, FR143166 (Ochi et al. (2002) *Eur J Pharmacol.* 452:319-24). Alternatively, a potential decrease of serotonin and/or noradrenaline synthesis may be outweighed by combination treatment with a reuptake inhibitor such as a tricyclic antidepressant (e.g. amitriptyline) or a selective serotonin reuptake inhibitor (e.g. paroxetine, see above).

Direct Effects of BH4

In addition to its co-factor function, the R enantiomer of BH4 (6R-BH4) exhibits various direct effects on neurons when delivered via microdialysis to certain regions of the brain. For example, 6R-BH4 increases the release of dopamine in the striatum. Given that these effects persist in the presence of a tyrosine hydroxylase inhibitor (alpha-methyl-p-tyrosine), it is probably not caused by an increase of dopamine synthesis (Koshimura et al. (1995) *J Neurochem.* 65: 827-30). 6R-BH4 also increases the release of other neurotransmitters such as acetylcholine in the hippocampus (Ohue et al. (1991) *Neurosci Lett.* 128:93-6) and glutamate and serotonin in the striatum and frontal cortex (Mataga et al. (1991) *Brain Res.* 551: 64-71). The neurotransmitter releasing effects of BH4 are inhibited with a calcium channel antagonist (Koshimura et al. (1995) *J Neurochem.* 65:827-30). The addition of 6R-BH4 to microdialysis perfusion fluid also increases calcium currents in the motor nucleus of the vagus in rats whereas the addition of L-DOPA or the nitric oxide donor Sin-1 has no effect, therefore suggesting that these effects are independent of tyrosine hydroxylase or NOS activity, respectively (Shiraki T et al., (1996) *Biochem Biophys Res Commun.* 221: 181-5). The S-enantiomer of BH4 (6S-BH4) or the precursor sepiapterin has no effect on neurotransmitter release. 6R-BH4 may therefore act through a specific "BH4-receptor." However, such a membrane bound extracellular binding site for BH4 has not yet been identified/characterized.

Screening for Potential Novel BH4 Binding Sites

The results described herein suggest the existence of a novel membrane bound or intracellular BH4 binding molecule that functions as a BH4 target protein. Although the characteristics of BH4 as a coenzyme are well described in the literature its binding to other proteins and its transport mechanisms have not been investigated. Novel proteomic approaches have been developed that allow for a high throughput screening of binding sites of small molecules such as BH4. Large-scale protein chips i.e., two-dimensional displays of individual proteins have been constructed by immobilizing large numbers of purified proteins on microplates. They are used, for example, to assay protein-protein interactions, drug-target or enzymes-substrate interactions. Generally they require an expression library, cloned into *E. coli*, yeast, or other similar expression systems from which the expressed proteins are then purified, and immobilized. Any suitable protein purification method known in the art may be used including, for example, a His-tag. Cell free protein transcription/translation such as ribosome display is an alternative for synthesis of proteins. Phage or yeast display libraries may also be used.

Binding of BH4 may be detected directly by labeling BH4 for example with tritium what has been described previously (Werner et al., *Biochem. J.* 604: 189-193, 1994) or with biotin which may be coupled to the primary amino group of BH4. Incorporation of tritium may be achieved in a cell based system with over-expression of the synthetic enzymes and [$^3$H]-labeled GTP as the substrate (Werner et al., 1994). BH4 can also be chemically labeled with tritium using the commercially available 6R-BH4 hydrochloride as template. As an alternative to BH4 labeling, its binding to novel targets might also be detected by using a labeled capturing molecule e.g., a peptide containing the BH4 binding site of one of the enzymes that bind BH4 as cofactor or a BH4 antibody. Label-free detection methods, including mass spectrometry, surface plasmon resonance and atomic force microscopy are also available and avoid alteration of the ligand. In addition to large scale protein arrays two-dimensional gel electrophoresis of tissue or cell protein extracts of the dorsal horn and DRGs can be used to screen for novel binding sites. The gel is then blotted onto PVDF membranes and exposed to labeled BH4. Positive protein spots can be analyzed by mass fingerprinting using matrix-assisted laser desorption ionization time of flight mass spectrometry (MALDI-TOF MS).

Diagnosis of Pain or a Peripheral Nerve Lesion Using the BH4 Pathway

According to this invention, pain or a traumatic, metabolic or toxic peripheral nerve lesion may be diagnosed in a mammal by measuring the levels of BH4, BH4 intermediates, BH4 precursors, or BH4 metabolites in a biological sample obtained from a mammal (e.g., serum, plasma, urine, cerebrospinal fluid, synovial fluid, tissue exudate, or tissue sample). Pain or a peripheral nerve lesion is diagnosed if an increase in such levels relative to a control (at least 10%, 20%, 30%, 40%, 50%, 60%, 70%, 80%, 90%, 95%, 100%, or more than 100% relative to control) is detected using any standard method known in the art. Alternatively, pain or a peripheral nerve lesion may be diagnosed if an increase in the levels or activity of any of the BH4 synthetic enzymes is detected. Desirably, such increase is at least 10%, 20%, 30%, 40%, 50%, 60%, 70%, 80%, 90%, 95%, 100%, or more than 100% relative to control conditions. According to this invention, the BH4 pathway serves as a biomarker of nerve injury and pain.

The present invention further provides a kit for diagnosing pain or a traumatic, metabolic or toxic peripheral nerve lesion in mammal involving the measurement of BH4, its precursors and intermediates (e.g., 7,8-dihydroneopterin triphosphate neopterin and 6-pyruvoyl tetrahydropterin) or metabolites (e.g., pterin, biopterin, 7,8 dihydropterin, 7,8 dihydroxanthopterin, xanthopterin, isoxanthopterin, or leucopterin) in a biological sample, such as serum, plasma, urine, cerebrospinal fluid, synovial fluid, tissue exudates, and tissue samples. For example, the invention may include an antibody specific for any one of the above compounds (e.g., biopterin or neopterin) and instructions to diagnose pain in a mammal. In this regard, serum may be isolated from a mammal in which a condition associated with the symptom of pain is tested or a traumatic, metabolic or toxic peripheral nerve lesion is suspected, and subjected to an ELISA or RIA assay using an antibody of the invention. Pain is diagnosed in the mammal if the serum level of BH4 in the mammal's serum (as detected by the antibody) is increased relative to the BH4 levels in a control serum sample. The diagnosis of pain, a subtype of pain, or a peripheral nerve lesion is in a mammal if the levels of the compound being measured in the biological sample obtained from the mammal is increased by at least 10%, 20%, 30%, 40%, 50%, 60%, 70%, 80%, 90%, 100%, or more than 100% relative to the level of the same compound in a control biological sample.

Pain Models

Various models test the sensitivity of normal animals to intense or noxious stimuli (physiological or nociceptive pain). These tests include responses to thermal, mechanical, or chemical stimuli.

Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. In such models, the end points include latency to a painful response, the duration of the response, vocalization, and licking of the paw. Immersion in cold water, acetone evaporation, or cold plate tests may also be used to test cold pain responsiveness.

Tests involving mechanical stimuli typically measure the threshold for eliciting a withdrawal reflex of the hindpaw to graded strength monofilament von Frey hairs (the outcome measure being the force of the filament required to elicit a reflex) or to a sustained pressure stimulus to a paw (e.g., the Ugo Basile analgesiometer). The duration of a response to a standard pinprick may also be measured.

When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured. The outcome measures include vocalization, licking of the paw, writhing, or spontaneous flexion.

In addition, various tests assess pain sensitization by measuring changes in the excitability of the peripheral or central components of the pain neural pathway. In this regard, peripheral sensitization (i.e. changes in the threshold and responsiveness of high threshold nociceptors) can be induced by repeated heat stimuli as well as the application or injection of sensitizing chemicals (e.g. prostaglandins, bradykinin, histamine, serotonin, capsaicin, mustard oil). The outcome measures are thermal and mechanical sensitivity in the area of application/stimulation using the techniques described above in behaving animals, or alternatively, electrophysiological measurements of single sensory fiber receptive field properties either in vivo or using isolated skin nerve preparations. The electrophysiological, neurochemical or cell biological properties of sensory neurons can also be used to study these parameters indirectly (e.g., recordings from isolated sensory neurons (e.g., dorsal root ganglion neurons in culture), activation of signal transduction pathways by sensitizing stimuli (e.g., protein kinase C or A), or measurements of receptor or ion channel phosphorylation). Central sensitization (i.e. changes in the excitability of neurons in the central nervous system induced by activity in peripheral pain fibers) can be induced by noxious stimuli (e.g., heat), chemical stimuli (i.e. injection or application of chemical irritants such as capsaicin, mustard oil, or formalin), or electrical activation of sensory fibers. The outcome measures may be behavioral (i.e. thermal and mechanical responsiveness outside of the area of application, that is the area of secondary hyperalgesia, or tactile allodynia (pain responses to normally innocuous tactile stimuli)), electrophysiological (i.e. receptive field properties of single central neurons), neurochemical (i.e. activation of signal transduction pathways in central neurons (e.g., ERK, p38, CREB, immediate early genes such as c-fos, kinases, PKC, PKA, or src) or phosphorylation of receptors or ion channels such as NMDA or AMPA receptors). Functional imaging techniques may also be used to assess changes in the patterns of activation.

Various pain tests have also been developed to measure the effect of peripheral inflammation on pain sensitivity (Stein et al., *Pharmacol. Biochem. Behav.* (1988) 31: 445-451; Woolf et al., *Neurosci.* (1994) 62: 327-331). The inflammation may be produced by injection of an irritant (e.g., complete Freund's adjuvant, carrageenan, turpentine, and croton oil) into the skin, subcutaneously, into a muscle, into a joint, or into a visceral organ. Alternatively, the generation of a controlled UV light burn and ischemia or the administration of cytokines or inflammatory mediators such as lipopolysaccharide (LPS) or nerve growth factor (NGF) can also mimic the effects of inflammation. Following the induction of inflammation, the outcome measures may include changes in behavior (e.g., thermal and mechanical sensitivity (as discussed above), weight bearing, visceral hypersensitivity (e.g., inflation of balloons in bladder or bowel), spontaneous locomotor activity, or performance in more complex behaviors such as place preference tasks), in electrophysiology (e.g., in vivo and in vitro recordings from primary sensory neurons and central neurons with particular attention to changes in receptive field properties, excitability, or synaptic input), in neurochemistry (e.g., changes in the expression and distribution of transmitters, neuropeptides, and proteins in primary sensory and central neurons, activation of signal transduction cascades, expression of transcription factors, and phosphorylation of proteins in neurons), and imaging techniques to detect changes in neural activity.

Additionally, various tests assess peripheral neuropathic pain using lesions of the peripheral nervous system. One such example is the "axotomy pain model," for example, which involves the complete transection of a peripheral nerve and in which one or a plurality of peripheral nerve fibers is severed, either by traumatic injury or experimental or surgical manipulation (Watson, *J. Physiol.* (1973) 231:41). Other similar tests include the SNL test which involves the ligation of a spinal segmental nerve (Kim and Chung *Pain* (1992) 50: 355), the Seltzer model involving partial nerve injury (Seltzer, *Pain* (1990) 43: 205-18), the spared nerve injury (SNI) model (Decosterd and Woolf, *Pain* (2000) 87:149), chronic constriction injury (CCI) model (Bennett (1993) *Muscle Nerve* 16: 1040), tests involving toxic neuropathies such as diabetes (streptozocin model), pyridoxine neuropathy, taxol, vincristine, and other antineoplastic agent-induced neuropathies, tests involving ischaemia to a nerve, peripheral neuritis models (e.g., CFA applied peri-neurally), models of post-herpetic neuralgia using HSV infection, and compression models. In all of the above tests, outcome measures may be assessed, for example, according to behavior (e.g., thermal and mechanical sensitivity as above, weight bearing, spontaneous activity, or performance in more complex behaviors such as place preference tasks), electrophysiology (e.g., in vivo and in vitro primary sensory neurons and central neurons with particular attention to changes in membrane excitability, spontaneous activity, receptive field properties, and synaptic input), neurochemistry (e.g., expression and distribution of transmitters, neuropeptides and proteins in primary sensory and central neurons, activation of signal transduction cascades, expression of transcription factors, and phosphorylation of proteins in neurons), and imaging techniques to detect changes in neural activity. Furthermore, several pain tests that mimic central neuropathic pain involve lesions of the central nervous system including, for example, spinal cord injury (e.g., mechanical, compressive, ischemic, infective, or chemical). In these particular tests, outcome measures are the same as those used for peripheral neuropathic pain.

Various features of pain are shared between the above models. In this respect, physiological pain is characterized by a high threshold to mechanical and thermal stimuli and rapid transient responses to such stimuli. Inflammatory and neuropathic pain are characterized by displays of behavior indicating either spontaneous pain (measured by spontaneous flexion, vocalization, biting, or even self mutilation), abnormal hypersensitivity to normally innocuous stimuli (allodynia), and an exaggerated response to noxious stimuli (hyperalgesia).

Measurement of Pain

Thermal and mechanical threshold sensitivity may be measured quantitatively, for example, in ° C., force in grams or Newtons, or alternatively, as a measure of time to respond. For thermal pain thresholds, the temperature of a hot stimulus >40° C. or a cold stimulus (<15° C.) that elicits a flexion withdrawal response is typically measured. For mechanical thresholds the force of a punctate mechanical stimulus (<100 g) that elicits a flexion withdrawal response is measured. The reduction in the latency of response to the stimulus, that is the length of time the animal takes to respond, can also be measured (typically <10 seconds). The actual values depend on the nature of the test and the area of the body stimulated. One way of testing an increase in pain sensitivity is to repeatedly apply a stimulus close to threshold levels and look for an increase in the proportion of positive responses to this fixed stimulus. For pain responsiveness, the measurement is the duration or magnitude of a response such as the amount of time an animal holds its limb in a flexed position after a pinprick or a hot or cold stimulus.

Screening Assays

The present invention provides screening methods to identify compounds that can inhibit the production or action of BH4. Useful compounds include any agent that can inhibit the biological activity or reduce the cellular level of BH4 or at least one or more than one of any one of the enzymes shown in FIG. 2A. Such enzymes include, for example, GTP cyclohydrolase (GTPCH), Pyruvoyltetrahydropterin (PTPS), Sepiapterin Reductase (SPR), and Dihydropteridine Reductase (DHPR). As discussed above, we have shown that DAHP, NAS, and methotrexate are useful to treat, reduce, or prevent pain. Using such agents as lead compounds, for example, the present screening methods allow the identification of novel, specific inhibitors of the BH4 synthetic pathway that function to induce analgesia. The method of screening may involve high-throughput techniques.

A number of methods are available for carrying out such screening assays. According to one approach, candidate compounds are added at varying concentrations to the culture medium of cells expressing one or more of the BH4 synthetic enzymes. Gene expression of the BH4 synthetic enzymes is then measured, for example, by standard Northern blot analysis (Ausubel et al., supra), using any appropriate fragment prepared from the nucleic acid molecule of the BH4 synthetic enzyme as a hybridization probe or by real time PCR with appropriate primers. The level of gene expression in the presence of the candidate compound is compared to the level measured in a control culture lacking the candidate molecule. If desired, the effect of candidate compounds may, in the alternative, be measured at the level of BH4 production using the same general approach and standard immunological techniques, such as Western blotting, immunoprecipitation, or immunoassay with an antibody specific to the BH4 synthetic enzyme or for BH4 (or its intermediaries or metabolites). For example, immunoassays may be used to detect or monitor the level of BH4 or GTPCH. Polyclonal or monoclonal antibodies which are capable of binding to BH4, BH4 precursors, or BH4 metabolites may be used in any standard immunoassay format (e.g., ELISA or RIA assay) to measure the levels of BH4 or its precursors or metabolites. BH4 or its precursors or metabolites can also be measured using mass spectroscopy, high performance liquid chromatography, spectrophotometric or fluorometric techniques, or combinations thereof. Total biopterin (BH1, BH2, and BH4) content may further be measured as described further below.

Alternatively, the screening methods of the invention may be used to identify candidate compounds that decrease the biological activity of BH4 by decreasing its binding to BH4-dependent enzymes or BH4-binding receptors, or alternatively, that decrease the activity or levels of any of the BH4 synthetic enzymes. For example, a candidate compound may be tested for its ability to decrease GTPCH activity in cells that naturally express the enzyme, after transfection with cDNA for the enzyme, or in cell-free solutions containing the enzyme, as described further below. The effect of a candidate compound on the binding or activation of a BH4-dependent enzyme (such as NOS) or a BH4-binding receptor (or analogs) can be tested by radioactive and non-radioactive binding assays, competition assays, enzyme activity assays, receptor signaling assays.

As a specific example, mammalian cells (e.g., rodent cells) that express a nucleic acid encoding a BH4 synthetic enzyme are cultured in the presence of a candidate compound (e.g., a peptide, polypeptide, synthetic organic molecule, naturally occurring organic molecule, nucleic acid molecule, or component thereof). Cells may either endogenously express the BH4 synthetic enzyme or may alternatively be genetically engineered by any standard technique known in the art (e.g., transfection and viral infection) to overexpress the BH4 synthetic enzyme. The expression level of the BH4 synthetic enzyme is measured in these cells by means of e.g., Western blot analysis and subsequently compared to the level of expression of the same protein in control cells that have not been contacted by the candidate compound. A compound which promotes a decrease in the level of BH4 or intermediary as a result of reducing its synthesis by reducing the level or activity of one of its synthetic enzymes is considered useful in the invention. Given its ability to decrease the level or activity of BH4, such a molecule may be used, for example, as an analgesic therapeutic agent to treat, reduce, or prevent pain.

The activity of any of the BH4 synthetic enzymes may be measured by the rate at which they consume substrate, e.g., GTP or produce product, e.g., BH4 (see Werner et al. (1996) *J Chromatogr B Appl* 684:51-58). Radiometric assays are based on the consumption of labeled substrate. For example, GTPCH activity may be assessed by measuring the release of labeled formic acid originating from a labeled hydrogen atom of GTP and separation of formic acid from GTP by charcoal (Viveros et al. (1981) *Science* 213: 349). HPLC-based methods however, are superior to the radioactive method in that HPLC allows determination of the product. For measuring GTPCH activity, the tissue or cell homogenate containing GTPCH is incubated with excess GTP (substrate) in the presence of EDTA to ensure that the product 7,8 dihydropterin triphosphate is not further metabolized by the downstream PTPS which requires $Mg^{2+}$ to operate. The reaction is stopped by the addition of HCl and iodine. This also results in oxidation of the labile 7,8-dihydroneopterin triphosphate to the more stable neopterin triphosphate. Neopterin triphosphate may be analyzed directly by ion-pair HPLC and fluorescence detection. Alternatively, the mixture is treated with NaOH and alkaline phosphatase to yield neopterin which can be analyzed using reversed-phase HPLC with fluorescence detection, immunoassay or direct fluorescence in case of "pure" samples (such as in vitro kinase assay or CSF).

Sepiapterin reductase activity is commonly assayed using sepiapterin as artificial substrate and measuring levels of total biopterin after oxidation of BH4 and BH2 to biopterin.

For determination of PTPS activity, the substrate 7,8 dihydroneopterin triphosphate is typically freshly prepared with purified GTPCH. The incubation mixture also typically contains purified sepiapterin reductase, so that PTPS activity may be evaluated by measuring biopterin levels after oxidation of BH4 and BH2.

Given its ability to decrease the levels of BH4 or the levels or activity of a BH4 synthetic enzyme, such a molecule may be used, for example, as an analgesic therapeutic agent to treat, reduce, or prevent pain.

Alternatively, or in addition, candidate compounds may be screened for those which specifically bind to or inhibit a BH4 synthetic enzyme, BH4-dependent enzyme, or BH4-binding receptor. The efficacy of such a candidate compound is dependent upon its ability to interact with BH4, a BH4 synthetic enzyme or a BH4-binding enzyme or receptor. Such an interaction can be readily assayed using any number of standard binding techniques and functional assays (e.g., those described in Ausubel et al., supra). For example, a candidate compound may be tested in vitro for interaction and binding with BH4 and its ability to modulate pain may be assayed by any standard assays (e.g., those described herein).

In one particular example, a candidate compound that binds to any of the BH4 synthetic enzymes may be identified using a chromatography-based technique. For example, a recombinant BH4 synthetic enzyme protein may be purified by standard techniques from cells engineered to express the BH4 synthetic enzymes (e.g., those described above) and may be immobilized on a column. Alternatively, BH4 may be immobilized on a column. A solution of candidate compounds is then passed through the column, and a compound specific for either BH4 or one of the BH4 synthetic enzymes is identified on the basis of its ability to bind to BH4 or a BH4 synthetic enzyme and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography).

Screening for new inhibitors and optimization of lead compounds may be assessed, for example, by assessing GTPCH activity as described above. For screening of multiple substances, a 96 well-based enzyme assay may be used where purified recombinant GTPCH is incubated together with substrate and the potential inhibitor followed by oxidation and measurement of neopterin with a fluorescence ELISA reader. Neopterin shows intense fluorescence and can be directly measured.

Assays may also be based on BH4 measurement. BH4 shows no intense fluorescence, because the rings of the molecule are not in the fully oxidized, aromatic state. To circumvent this, a differential oxidization method in which dihydrobiopterin and BH4 are measured following their oxidation to biopterin may be used, with a limit of detection of 0.3 pmol for biopterin with fluorescence (Fukushima and Nixon, *Anal. Biochem.* (1980) 102: 176-188). Assays for measuring the activity of GTPCH or levels of biopterin are described, for example, by Kaneko et al., *Brain Res. Brain Res. Protoc.* (2001) 8:25-31; Ota et al., *J. Neurochem.* (1996) 67: 2540-2548; Bräutigam et al., *Physiol Chem*. (1982) 363: 341-343; Curtius et al., *Eur. J. Biochem.* (1985) 148: 413-419; Stea et al., *J. Chromatogr.* (1979) 168: 385-393; Werner et al., *J. Chromatogr.* (1996) 684: 51-58; Werner et al., *Methods Enzymol.* (1997) 281: 53-61; Nagatsu et al., *Anal. Biochem.* (1981) 110: 182-189; and Geller et al., *Biochem Biophys Res Commun* (2000) 276: 633-41.

In addition, these candidate compounds may be tested for their ability to function as analgesic agents (e.g., as described herein). Compounds isolated by this approach may also be used, for example, as therapeutics to treat, reduce, or prevent pain. Compounds which are identified as binding to BH4, any of the BH4 synthetic enzymes, BH4 dependent enzymes, or BH4-binding receptors with an affinity constant less than or equal to 10 mM are considered particularly useful in the invention.

Ultimately, the analgesic efficacy of any of the candidate compounds identified by the present screening methods may be tested using any of the pain models described above.

Potential analgesics include organic molecules, peptides, peptide mimetics, polypeptides, and antibodies that bind to a nucleic acid sequence or polypeptide that encodes any of the BH4 synthetic enzymes or BH4 dependent enzymes or BH4 binding receptors and thereby inhibit or extinguish their activity. Potential analgesics also include small molecules that bind to and occupy the binding site of such polypeptides thereby preventing binding to cellular binding molecules, such that normal biological activity is prevented. Other potential analgesics include antisense molecules.

In addition to BH4, any of the BH4 synthetic enzymes may be used upon expression, as a target for the screening of candidate compounds. Furthermore, each of the compounds provided herein (e.g., DAHP, NAS, methotrexate, BH4, guanine, or any of the compounds found in FIG. 19) may also be used as lead compounds in the discovery and development of analgesic compounds.

Test Compounds and Extracts

In general, compounds capable of inducing analgesia are identified from large libraries of both natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their analgesic activity should be employed whenever possible.

When a crude extract is found to have an analgesic activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having analgesic activity. Methods of fractionation and purification of such heterogenous extracts are known in the art. If desired, compounds shown to be useful agents for the treatment of pain are chemically modified according to methods known in the art.

Pharmaceutical Therapeutics

The invention provides a simple means for identifying compounds (including peptides, small molecule inhibitors, and mimetics) capable of treating, reducing, or preventing pain. Accordingly, a chemical entity discovered to have medicinal value using the methods described herein are useful as either drugs or as information for structural modification of existing analgesic compounds, e.g., by rational drug design.

For therapeutic uses, the compositions or agents identified using the methods disclosed herein may be administered systemically, for example, formulated in a pharmaceutically-acceptable buffer such as physiological saline. Treatment may be accomplished directly, e.g., by treating the animal with compounds that treat, reduce, or prevent pain by interfering with the production of BH4 (by interfering with the biological activity of any of the BH4 synthetic enzymes) or by interfering directly with the biological activity of BH4 by blocking activation of enzymes that use it as a cofactor or receptors that bind to BH4. Preferable routes of administration include, for example, subcutaneous, intravenous, intraperitoneally, intramuscular, or intradermal injections, which provide continuous, sustained levels of the drug in the patient. Treatment of human patients or other animals will be carried out using a therapeutically effective amount of an analgesic in a physiologically-acceptable carrier. Suitable carriers and their formulation are described, for example, in Remington's *Pharmaceutical Sciences* by E. W. Martin. The amount of the analgesic to be administered varies depending upon the manner of administration, the age and body weight of the patient, and with the type of disease and extensiveness of the disease. Generally, amounts will be in the range of those used for other agents used in the treatment of pain, although in certain instances lower amounts will be needed because of the increased specificity of the compound. A compound is administered at a dosage that inhibits pain. For example, for systemic administration a compound is administered typically in the range of 0.1 ng-10 g/kg body weight.

The results of the invention are now described in more detail in the following examples. These examples are provided to illustrate the invention and should not be construed as limiting.

Example 1

Induction of Synthetic Enzymes of the BH4 Pathway by Peripheral Nerve Injury

Transection of the peripheral axons of primary sensory neurons results in profound alterations in their metabolism, regenerative capacity, survival, excitability, transmitter function, and sensitivity to diverse extrinsic and intrinsic signals. These changes are mediated by transcriptional alterations triggered both by the loss of trophic support from peripheral target organs and by novel signals generated at the injury site. These transcriptional changes lead to adaptive responses, such as the capacity to survive the injury and re-grow the injured axon, as well as maladaptive responses that can result in a change in sensation, including the generation of neuropathic pain.

High-density rat oligonucleotide microarrays have been used to detect changes in gene expression in the dorsal root ganglion (DRG) following sciatic nerve transection (axotomy). The DRG represents a dense collection of cell bodies of one general class of neurons, the primary sensory neuron. The lesion has a uniform impact on the cells, and the existence of a large pool of genes with known regulation allows for quality controls for changes identified by the microarrays.

Affymetrix rat U34A oligonucleotide arrays were used to screen for changes in gene expression in DRG neurons during maturation of the DRG in the embryo and after a sciatic nerve lesion. In the first study we found that the expression profile of several genes, including dihydropteridine reductase (DHPR), was characterized by high levels of expression early during development, a down-regulation during adulthood, and re-expression following peripheral nerve injury (FIG. 1A and 1B). A more detailed study was then performed looking at alterations in gene expression three days following a peripheral nerve (sciatic) transection (axotomy, Ax) by comparing expression levels with non-injured DRGs (naïve, N) as described previously by Costigan et al., (*BMC Neuroscience* (2002) 3:16), hereby incorporated by reference. Nine biologically independent array hybridizations were performed (six naïve and three after axotomy). DRG tissue (L4 and L5 from the left or ipsilateral side to the injury) from five male Sprague-Dawley rats was pooled for each RNA population. Each RNA sample was labeled separately and hybridized to a separate array. Two comparisons were made using two sets of triplicate microarrays: naïve versus naïve and naïve versus axotomy. Genes were defined as detected if they received a present or marginal call in at least one of the arrays within each comparison. Since each individual sample was pooled from five male Sprague-Dawley animals of a similar age and from a single supplier (Charles River), biological variation is likely to be minimal.

In addition to DHPR, this analysis further revealed that two other members of the tetrahydrobiopeterin synthesis pathway (see FIG. 2A) were also significantly upregulated by peripheral nerve injury: GTP cyclohydrolase (GTPCH) and sepiapterin reductase (SPR) (See FIG. 3).

Example 2

Validation of Microarray Analysis

Figure 4:
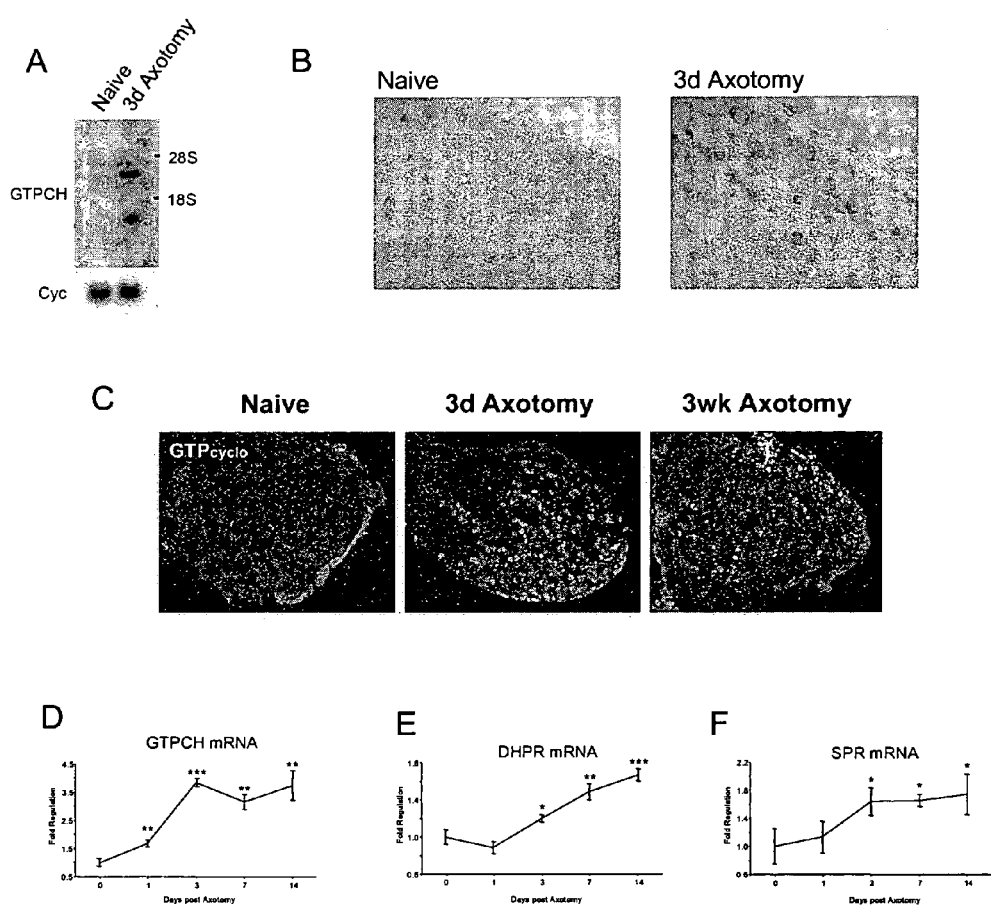
FIG. 4A is a picture of a Northern blot analysis showing mRNA expression of GTP cyclohydrolase (GTPCH) in the dorsal root ganglia (DRG) before (naïve) and following peripheral nerve injury.
FIG. 4B is a series of photomicrographs showing non-isotopic in situ localization of GTPCH mRNA in the DRG before (naïve) and following peripheral nerve injury.
FIG. 4C is a series of photomicrograph of DRGs showing increased GTPCH mRNA in neurons 3 days and 3 weeks after a peripheral nerve injury as detected by isotopic in situ hybridization.
FIGS. 4D-4F are a series of graphs representing GTPCH, DHPR, and sepiapterin reductase (SPR) mRNA levels as measured by Northern Blot analysis in the DRG over a period of 14 days following peripheral nerve injury (*$p<0.05$; $p<0.01$; *$p<0001$).
Figure 5:
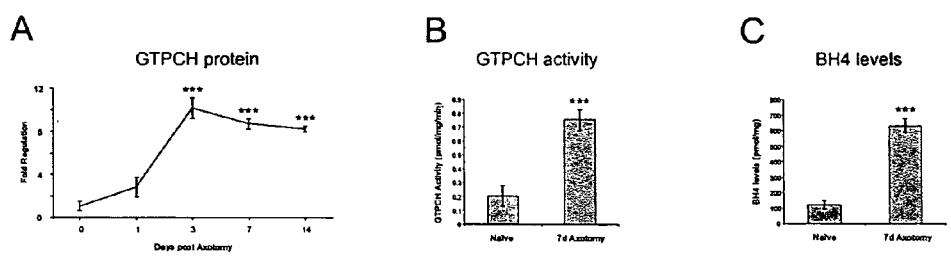
FIGS. 5A and 5B represent a series of graphs showing protein levels and enzyme activity of GTPCH before and following peripheral nerve injury (*$p<0.05$; $p<0.01$; *$p<0001$).
FIG. 5C is a bar graph showing BH4 levels in the DRG before and following peripheral nerve injury.
Figure 6A:
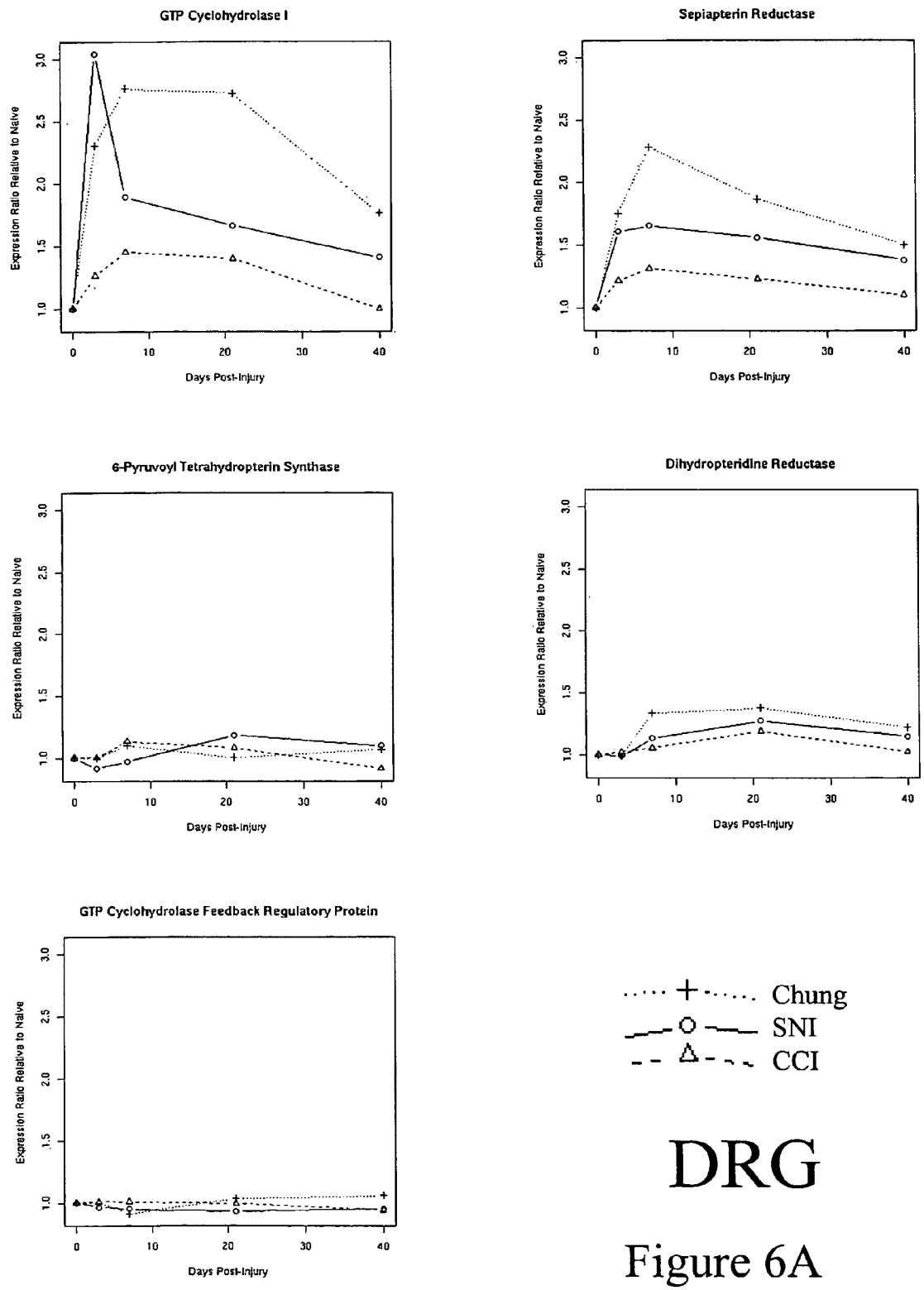
FIG. 6A are a series of graphs showing the ratio of experimental to naïve intensity readings from triplicate Affymetrix microarrays over time, of the various members of the BH4 synthetic pathway in three different neuropathic pain models (spared nerve injury (SNI), chronic constriction injury (CCI) and the spinal nerve ligation (SNL) models.
Figure 6B:
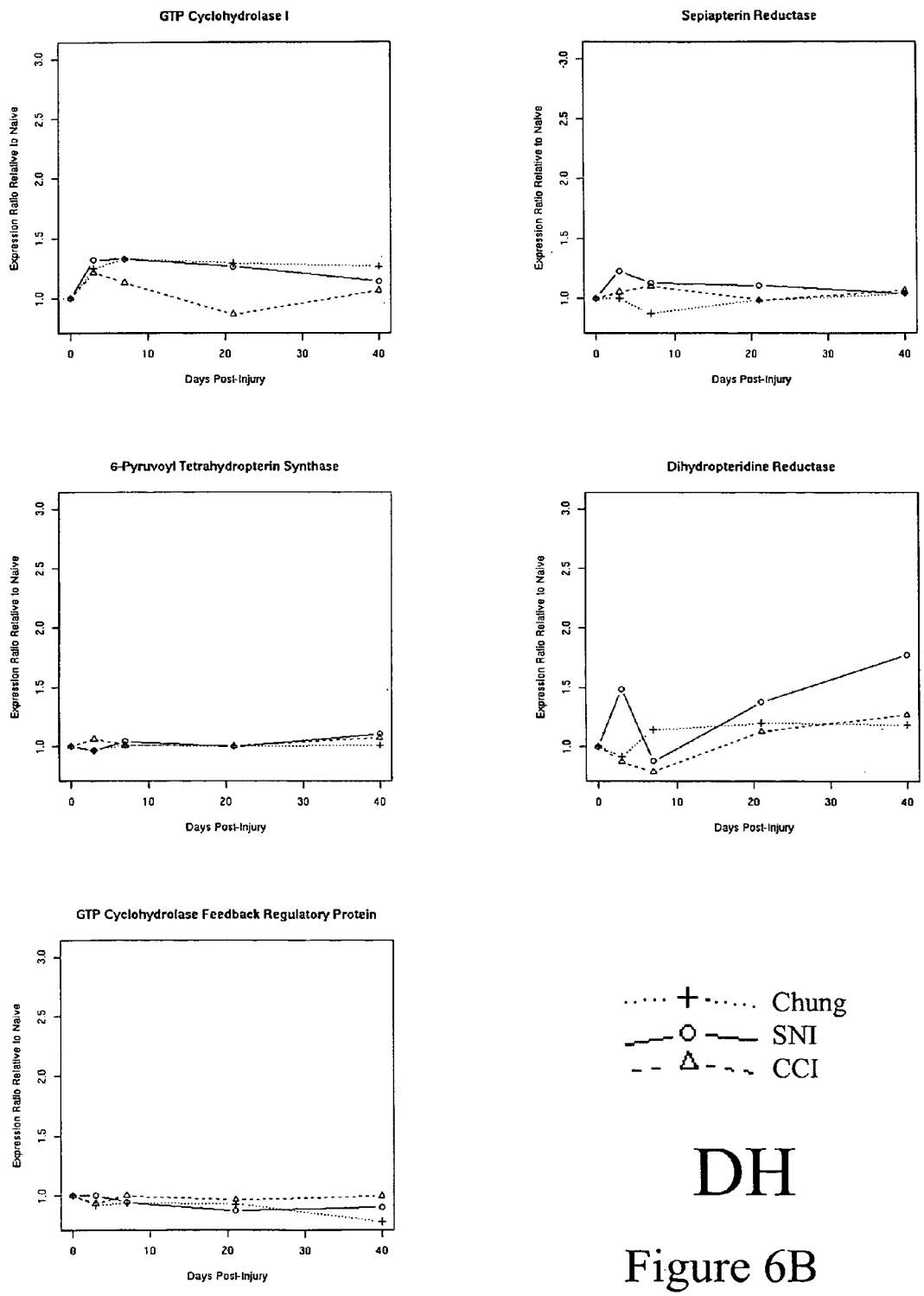
Figure 7A:
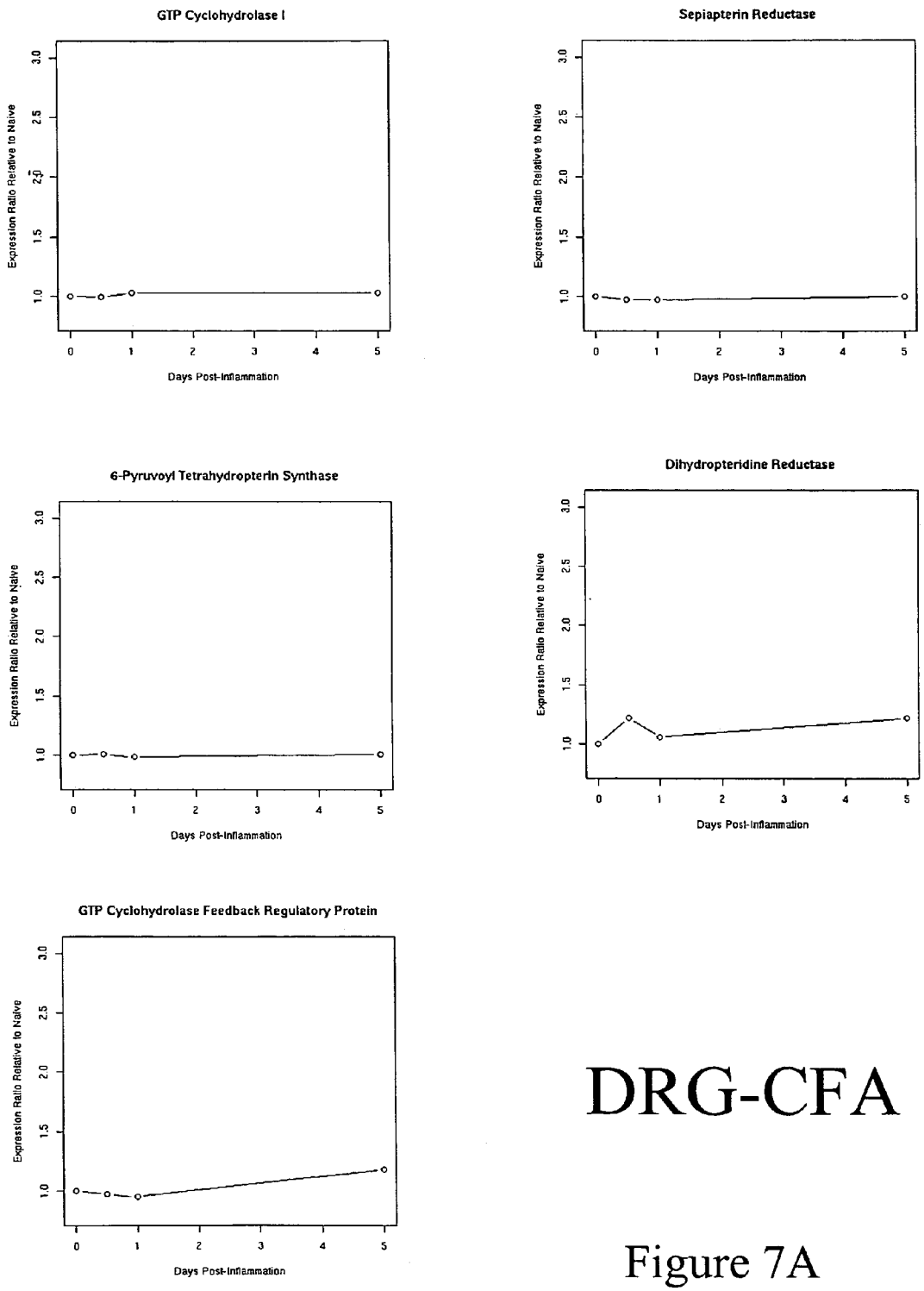
FIGS. 7A and 7B are a series of graphs showing the ratio of experimental to naïve intensity readings from triplicate Affymetrix microarrays over time of the various members of the BH4 synthetic pathway in the DRG (7A) and dorsal horn (7B) after peripheral inflammation produced by intraplantar complete Freund's adjuvant.
Figure 7B:
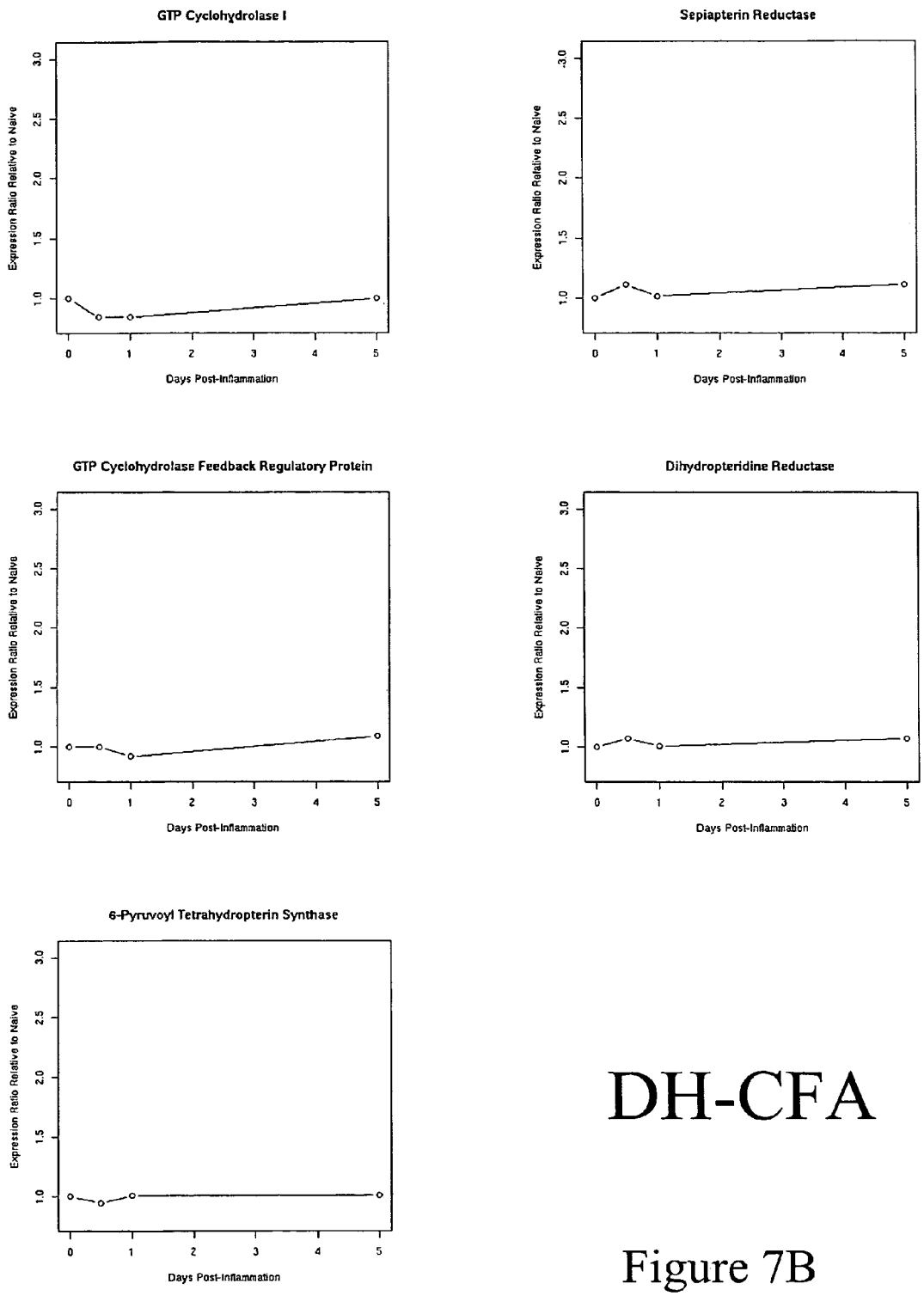

The induction of BH4 synthetic enzymes by axotomy was next confirmed by various methods, such as Northern blot analysis, Northern slot blot analysis, in situ hybridization, and Western blot analysis. A sample from each group was prepared from independent L4 and L5 DRG RNA samples extracted from different groups of animals than those used for the arrays. FIG. 1B represents a Northern slot blot analysis showing the expression profile of DHPR during embryonic development and in the adult, before and after axotomy and thereby confirming our microarray data. Northern Blot analysis to detect GTPCH mRNA levels in naïve DRG and 3 days following injury clearly show the marked induction of two transcripts of 3 kb and 1.2 kb (see FIG. 4A). FIG. 3 summarizes the degree of the induction of BH4 synthetic enzymes in DRG following axotomy. In situ analysis further confirmed the induction of GTPCH mRNA in neurons of the DRG three days post peripheral nerve injury (FIG. 4B). FIGS. 4D-4F represent triplicate Northern blot analysis demonstrating that the induction of GTPCH, DHPR, and SPR mRNA transcript levels in the DRG following axotomy is sustained for at least 2 weeks. We further show that the increase in GTPCH mRNA levels following nerve injury is associated with an increase in protein levels (FIG. 5A) and enzyme activity (FIG. 5B). FIG. 5A represents a Western Blot analysis of GTPCH protein levels in naïve DRG and 1, 3, 7, and 14 days post-axotomy showing a marked and sustained increase in GTPCH levels following axotomy. GTPCH activity levels in the DRG are markedly higher at seven days post axotomy relative to control (FIG. 5B). The amount of BH4 in the DRG is also increased (FIG. 5C) seven days post axotomy relative to control.

Example 3

Changes in BH4 Synthetic Enzymes in Neuropathic and Inflammatory Pain Models

Triplicate Affymetrix microarrays were used to establish the time course of changes of expression of the BH4 synthetic pathway members (GTPCH, SPR and DHPR as well as 6-pyruvoyl tetrahydropterin synthase and the feedback regulatory protein, GTPCH feed-back regulatory protein) in the DRG and in the dorsal horn of the spinal cord in three independent peripheral neuropathic pain models and after peripheral inflammation. GTPCH I, SPR, PTPS and DHPR were all upregulated by a substantial degree and for prolonged periods in the DRG in all three peripheral neuropathic pain models (FIGS. 6A-6J). The mRNA for all these enzymes was detectable in the dorsal horn (i.e. are constitutively expressed) but showed minimal alterations in expression in the pain models. In both the DRG and dorsal horn, peripheral inflammation also did not produce marked changes in the constitutive basal level of expression of the BH4 synthetic enzymes (FIG. 7A-I).

Example 4

Effects of an Inhibitor of GTPCH on Neuropathic Pain

Based on these findings, we hypothesized that the BH4 pathway may have a role in the biological response to peripheral nerve injury including activation of cell survival responses, changes in excitability, alterations in transmitter function, and change in growth status. In particular, we hypothesized that the pathway may have a role in the generation of pain after peripheral nerve injury (peripheral neuropathic pain) for example by increasing NOS activity as a result of the increase in BH4 levels.

To assess whether the BH4 synthetic pathway is involved in neuropathic pain, we examined if DAHP could elicit analgesia in various pain models, such as the spared nerve injury (SNI) model (FIGS. 8A-8H), the chronic constriction injury (CCI) model (FIGS. 9A and 9B), the formalin assay (FIG. 10), and the CFA model (FIGS. 11A-E).

Figure 10:
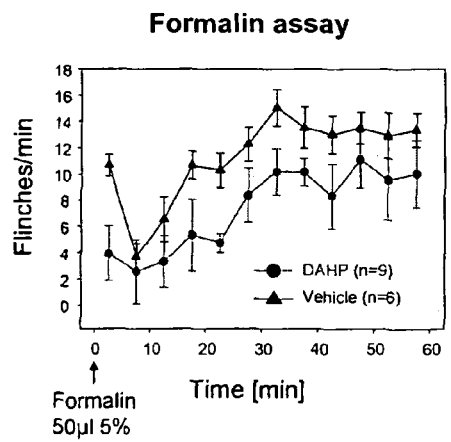
FIG. 10 shows the effect of DAHP on the flinching behavior in the Formalin test. DAHP (180 mg/kg) was injected i.p. one hour before injection of formalin into the hindpaw. Flinches were counted for one hour starting right after formalin injection.
Figure 11:
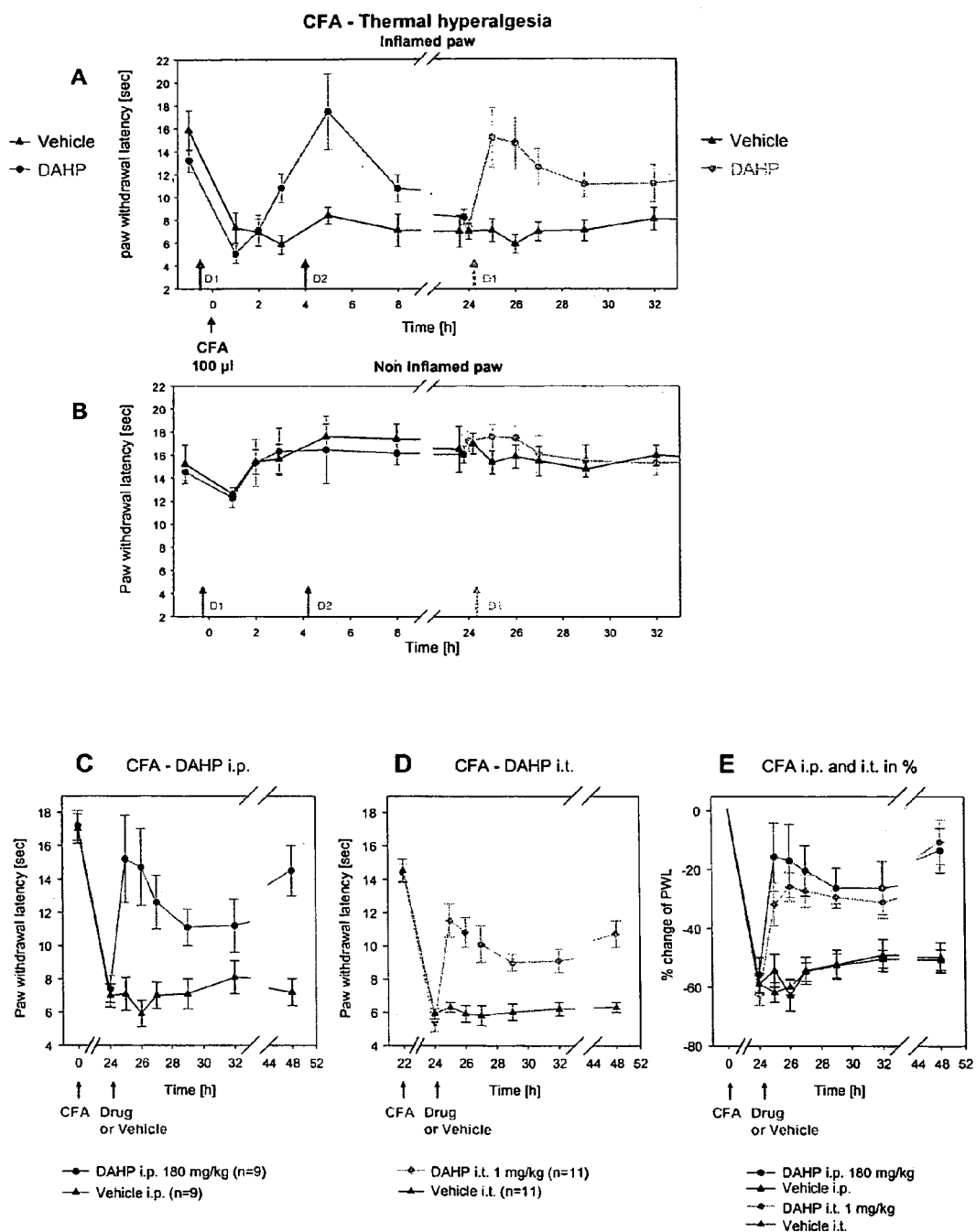
FIGS. 11A-11E are a series of graphs showing the effect of DHAP on thermal hyperalgesia in the CFA model which is a model for inflammatory pain.

Using the SNI model, we show that treatment with DAHP (180 mg/kg/day injected intraperitoneally) following surgery produced a reduction in mechanical sensitivity (von Frey threshold) and cold pain (cold allodynia by the application of acetone to the paw) relative to rats injected with vehicle, whether treatment was initiated at an early time point (e.g., three days post-surgery, see FIGS. 8A-8D) or at a later time point (e.g., seventeen days post-surgery, see FIGS. 8E-8F). Thus, treatment with DAHP could produce analgesia even once neuropathic pain was established. DAHP (6 mg/kg/day i.t.) also reduced mechanical and cold allodynia when administered as a continuous intrathecal infusion through a lumbar spinal catheter. The efficacy was comparable with intraperitoneal treatment. The analgesic effects of DAHP were further confirmed in the CCI model (180 mg/kg/d i.p.; FIGS. 9A and 9B). DAHP (single i.p. dose of 180 mg/kg) also reduced the flinching behavior in the formalin assay (FIG. 10).

Figure 8:
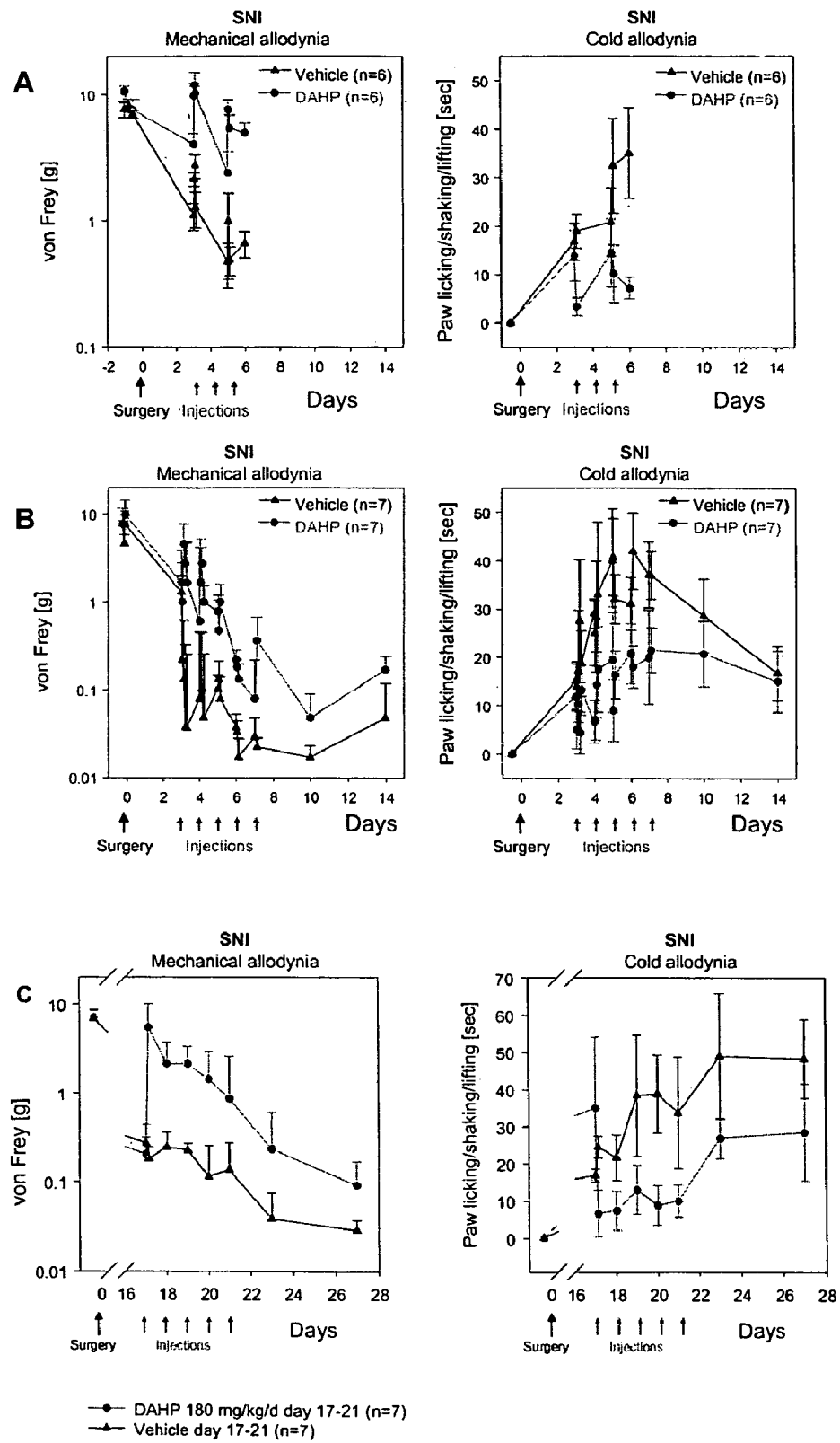
FIGS. 8A-8D represent a series of graphs showing the effect of DAHP on nociceptive behavior in the SNI model of neuropathic pain. Figures on the left show the threshold to mechanical stimuli applied with von Frey hairs (von Frey threshold). Figures on the right show the duration of paw licking, shaking and lifting following acetone application to the paw as a measure for cold allodynia.
Figure 9:
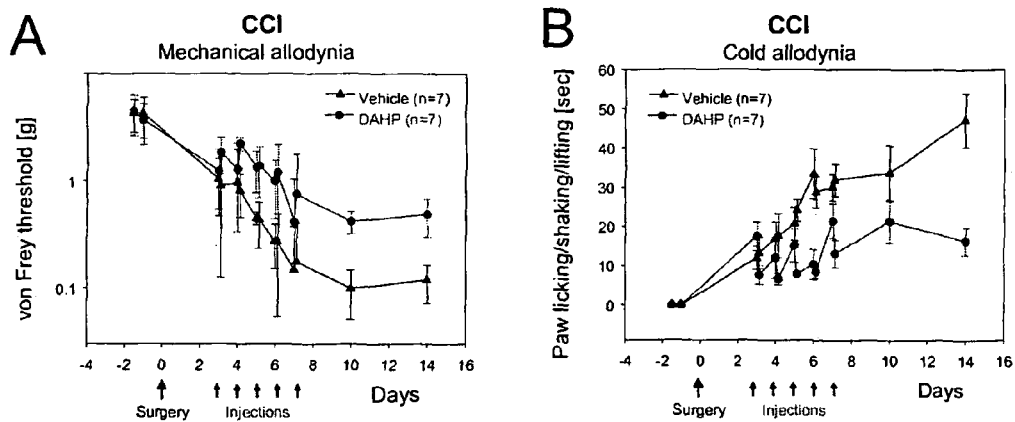
FIGS. 9A and 9B are two graphs showing the effect of DAHP on nociceptive behavior in the CCI model of neuropathic pain.
Figure 22:
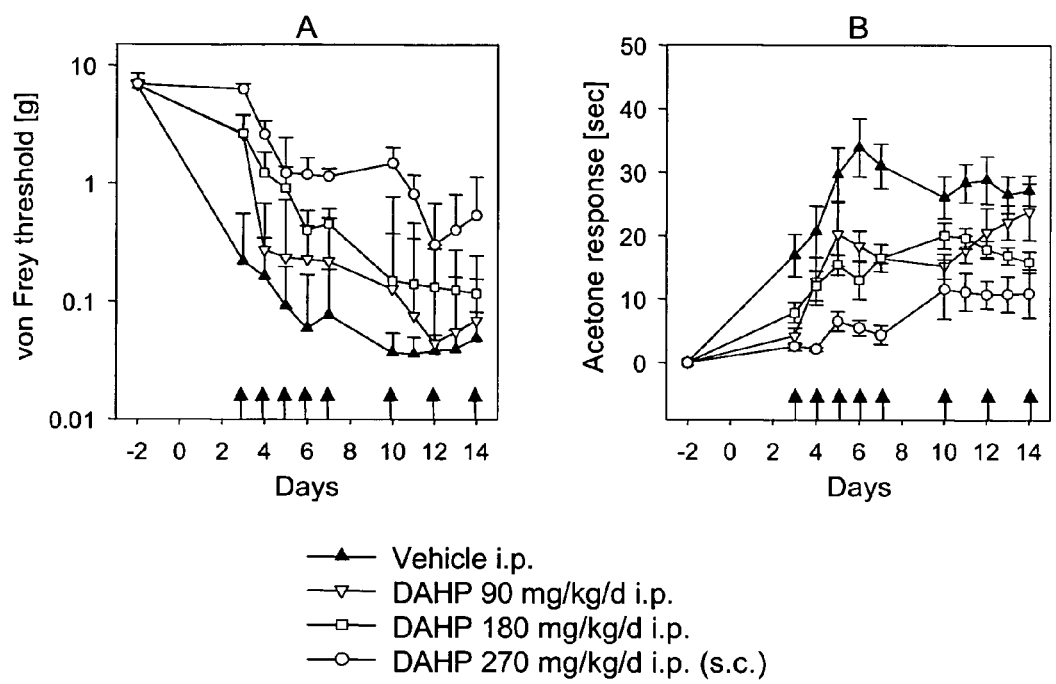
FIGS. 22A and 22B are a series of graphs demonstrating that the anti-nociceptive effect of DAHP follows a dose-response relationship for mechanical stimuli (FIG. 22A) and thermal stimuli (FIG. 22B) in the SNI model of nerve injury. In this graph, closed triangles represent vehicle, i.p.; open triangles represent DAHP at 90 mg/kg/day, i.p.; open squares represent DAHP at 180 mg/kg/day, i.p.; and open circles represent DAHP at 270 mg/kg/day, i.p.

The results of FIG. 8 demonstrating the analgesic effects of DAHP in an SNI model were extended through the use of increasing doses of DAHP. FIGS. 22A and 22B demonstrate that a dose-dependent relationship exists between the amount of DAHP administered and the nociceptive response to mechanical (von Frey test) or thermal (cold allodynia) stimuli. This dose-effect relationship was linear in the dose range tested. Up to the highest dose of 270 mg/kg/d, no obvious neurological adverse effects were observed over 14 days of treatment. These results further support the pharmacological effect of BH4 pathway inhibitors.

Moreover, as expected, intrathecal administration of BH4 was pro-nociceptive. FIG. 23A demonstrates that intrathecal administration of BH4 onto the lumbar spinal cord through a chronically implanted catheter reduces the paw withdrawal latency to a thermal stimulus (Hargreaves model) in naïve rats, indicating an increased hypersensitivity to heat. Likewise, in rats with pre-existing heat hypersensitivity, intrathecal BH4 administration induced heat hypersensitivity in the ipsilateral, but not contralateral, paw in a CFA-induced model of paw inflammation.

We next injected complete Freund's adjuvant (CFA) into the right paw of rats to elicit paw inflammation. We show using the CFA pain model that DAHP (180 mg/kg i.p.) reduced thermal hyperalgesia, whether treatment was initiated 30 min before (FIG. 11A, left side) or 24 h (FIGS. 11A, right side and 11C) after the CFA injection. DAHP had no effect on the paw withdrawal latency of the non-inflamed contralateral paw (FIG. 11B), indicating that DAHP had no general obvious inhibitory effect on sensory and motor functions. DAHP (1 mg/kg i.t.) also reduced thermal hyperalgesia when it was delivered to the lumbar spinal cord by intrathecal injection through a lumbar spinal catheter (FIG. 11D). Direct comparison of intraperitoneal and intrathecal DAHP treatment revealed that effects are similar with both routes of drug administration (FIG. 11E) The fact that there was no difference in the analgesic effect in rats treated with DAHP intrathecally and intraperitoneally infers that DAHP is effective at the level of the spinal cord and DRG.

Figure 12:
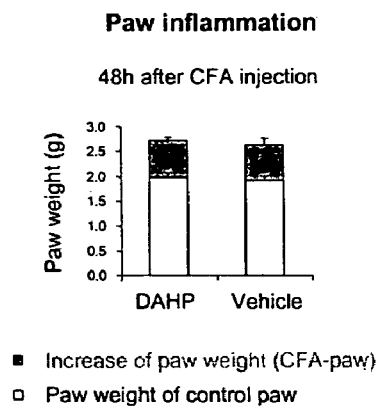
FIG. 12 is a bar graph showing the increase of the paw weight of the inflamed paw compared with the contralateral paw. Paw weight was determined 48 hours following CFA injection. The increase of the paw weight is a measure for the inflammatory paw edema and therefore allows assessment of paw inflammation.
Figure 13:
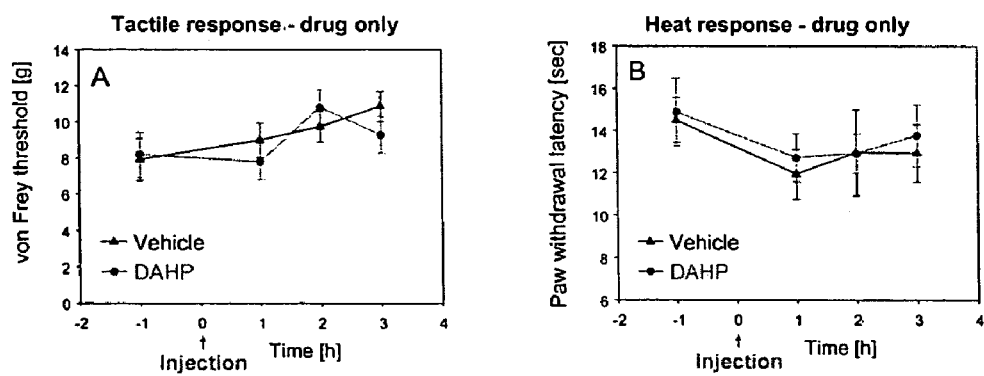
FIGS. 13A and 13B are a series of graphs showing the effects of DAHP on the response to tactile (13A) and heat stimuli (13B) in naïve rats. A single dose of DAHP (180 mg/kg i.p.) or vehicle was injected at time "zero".

We next measured the effect of DAHP on inflammatory paw edema. As shown in FIG. 12, measuring the paw weight in the CFA injected paw and the non-injected control paw showed no difference in the degree of paw inflammation between DAHP treated and control animals. Thus, because the administration of DAHP has no obvious effect on inflammation (no anti-inflammatory action), our results suggest that DAHP's analgesic effect is primarily a result of changes in sensory processing in the nervous system Using the von Frey and the Hargreaves thermal pain test, we further show that the injection of DAHP in non-injured animals did not result in a difference in motor activity. Based on these results, and the absence of any detectable changes in locomotion (FIGS. 13A-13B) the possibility that DAHP at the doses used has an effect on general sensory and motor activity seems unlikely. In addition there was not detectable change in the general level of activity with no obvious signs of sedation.

Figure 14:
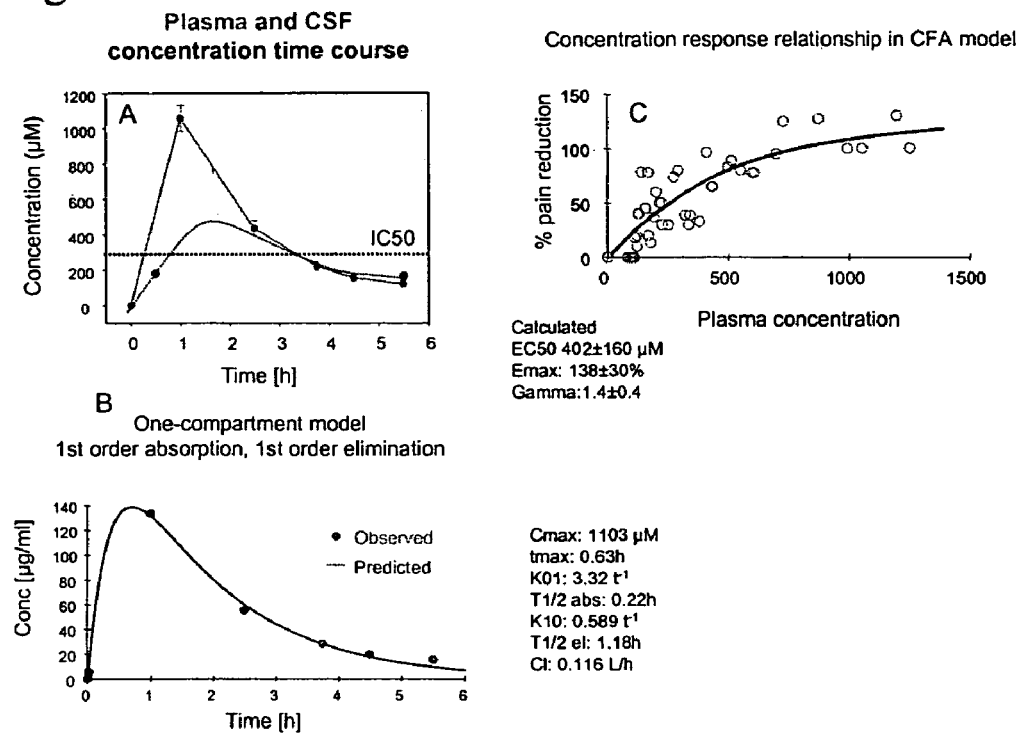
FIGS. 14A-14C represent a series of graphs showing pharmacokinetic features of DAHP and the pharmacokinetic-pharmacodynamic relationship.

We next performed pharmacokinetic studies to inspect the levels of DAHP in plasma and CSF (see FIGS. 14A and 14B) and show that the plasma concentration rapidly increased after i.p. injection followed by a rapid distribution in the cerebrospinal fluid. Furthermore, we confirmed that the increase in plasma DAHP concentration over time correlated with the behavioral effect in rats in response to DAHP treatment in the CFA model (FIG. 14C).

Example 5

Effects of Other BH4 Inhibitors on Inflammatory or Neuropathic Pain

We next evaluated the effect of inhibiting the BH4 synthetic enzyme Sepiapterin reductase by administering N-acetyl-serotonin (NAS). Similarly to DAHP, we show that NAS (50 mg/kg i.p.) resulted in a reduction of thermal hyperalgesia in the CFA model (see FIG. 15A). NAS treatment also had no effect on the CFA-induced inflammatory paw edema (FIG. 15B).

Similarly, we show that the administration of methotrexate, an inhibitor of DHPR, could result in a reduction in pain in the SNI model in response to mechanical and cold allodynia, in the absence of detectable acute toxicity. MTX was administered at low dose systemically (see FIG. 16A and 16B) or by continuous lumbar spinal delivery using an osmotic pump (0.1 mg/kg/day)(see FIGS. 16C and 16D). Toxicity was measured as body weight change over time (see FIGS. 16E and 16F).

Overall, our results demonstrate that the inhibition of BH4 synthesis by administering DAHP, NAS, or MTX for example, results in analgesia in response to thermal, mechanical, and chemical stimuli. Based on these results, inhibiting the synthesis of BH4, by reducing the biological activity of BH4 synthetic enzymes for example, induces analgesia, and therefore, may be used to treat, prevent, or reduce pain in a mammal in need thereof.

Example 6

Molecular and Cellular Effects of DAHP on Neuropathic Pain

Measurement of c-FOS expression in dorsal horn neurons was used as an objective indication of pain intensity. FIG. 24 demonstrates that c-FOS immunoreactivity is elevated in ipsilateral dorsal horn neurons of animals two hours after receiving formalin injection into the hindpaw. A significantly reduced elevation in c-FOS levels were observed in animals also administered intraperitoneal DAHP ($p<0.05$). This indicates that DAHP acts in the BH4 metabolic pathway upstream of immediate early gene c-Fos induction and reduces activation of neurons in the spinal cord.

Figure 25:
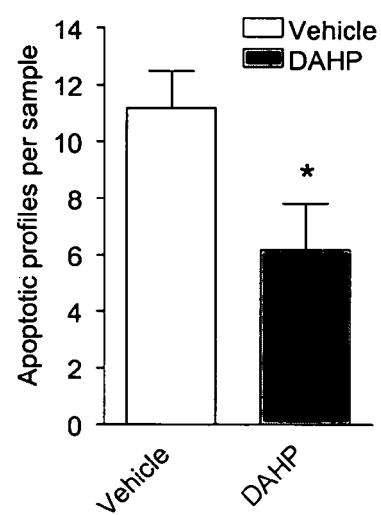
FIG. 25 is a bar graph showing the number of apoptotic cell profiles, using TUNEL staining, observed in the L4/L5 dorsal horn 7 days after SNI surgery of animals treated with either 180 mg/kg/day DAHP or vehicle control. Apoptotic neurons were detected by in situ TUNEL labeling and counted by a blinded observer.

Apoptosis of dorsal horn neurons contributes to the development of neuropathic pain following a nerve injury. To further investigate the cellular role of BH4 in neuropathic pain, apoptotic profiles of L4/L5 dorsal horn neurons were evaluated using TUNEL staining. FIG. 25 demonstrates that intraperitoneal DAHP administration protects dorsal horn neurons from apoptosis in the SNI model.

As discussed above, BH4 is an essential co-factor for nNOS and iNOS isozymes which have been shown to contribute to pain signaling in the nervous system. We have found that the anti-nociceptive effects of DAHP do not differ between nNOS knockout mice and wild-type mice (FIG. 26A), demonstrating the nNOS is not essential for the production of the analgesic effects of DAHP. We have also found that, DAHP induces a stronger antinociceptive effect than a high systemic dose of L-NAME, a non-specific NOS inhibitor, and that L-NAME does not further increase the efficacy of DAHP when injected together (FIG. 26B). Thus, the antinociceptive effects of DAHP cannot be attributed merely to an inhibition of NO production and the pro-nociceptive action of BH4 is not mediated solely through a NOS-dependent mechanism. Taken together, these data suggest that the pro-nociceptive effects of BH4 are likely mediated through a novel target molecule.

Example 7

Localization of GTPCH-I

Figure 29:
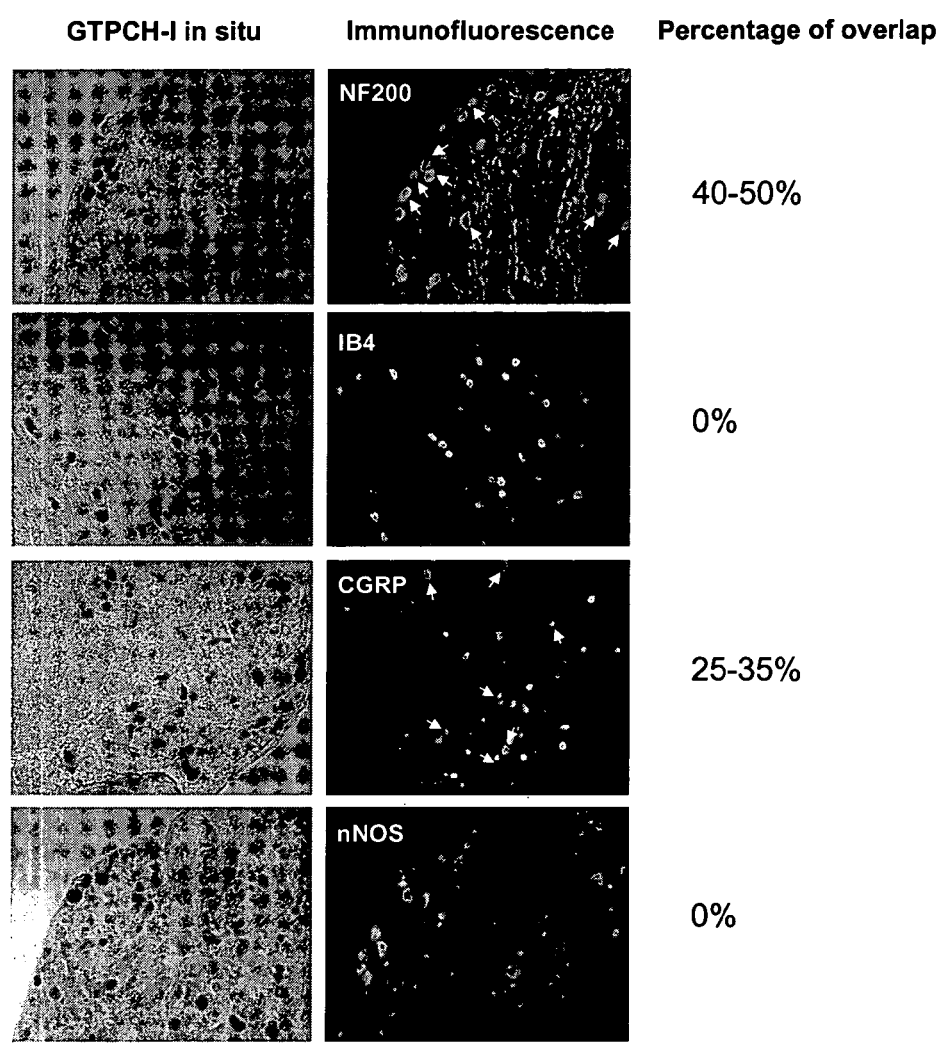
FIG. 29 is a series of photomicrographs showing, by in situ hybridization, the expression of GTPCH-I (left column) and, by immunofluorescence, the expression of NF200, *Griffonia simplicifolia* isolectin B4 (IB4), CGRP, and nNOS (center column). The number of cells co-expressing GTPCH-I and each of the identified proteins is expressed as a percentage of cells expressing GTPCH-I (right column).
Figure 31:
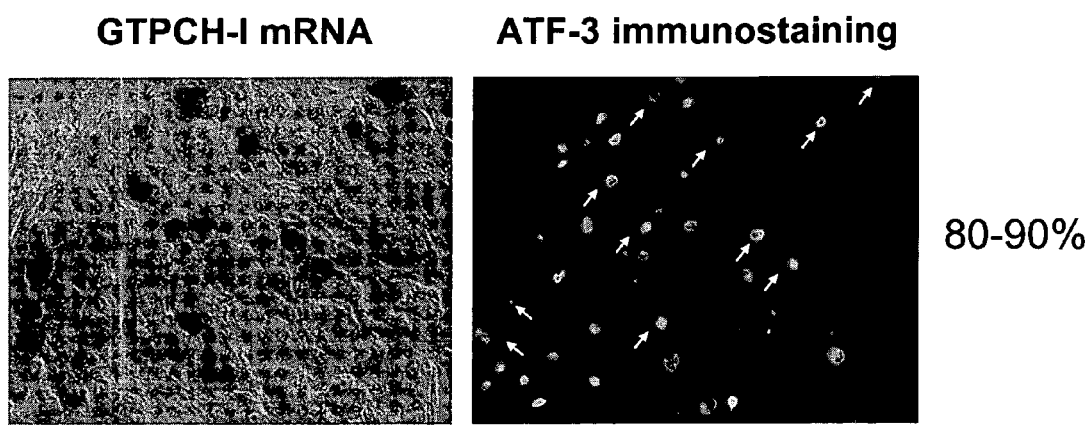
FIG. 31 are photomicrographs showing the co-localization of GTPCH-I mRNA, using in situ hybridization, and ATF-3 protein localization, using immunohistochemistry, following the SNI neuronal injury model. The arrows indicate cells that express GTPCH mRNA expression and also nuclear staining for ATF-3. Overall, 80-90% of GTPCH expressing neurons were ATF-3 positive demonstrating that GTPCH-1 upregulation occurs mostly in injured neurons.

We have characterized the localization of GTPCH-I. Upregulation of this enzyme occurs in large and small to medium sized DRG neurons after peripheral axonal injury (SNI model) compared to unlesioned animals (FIGS. 27A and 27B). Upregulation of GTPCH-I is not, however, observed in the CFA-induced paw inflammation model. Forty to fifty percent of neurons that upregulate GTPCH-I are also immunoreactive for neurofilament 200 (NF200) which is a marker for neurons having myelinated axons (FIG. 29). Thirty to forty percent of GTPCH-I mRNA positive neurons are also immunoreactive for calcitonin gene related peptide (CGRP; FIG. 29). CGRP labels small to medium sized neuropeptide positive sensory neurons, most of which are nociceptors. GTPCH-I expressing neurons do not express nNOS and are not labeled with *Griffonia simplicifolia* isolectin B4 (IB4; FIG. 29). IB4 labels small unmyelinated GDNF (glial cell derived neurotrophic factor) responsive neurons. GTPCH-I-expressing neurons show immunoreactivity for ATF-3 which indicates that the upregulation mainly occurs in injured neurons (FIG. 31).

The GTPCH-I transcript is not detectable in the dorsal horn of the spinal cord in either control or SNI-lesioned animals. Isolated injured motor neurons show GTPCH-I mRNA when their peripheral axons are transected by a peripheral nerve injury (FIG. 28A). GTPCH-I feedback regulatory protein (GFRP) mRNA can be detected in isolated DRG neurons and its expression does not change after nerve injury (FIG. 28B).

Example 8

Upregulation of BH4 Metabolites is Detected in Lesioned Dorsal Root Ganglia

Figure 30:
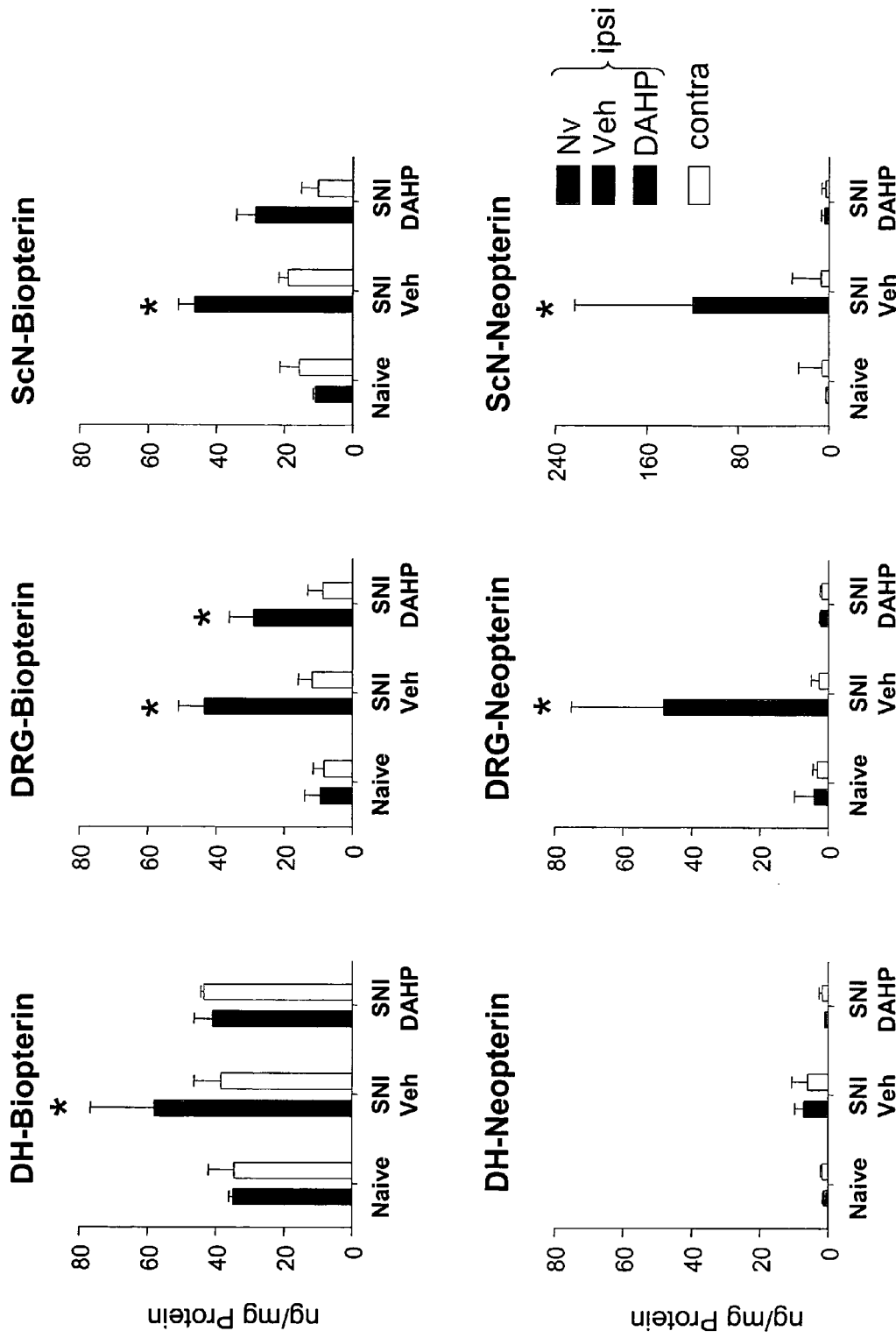
FIG. 30 is a series of bar graphs quantifying the levels of the BH4 metabolites biopterin and neopterin in the DH, DRG, and ScN following SNI surgery with and without DAHP treatment, compared to control.

We measured the levels of biopterin and neopterin, stable metabolites of BH4, in the DRG of animals following SNI lesion. Neopterin is a stable metabolite of BH4 found following BH4 recycling. The presence of neopterin may be an index of new BH4 synthesis, whereas biopterin is indicative of BH4 recycling and reuse, but not necessarily new synthesis. FIG. 30 demonstrates elevated biopterin levels in the ipsilateral doral horn (DH), the DRG, and the ScN compared to the contralateral side. Biopterin increases were reversed in the DH and the ScN, but not the DRG, with the administration of DAHP. Neopterin levels, by contrast, were elevated only in the DRG and ScN, but not the DH. These increases were reversed by DAHP administration. Together, these data demonstrate the usefulness of measuring stable BH4 metabolites as objective indicators of pain. Further, these data demonstrate that DAHP inhibits BH4 biosynthesis in vivo and inhibition of the BH4 biosynthetic pathway is a useful mechanism for inducing analgesia.

The above experiments were performed using the following materials and methods.

Materials and Methods

Surgical Procedures

All procedures were performed in accordance with Massachusetts General Hospital animal care regulations. Adult male Sprague Dawley rats (200-300 g) were anesthetized with halothane. For the sciatic nerve transection (axotomy), the left sciatic nerve was exposed at the mid thigh level, ligated with 3/0 silk, and sectioned distally. The wound was sutured in two layers, and the animals were allowed to recover. For SNI the tibial and peroneal branch of the sciatic nerve were ligated and transected whereas the sural nerve was spared. For CCI, the sciatic nerve was loosely ligated with dexon 4/0 (three ligatures) and for the spinal ligation model the L5 spinal segmental nerve was ligated.

Tissue and RNA Preparation

Animals were terminally anesthetized with $CO_2$, the L4 and L5 DRGs rapidly removed, and stored at −80° C. Total RNA was extracted from homogenized DRG samples using acid phenol extraction (TRIzol reagent, Gibco-BRL). RNA concentration was evaluated by $A_{260}$ measurement and quality assessed by electrophoresis on a 1.5% agarose gel. Each RNA sample used for hybridization of each array was extracted from rat L4 and L5 DRGs (10 ganglia pooled from 5 animals, per sample).

Microarray Analysis

Affymetrix rat genome U34A oligonucleotide microarrays, representing 8799 known transcripts and expressed sequence tags (ESTs), were used according to the manufacturers instructions (Santa Clara, Calif. http://www.affymetrix.com). Transcript abundance is estimated by analysis of signal intensity of the probe set for each transcript and comparison with mismatch controls. The arrays are hybridized with biotin-labeled cRNA, prepared as per standard Affymetrix protocol. Briefly, total RNA (8 µg) from DRGs was reverse transcribed using an oligo-dT primer coupled to a T7 RNA polymerase binding site. Double-stranded cDNA was made and biotinylated-cRNA synthesized using T7 polymerase. The cRNA was hybridized for 16 hours to an array, followed by binding with a streptavidin-conjugated fluorescent marker, and then incubated with a polyclonal anti-streptavidin antibody coupled to phycoerythrin as an amplification step. Following washing, the chips were scanned with a Hewlett-Packard GeneArray laser scanner and data analyzed using GeneChip software. External standards were included to control for hybridization efficiency and sensitivity.

Hybridization levels for each species of mRNA detected on the arrays are expressed by intensity (signal) and as present (P), marginal (M) or absent (A) calls, calculated by Affymetrix software (MAS 5.0, $\alpha1=0.04$ $\alpha2=0.06$). To normalize the array data standard Affymetrix protocols were employed, each array was scaled to a target signal of 2500 across all probe sets (MAS 5.0).

The arrays were grouped for comparison of a triplicate set of naïve data with a triplicate post-axotomy set. A probe set was determined undetected if it received an A call in all of the six arrays involved in the comparison. Detected were Present or Marginal by MAS5.0 in at least one array for each analysis. Mean signal and standard deviation were calculated for each detected probe set. The p-value for rejecting the null hypothesis that the mean signals were equal between the two triplicate sets was calculated using an unpaired, two-tailed t-test for independent samples with unequal variance (Satterthwaite's method). Fold-differences between the mean signals (A and B) in the two triplicate sets were calculated as max (A, B)/min(A, B) with down regulation relative to naïve expressed as negative.

cDNA Probe Production

To generate specific probes for Northern blot hybridization experiments, primers based on the rat accession number provided by Affymetrix were designed, primer pairs were chosen using the Primer3 software http://www-genome.wi.mit.edu/ from the 1000 most 3' nucleotides within each accession sequence. PCR was performed on cDNA reverse transcribed from total RNA, extracted from lumbar DRGs, using poly-dT as a primer to obtain cDNA fragments (141 to 596 bp). These fragments were subsequently cloned into the PCRII vector (TA cloning Kit, Invitrogen) and the identity of each was confirmed by sequencing in both directions. These cDNAs were gel-purified and used to produce $^{32}P$-labeled cDNA probes (Prime-It kit, Stratagene).

Northern Blot Analysis

Total RNA was size separated by electrophoresis on a 1.5% agarose/formaldehyde gel (10 µg of total RNA per lane) and transferred to a Hybond N+ nylon membrane. Membranes were hybridized with labeled-probes (see above) in ExpressHyb (Clontech) overnight at 65° C., washed, and exposed to X-ray film with an intensifying screen at −80° C.

Slot Blots

Total RNA (1.25 µg) was directly transferred to Hybond N+ nylon membrane under vacuum using a Hoefer PR648 slot blot apparatus (Amersham Pharmacia Biotech). Levels of hybridization were quantified using the 24450 phosphorimager system (Molecular Dynamics, Sunnyvale Calif.). The blots were probed for cyclophilin as a loading control. Loading levels between samples on each blot were normalized using the cyclophilin levels from the control blot.

Isotopic in situ Hybridization

DRGs were rapidly removed, embedded in OCT (Tissue Tek), and frozen. Sections were cut serially at 6 µm. Isotopic-in situ hybridization was carried out using forty-eight base pair oligonucleotide probes, designed to have 50% G-C content and be complementary to the mRNAs whose accession numbers were provided by Affymetrix. Probes were 3'-end labeled with $^{35}S$ or $^{33}P$-dATP using a terminal transferase reaction and hybridization carried out. Autoradiograms were generated by dipping slides in NTB2 nuclear track emulsion and storing in the dark at 4° C. Sections were exposed for 1-8 weeks (depending on the abundance of transcript), developed, fixed, and viewed under darkfield using a fiber-optic darkfield stage adapter (MVI). Controls to confirm specificity of oligonucleotide probes included hybridization of sections with labeled probe with a 1,000-fold excess of cold probe or labeled probe with a 1,000-fold excess of another, dissimilar cold probe of the same length and similar G-C content.

Assays for GTPCH Activity and Biopterin Concentration

Screening for new inhibitors and optimization of lead compounds may be assessed, for example, by assessing GTPCH activity. In this regard, its inhibition by various chemicals may be determined by incubating the enzyme with GTP and measuring the level of biopterin or neopterin production using fluorometric, radiolabel, immunoassay, spectrophotometry, and HPLC techniques.

Using the preferred method, tissue neopterin and biopterin levels were determined with a liquid chromatography tandem mass spectrometry method. After acidic pH oxidation with iodine according to Fukushima and Nixon (*Methods Enzymol.* 66: 429-436, 1980) tissues were extracted by solid phase extraction employing Oasis MCX extraction cartridges and concentrations of total biopterin, neopterin and the internal standard rhamnopterin were determined by liquid chromatography coupled to tandem mass spectrometry. HPLC analysis was done under gradient conditions using a Nucleosil C8 column. MS/MS analyses were performed on an API 4000 Q TRAP triple quadrupole mass spectrometer with a Turbo Ion Spray source. Precursor-to-product ion transitions of m/z 236 192 for biopterin, m/z 252 192 for neopterin, m/z 265 192 for rhamnopterin were used for the MRM. Concentrations of the calibration standards, quality controls and samples were evaluated by Analyst software 1.4 (Applied Biosystems). Linearity of the calibration curve was proven from 0.1-50 ng/ml. The coefficient of correlation for all measured sequences was at least 0.99. The intra-day and inter-day variability was <10%.

Alternative methods to determine BH4 employ radioenzymatic assays that require the production of separate and individual antibodies specific for each pterin species and/or oxidation state. Separation of pteridines is accomplished by chromatographic techniques and HPLC. HPLC with fluorescence detection enables rapid and sensitive determination of many biologically occurring pterins (including biopterin and pterin) in the picomole range in a single chromatographic run.

Tissue homogenates are centrifuged and the resulting supernatant is used for both enzyme and protein assays.

GTP cyclohydrolase I activity is assayed as described by Duch et al. (*Mol. Cell Endocrinol*. (1986) 47: 209-16) with the following modifications. The reaction mixture (500 ml) contained 0.1 M Tris-Cl (pH 7.8), 0.3 M KCl, 2.5 mM EDTA, 10% glycerol, 1 mM GTP, and the enzyme. The reaction was carried out at 37° C. for one hour in the dark and was terminated by the addition of 50 ml of iodine solution (1.0% $I_2$, 2.0% KI in 1.0 N HCl). After keeping the mixture at room temperature for one hour, excess iodine is reduced by addition of 50 ml of 2.0% ascorbate. The mixture was supplemented with 50 ml of 1.0 N NaOH and then incubated with 3.0 units (100 ml) of alkaline phosphatase at 37° C. for one hour. The reaction was stopped by the addition of 100 ml of 1.0 N acetic acid. After centrifugation, the supernatant was applied to a Whatman Partisil 10 ODS column (4.6×3×250 mm) connected to a Cosmosil 10 C18 column (4.6×3×50 mm). Neopterin was eluted isocratically with a solvent of 50 mM sodium acetate buffer (pH 5.0) containing 0.1 mM EDTA and 5% methanol at a flow rate of 0.8 ml/min. The column temperature was maintained at 25° C. The eluate was monitored with a fluoromonitor (excitation, 350 nm; emission 440 nm). Protein concentration was determined using a dye-binding assay kit (Bio-Rad) using immunoglobulin-G as a standard.

Cellular Biopterin Content

Total biopterin (BH1, BH2, and BH4) was measured in tissue lysates after acidic oxidation of reduced forms of biopterin with iodines. Following centrifugation at 12,000 rpm (three times for five minutes each), cell lysates are treated with 1% $I_2$ containing 2% KI in 1N HCl for one hour at 37° C. in the dark. Samples were then centrifuged at 12,000 rpm (three times for five minutes each) and the supernatants treated with ascorbate (0.1 M) to remove residual $I_2$. Extracts were then neutralized with 1 N NaOH followed by 200 mM Tris-Cl (pH 7.8). Biopterin was quantitated by C18 reverse HPLC using an online fluorescence detector.

The determination of cellular biopterin content is described in detail in the following references, Harada et al., *Science* (1993) 260: 1507-10, Kapatos et al., *J. Neurochem.* (1999) 72: 669-75, Maita et al., *Proc. Natl. Acad. Sci. USA* (2002) 99: 1212-7; Moali et al., *Chem Res Toxicol* (2001) 14: 202-10, Rebelo et al., *J. Mol. Biol*. (2003) 326: 503-16; Renodon-Corniere et al., *Biochemistry* (1999) 38: 4663-8; Xie et al., *J. Biol. Chem*. (1998) 273: 21091-8; Yoneyama et al., *J. Biol. Chem*. (1998) 273: 20102-8; Yoneyama et al., *Protein Sci*. (2001) 10: 871-8; Yoneyama et al. *Arch. Biochem. Biophys*. (2001) 388: 67-73, all of which are hereby incorporated by reference.

Dosages

The dosage of individual components or therapeutic combinations of the present invention can be readily determined by those skilled in the art of pain management. For example, the dose of an analgesic administered according to the present invention will be the same or less than that which is practiced in the art.

Formulation of Pharmaceutical Compositions

The administration of any compound of this invention may be by any suitable means that results in a concentration of the compound that is effective for the treatment of pain. The compound(s) may be contained in any appropriate amount in any suitable carrier substance, and is generally present in an amount of 1-95% by weight of the total weight of the composition. The composition may be provided in a dosage form that is suitable for the oral, parenteral (e.g., intravenous, intramuscular, or subcutaneous injection), rectal, or transdermal (topical) administration route. Thus, the composition(s) may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, or implants. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound (drug) substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance (sawtooth kinetic pattern); (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of compounds in the form of a controlled release formulation is especially preferred in cases in which the compound, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology, supra.

If more than one drug is administered simultaneously, the drugs may be mixed together in the tablet, or may be partitioned. In one example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions

The compound(s) may also be administered parenterally by injection, infusion, or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly (lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polvoxyethylene sorbitan fatty acid esters. Various additives, enhancers, or surfactants may be incorporated.

Percutaneous and Topical Compositions

The pharmaceutical compositions may also be administered topically on the skin for percutaneous (transdermal) absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE™. Examples of chelating agents are sodium EDTA, citric acid, and phosphoric acid. Examples of gel forming agents are CARBOPOL™, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN™)).

The pharmaceutical compositions described above may be applied by means of special drug delivery devices such as dressings or alternatively plasters, pads, sponges, strips, or other forms of suitable flexible material.

Controlled Release Percutaneous and Topical Compositions

There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a nonporous polymeric membrane (e.g., ethylene-vinyl acetate copolymer). The active compound is only released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer.

A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Other embodiments are within the claims.

What is claimed is:

1. A method of treating or reducing pain in a mammal in need thereof, said method comprising administering to said mammal a composition comprising a compound having the formula:

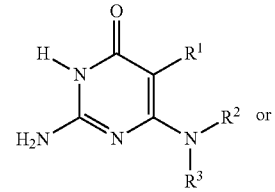
(I)

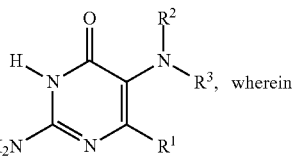
(II)

$R^1$ is H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$, wherein each of $R^4$ and $R^5$ is, independently, H, $C_{1-6}$ alkyl, $C_{6-12}$ aryl, heteroaryl, $C_{1-4}$ alkaryl, or $C_{1-4}$ alkheteroaryl, $R^2$ is H, $C_{1-6}$ alkyl, $C_{6-12}$ aryl, heteroaryl, $C_{1-4}$ alkaryl, or $C_{1-4}$ alkheteroaryl, and $R^3$ is H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl and each of $R^7$ and $R^8$ is, independently, H, $C_{1-6}$ alkyl, $C_{6-12}$ aryl, heteroaryl, $C_{1-4}$ alkaryl, or $C_{1-4}$ alkheteroaryl; or $R^3$ is as above and $R^1$ and $R^2$ together are represented by

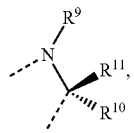 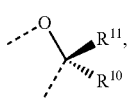

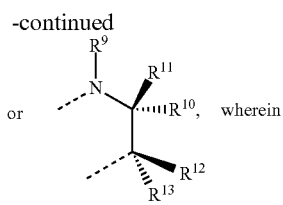

the N, O, or S of the $R^1/R^2$ linkage forms a bond to the pyrimidinone ring and each of $R^9$, $R^{10}$, $R^{11}$, $R^{12}$, and $R^{13}$ is, independently, H, $C_{1-6}$ alkyl, $C_{6-12}$ aryl, heteroaryl, $C_{1-4}$ alkaryl, or $C_{1-4}$ alkheteroaryl; or $R^3$ is as above and $R^1$ and $R^2$ together are represented by

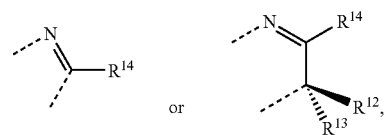

wherein the N of the $R^1/R^2$ linkage forms a bond to the pyrimidinone ring, each of $R^{12}$ and $R^{13}$ is as above, and $R^{14}$ is H, SH, $OR^4$, halo, $NO_2$, CN, $CO_2R^7$, $CONR^7R^8$, $SO_2R^7$, $SO_2NR^7R^8$,

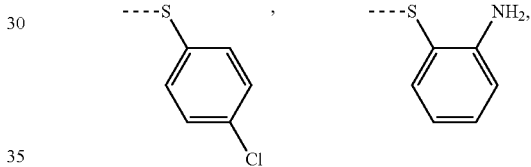

$C_{1-6}$ alkyl, $C_{6-12}$ aryl, heteroaryl, $C_{1-4}$ alkaryl, or $C_{1-4}$ alkheteroaryl, wherein each of $R^4$, $R^7$ and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl; or $R^1$ and $R^2$ together are represented by

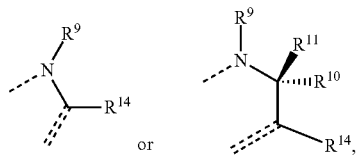

wherein the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$, in an amount sufficient to result in a reduction of BH4 biological activity and thereby treat or reduce pain.

2. The method of claim 1, wherein said mammal is a human.

3. The method of claim 1, wherein the pain is reduced by reducing the BH4 levels in primary sensory neurons or dorsal horn neurons.

4. The method of claim 3, wherein said primary sensory neurons are in a dorsal root ganglion or a trigeminal ganglion.

5. The method of claim 4, wherein said dorsal horn neurons are in the spinal cord or spinal nucleus of the trigeminal in the brainstem.

6. The method of claim 1, wherein the reduction in BH4 biological activity is the result of a reduction in BH4 synthesis or recycling.

7. The method of claim 1, wherein said BH4 biological activity is reduced by increasing the expression, GTPCH-binding, or activity of GTP cyclohydrolase feedback regulatory protein (GFRP).

8. The method of claim 6, wherein said reduction in BH4 synthesis is the result of a reduction in the level or biological activity of at least one enzyme selected from the group consisting of sepiapterin reductase (SPR), Pyruvoyltetrahydropterin Synthase (PTPS), GTP cyclohydrolase (GTPCH), Pterin-4α-carbinolamine dehydratase, and dihydropteridine reductase (DHPR).

9. The method of claim 8, wherein said reduction in BH4 synthesis is the result of a reduction in the biological activity of at least one enzyme selected from the group consisting of sepiapterin reductase (SPR), GTP cyclohydrolase (GTPCH), and dihydropteridine reductase (DHPR).

10. The method of claim 8, wherein the biological activity of at least two of said enzymes is reduced.

11. The method of claim 10, wherein the biological activity of at least three of said enzymes is reduced.

12. The method of claim 8, wherein said biological activity is reduced by at least 10%.

13. The method of claim 12, wherein said biological activity is reduced by at least 40%.

14. The method of claim 1, wherein said composition comprises a compound of formula (I), wherein
$R^1$ is H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$, wherein each of $R^4$ and $R^5$ is, independently, H, $C_{1-6}$ alkyl, $C_{6-12}$ aryl, heteroaryl, $C_{1-4}$ alkaryl, or $C_{1-4}$ alkheteroaryl,
$R^2$ is H, $C_{1-6}$ alkyl, $C_{6-12}$ aryl, heteroaryl, $C_{1-4}$ alkaryl, or $C_{1-4}$ alkheteroaryl, and
$R^3$ is H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl and each of $R^7$ and $R^8$ is, independently, H, $C_{1-6}$ alkyl, $C_{6-12}$ aryl, heteroaryl, $C_{1-4}$ alkaryl, or $C_{1-4}$ alkheteroaryl.

15. The method of claim 1, wherein said composition comprises a compound of formula:

(I)

$R^1$ and $R^2$ together are represented by or the N, O, or S of the $R^1/R^2$ linkage forms a bond to the pyrimidinone ring and each of $R^9$, $R^{10}$, $R^{11}$, $R^{12}$, and $R^{13}$ is, independently, H, $C_{1-6}$ alkyl, $C_{6-12}$ aryl, heteroaryl, $C_{1-4}$ alkaryl, or $C_{1-4}$ alkheteroaryl, and
$R^3$ is H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl and each of $R^7$ and $R^8$ is, independently, H, $C_{1-6}$ alkyl, $C_{6-12}$ aryl, heteroaryl, $C_{1-4}$ alkaryl, or $C_{1-4}$ alkheteroaryl.

16. The method of claim 1, wherein said composition comprises a compound of formula:

(I)

$R^1$ and $R^2$ together are represented by or wherein the N of the $R^1/R^2$ linkage forms a bond to the pyrimidinone ring,
$R^3$ is H, $C_{1-6}$ alkyl, $C_{6-12}$ aryl, heteroaryl, $C_{1-4}$ alkaryl, $C_{1-4}$ alkheteroaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl,
each of $R^{12}$ and $R^{13}$ is, independently, H, $C_{1-6}$ alkyl, $C_{6-12}$ aryl, heteroaryl, $C_{1-4}$ alkaryl, or $C_{1-4}$ alkheteroaryl,
$R^{14}$ is H, SH, $OR^4$, halo, $NO_2$, CN, $CO_2R^7$, $CONR^7R^8$, $SO_2R^7$, $SO_2NR^7R^8$,

, $C_{1-6}$ alkyl, $C_{6-12}$ aryl, heteroaryl, $C_{1-4}$ alkaryl, or $C_{1-4}$ alkheteroaryl,
wherein each of $R^4$, $R^7$, and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl.

17. The method of claim 1, wherein said composition comprises a compound of formula:

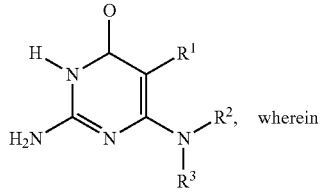

(I)

$R^1$ and $R^2$ together are represented by

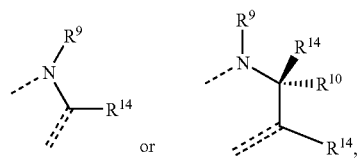

wherein the N of the $R^1/R^2$ linkage forms a bond to the pyrimidinone ring, each of $R^9$, $R^{10}$, and $R^{11}$ is, independently, H, $C_{1-6}$ alkyl, $C_{6-12}$ aryl, heteroaryl, $C_{1-4}$ alkaryl, or $C_{1-4}$ alkheteroaryl, $R^{14}$ is H, SH, $OR^4$, halo, $NO_2$, CN, $CO_2R^7$, $CONR^7R^8$, $SO_2R^7$, $SO_2NR^7R^8$,

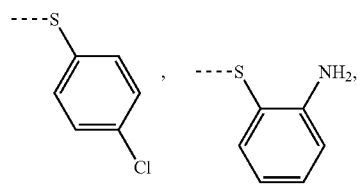

$C_{1-6}$ alkyl, $C_{6-12}$ aryl, heteroaryl, $C_{1-4}$ alkaryl, or $C_{1-4}$ alkheteroaryl, wherein each of $R^4$, $R^7$, and $R^8$ is, independently, H, $C_{1-6}$ alkyl, $C_{6-12}$ aryl, $C_{1-4}$ alkaryl, heteroaryl, or $C_{1-4}$ alkheteroaryl, $R^3$ does not exist, and a double bond is formed between the carbon bearing $R^{14}$ and the nitrogen bearing $R^2$.

18. The method of claim 14, wherein said composition comprises a compound selected from the group consisting of

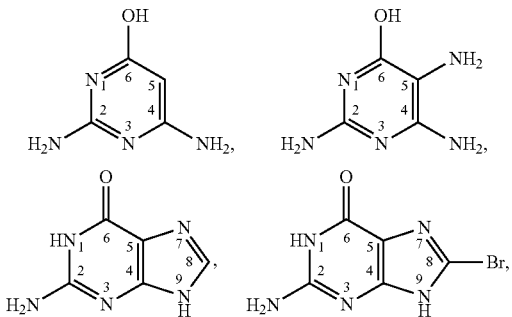

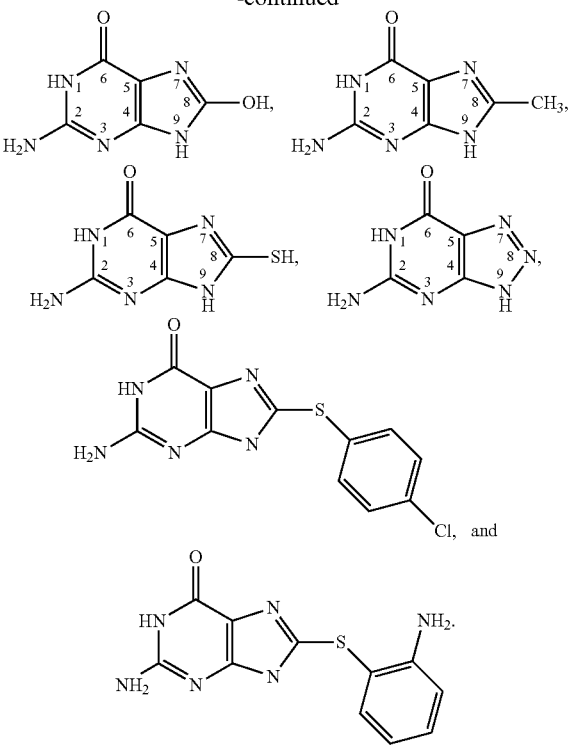

19. The method of claim 1, wherein said pain is acute pain.
20. The method of claim 1, wherein said pain is chronic pain.
21. The method of claim 1, wherein said pain is selected from the group consisting of peripheral and central neuropathic pain, inflammatory pain, functional pain, nociceptive pain, and headache.
22. The method of claim 21, wherein said pain is neuropathic pain.
23. The method of claim 21, wherein said pain is inflammatory pain.
24. The method of claim 1, wherein said pain is a caused by peripheral nerve damage or a peripheral nerve lesion.
25. A method of treating or reducing pain in a mammal in need thereof, said method comprising administering to said mammal a composition comprising a compound having the formula:

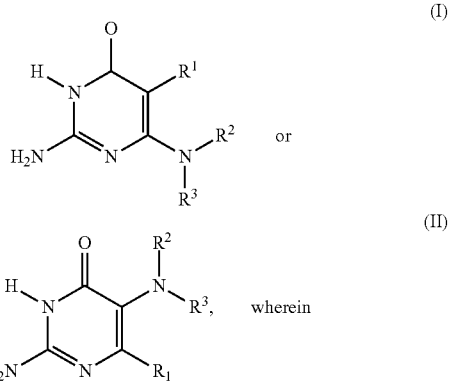

$R^1$ is H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$, wherein each of $R^4$ and $R^5$ is, independently, H, $C_{1-6}$ alkyl, $C_{6-12}$ aryl, heteroaryl, $C_{1-4}$ alkaryl, or $C_{1-4}$ alkheteroaryl, $R^2$ is H, $C_{1-6}$ alkyl, $C_{6-12}$ aryl, heteroaryl, $C_{1-4}$ alkaryl, or $C_{1-4}$ alkheteroaryl, and $R^3$ is H, $C_{1-6}$ alkyl, $C_{6-12}$ aryl, $C_{1-4}$ alkaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl and each of $R^7$ and $R^8$ is, independently, H, $C_{1-6}$ alkyl, $C_{6-12}$ aryl, heteroaryl, $C_{1-4}$ alkaryl, or $C_{1-4}$ alkheteroaryl; or $R^3$ is as above and $R^1$ and $R^2$ together are represented by

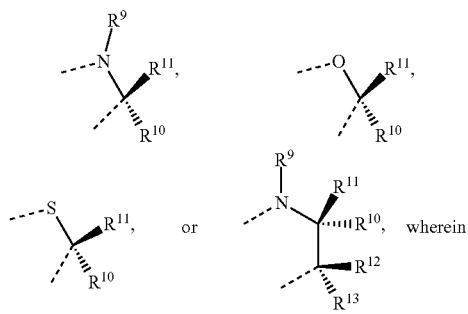

the N, O, or S of the $R^1/R^2$ linkage forms a bond to the pyrimidinone ring and each of $R^9$, $R^{10}$, $R^{11}$, $R^{12}$ and $R^{13}$ is, independently, H, $C_{1-6}$ alkyl, $C_{6-12}$ aryl, heteroaryl, $C_{1-4}$ alkaryl, or $C_{1-4}$ alkheteroaryl; or $R^3$ is as above and $R^1$ and $R^2$ together are represented by

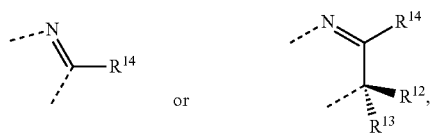

wherein the N of the $R^1/R^2$ linkage forms a bond to the pyrimidinone ring, each of $R^{12}$ and $R^{13}$ is as above, and $R^{14}$ is H, SH, $OR^4$, halo, $NO_2$, CN, $CO_2R^7$, $CONR^7R^8$, $SO_2R^7$, $SO_2NR^7R^8$,

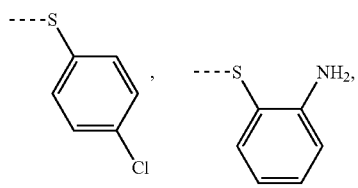

$C_{1-6}$ alkyl, $C_{6-12}$ aryl, heteroaryl, $C_{1-4}$ alkaryl, or $C_{1-4}$ alkheteroaryl, wherein each of $R^4$, $R^7$ and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl; or $R^1$ and $R^2$ together are represented by

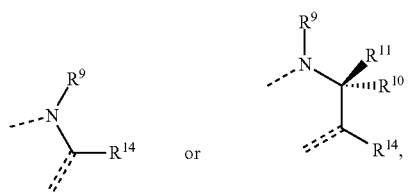

wherein the N of the $R^1/R^2$ linkage forms a bond to the pyrimidinone ring, each of $R^9$, $R^{10}$, $R^{11}$, and $R^{14}$ are as above, $R^3$ does not exist, and a double bond is formed between the carbon bearing $R^{14}$ and the nitrogen bearing $R^2$, in an amount sufficient to treat or reduce pain.

26. The method of claim 25, wherein said composition comprises a compound of formula (I), wherein $R^1$ is H, $C_{1-6}$ alkyl, halo, $NO_2$, CN, $CO_2R^4$, $CONR^4R^5$, $SO_2R^4$, $SO_2NR^4R^5$, $OR^4$, or $NR^4R^5$, wherein each of $R^4$ and $R^5$ is, independently, H, $C_{1-6}$ alkyl, $C_{6-12}$ aryl, heteroaryl, $C_{1-4}$ alkaryl, or $C_{1-4}$ alkheteroaryl, $R^2$ is H, $C_{1-6}$ alkyl, $C_{6-12}$ aryl, heteroaryl, $C_{1-4}$ alkaryl, or $C_{1-4}$ alkheteroaryl, and $R^3$ is H, $C_{1-6}$ alkyl, $C_{6-12}$ aryl, $C_{1-4}$ alkaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl and each of $R^7$ and $R^8$ is, independently, H, $C_{1-6}$ alkyl, $C_{6-12}$ aryl, heteroaryl, $C_{1-4}$ alkaryl, or $C_{1-4}$ alkheteroaryl.

27. The method of claim 25, wherein said composition comprises a compound of formula:

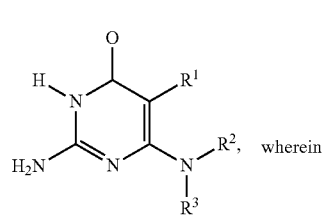

(I)

$R^1$ and $R^2$ together are represented by

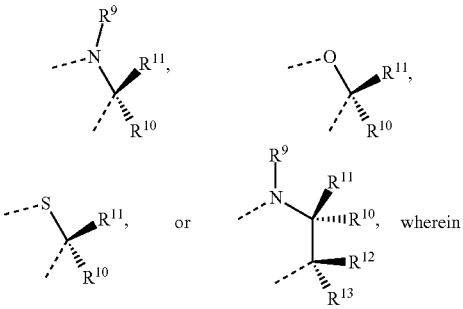

the N, O, or S of the $R^1/R^2$ linkage forms a bond to the pyrimidinone ring and each of $R^9$, $R^{10}$, $R^{11}$, $R^{12}$, and $R^{13}$ is, independently, H, $C_{1-6}$ alkyl, $C_{6-12}$ aryl, heteroaryl, $C_{1-4}$ alkaryl, or $C_{1-4}$ alkheteroaryl, and $R^3$ is H, $C_{1-6}$ alkyl, $C_{6-12}$ aryl, $C_{1-4}$ alkaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl and each of $R^7$ and $R^8$ is, independently, H, $C_{1-6}$ alkyl, $C_{6-12}$ aryl, heteroaryl, $C_{1-4}$ alkaryl, or $C_{1-4}$ alkheteroaryl.

28. The method of claim 25, wherein said composition comprises a compound of formula:

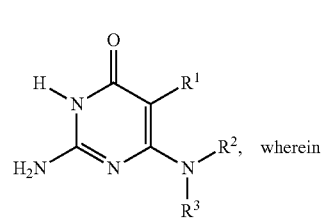

(I)

$R^1$ and $R^2$ together are represented by

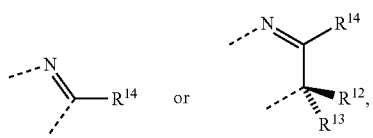

wherein the N of the $R^1/R^2$ linkage forms a bond to the pyrimidinone ring, $R^3$ is H, $C_{1-6}$ alkyl, $C_{6-12}$ aryl, $C_{1-4}$ alkaryl, $CO_2R^6$, $CONR^7R^8$, $SO_2R^6$, or $SO_2NR^7R^8$, wherein $R^6$ is $C_{1-6}$ alkyl, $C_{6-12}$ aryl, heteroaryl, $C_{1-4}$ alkaryl, or $C_{1-4}$ alkheteroaryl, each of $R^{12}$ and $R^{13}$ is, independently, H, $C_{1-6}$ alkyl, $C_{6-12}$ aryl, heteroaryl, $C_{1-4}$ alkaryl, or $C_{1-4}$ alkheteroaryl, $R^{14}$ is H, SH, $OR^4$, halo, $NO_2$, CN, $CO_2R^7$, $CONR^7R^8$, $SO_2R^7$, $SO_2NR^7R^8$,

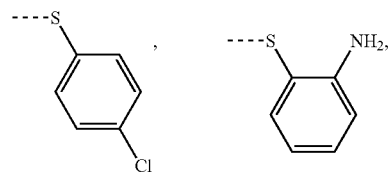

$C_{1-6}$ alkyl, $C_{6-12}$ aryl, heteroaryl, $C_{1-4}$ alkaryl, or $C_{1-4}$ alkheteroaryl, wherein each of $R^4$, $R^7$, and $R^8$ is, independently, H, $C_{1-6}$ alkyl, $C_{6-12}$ aryl, $C_{1-4}$ alkaryl, heteroaryl, or $C_{1-4}$ alkheteroaryl, $R^3$ does not exist, and a double bond is formed between the carbon bearing $R^{14}$ and the nitrogen bearing $R^2$.

30. The method of claim 1, wherein said composition comprises a compound of formula:

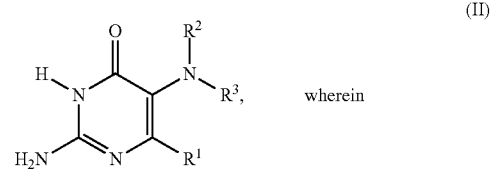

(II)

wherein $R^1$ and $R^2$ together are represented by

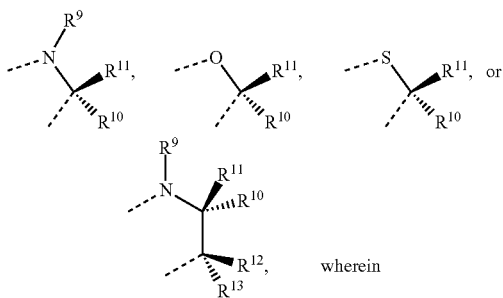

the N, O, or S of the $R^1/R^2$ linkage forms a bond to the pyrimidinone ring and each of $R^9$, $R^{10}$, $R^{11}$, $R^{12}$, and $R^{13}$ is, independently, H, $C_{1-6}$ alkyl, $C_{6-12}$ aryl, heteroaryl, $C_{1-4}$ alkaryl, or $C_{1-4}$ alkheteroaryl.

31. The method of claim 25, wherein said composition comprises a compound of formula:

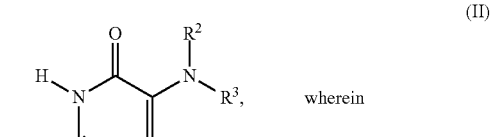

(II)

wherein $R^3$ is as above and $R^1$ and $R^2$ together are represented by

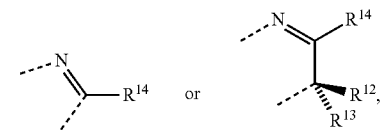

wherein the N of the $R^1/R^2$ linkage forms a bond to the pyrimidinone ring, $C_{1-6}$ alkyl, $C_{6-12}$ aryl, heteroaryl, $C_{1-4}$ alkaryl, or $C_{1-4}$ alkheteroaryl, wherein each of $R^4$, $R^7$, and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl.

29. The method of claim 25, wherein said composition comprises a compound of formula:

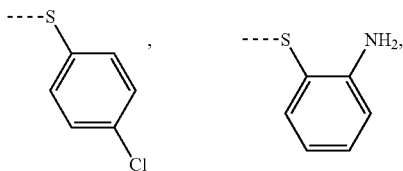

(I)

$R^1$ and $R^2$ together are represented by

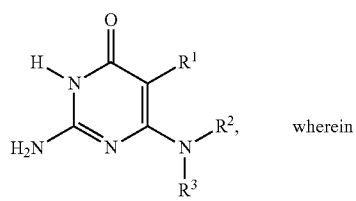

wherein the N of the $R^1/R^2$ linkage forms a bond to the pyrimidinone ring, each of $R^9$, $R^{10}$, and $R^{11}$ is, independently, H, $C_{1-6}$ alkyl, $C_{6-12}$ aryl, heteroaryl, $C_{1-4}$ alkaryl, or $C_{1-4}$ alkheteroaryl, $R^{14}$ is H, SH, $OR^4$, halo, $NO_2$, CN, $CO_2R^7$, $CONR^7R^8$, $SO_2R^7$, $SO_2NR^7R^8$,

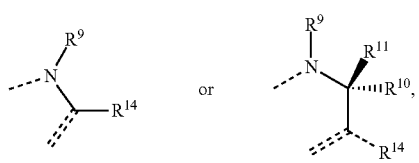

each of $R^{12}$ and $R^{13}$ is, independently, H, $C_{1-6}$ alkyl, $C_{6-12}$ aryl, heteroaryl, $C_{1-4}$ alkaryl, or $C_{1-4}$ alkheteroaryl, and
$R^{14}$ is H, SH, $OR^4$, halo, $NO_2$, CN, $CO_2R^7$, $CONR^7R^8$, $SO_2R^7$, $SO_2NR^7R^8$,

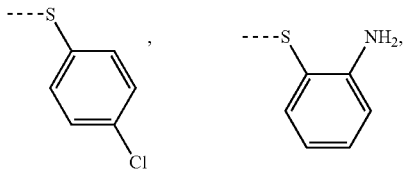

$C_{1-6}$ alkyl, $C_{6-12}$ aryl, heteroaryl, $C_{1-4}$ alkaryl, or $C_{1-4}$ alkheteroaryl, wherein each of $R^4$, $R^7$ and $R^8$ is, independently, H, $C_1$-$C_6$ alkyl, $C_6$-$C_{12}$ aryl, $C_1$-$C_4$ alkaryl, heteroaryl, or $C_1$-$C_4$ alkheteroaryl.

32. The method of claim 25, wherein said composition comprises a compound of formula:

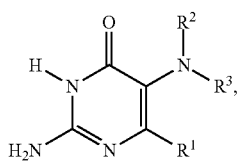

(II)

wherein $R^1$ and $R^2$ together are represented by

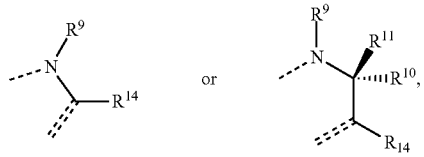

wherein the N of the $R^1/R^2$ linkage forms a bond to the pyrimidinone ring,
each of $R^9$, $R^{10}$, and $R^{11}$ is, independently, H, $C_{1-6}$ alkyl, $C_{6-12}$ aryl, heteroaryl, $C_{1-4}$ alkaryl, or $C_{1-4}$ alkheteroaryl, and
$R^{14}$ is H, SH, $OR^4$, halo, $NO_2$, CN, $CO_2R^7$, $CONR^7R^8$, $SO_2R^7$, $SO_2NR^7R^8$,

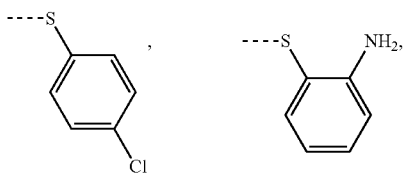

$C_{1-6}$ alkyl, $C_{6-12}$ aryl, heteroaryl, $C_{1-4}$ alkaryl, or $C_{1-4}$ alkheteroaryl, wherein each of $R^4$, $R^7$ and $R^8$ is, independently, H, $C_{1-6}$ alkyl, $C_{6-12}$ aryl, $C_{1-4}$ alkaryl, heteroaryl, or $C_{1-4}$ alkheteroaryl,
$R^3$ does not exist, and a double bond is formed between the carbon bearing $R^{14}$ and the nitrogen bearing $R^2$.

33. The method of claim 26, wherein said composition comprises a compound selected from the group consisting of

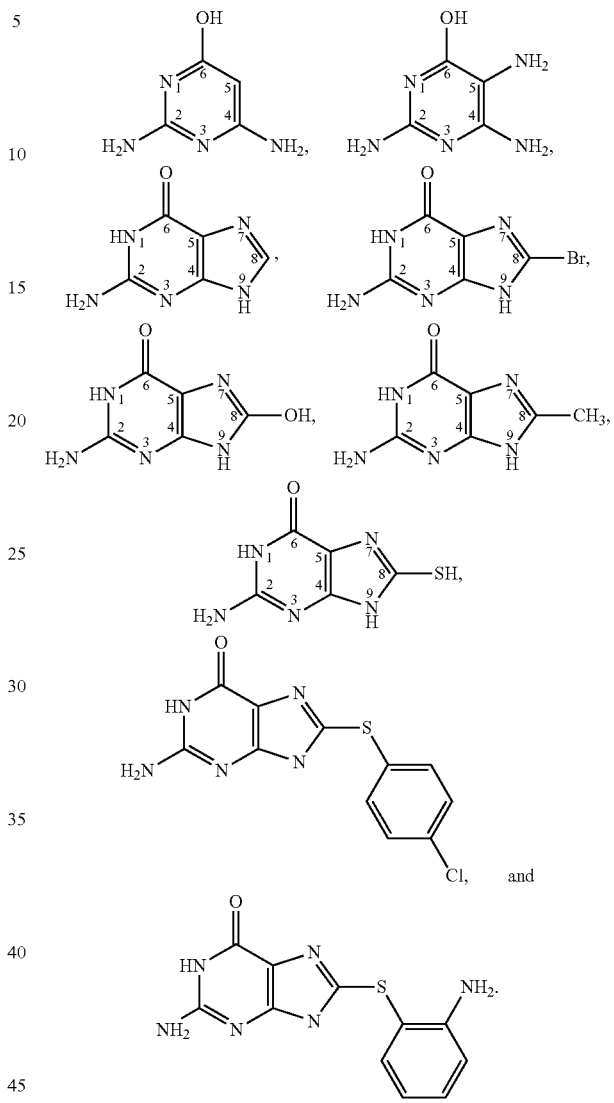

34. The method of claim 25, wherein said pain is acute pain.

35. The method of claim 25, wherein said pain is chronic pain.

36. The method of claim 25, wherein said pain is selected from the group consisting of peripheral and central neuropathic pain, inflammatory pain, functional pain, nociceptive pain, and headache.

37. The method of claim 36, wherein said pain is neuropathic pain.

38. The method of claim 36, wherein said pain is inflammatory pain.

39. The method of claim 25, wherein said pain is a caused by peripheral nerve damage or a peripheral nerve lesion.

* * * * *

UNITED STATES PATENT AND TRADEMARK OFFICE
CERTIFICATE OF CORRECTION

PATENT NO. : 7,906,520 B2
APPLICATION NO. : 10/987289
DATED : March 15, 2011
INVENTOR(S) : Woolf et al.

It is certified that error appears in the above-identified patent and that said Letters Patent is hereby corrected as shown below:

Page 2, under OTHER PUBLICATIONS, in Minami et al., replace "Postaglandin $E_2$" with --Prostaglandin $E_2$--.

Column 3, Line 57, replace "$R^1$ is" with --such that $R^1$ is--.

Column 4, Line 18, replace "the N, O, or S" with --where the N, O, or S--.

Column 5, Lines 15-32, replace " 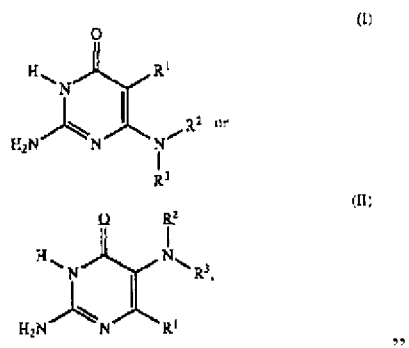 "

with -- 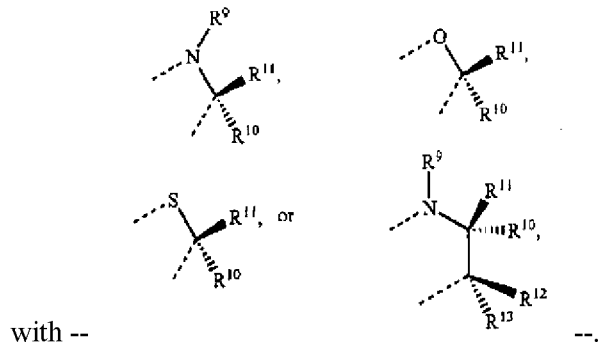 --.

Signed and Sealed this
Tenth Day of July, 2012

David J. Kappos
*Director of the United States Patent and Trademark Office*

Column 10, Line 40, replace "toxic a peripheral" with --toxic peripheral--.

Column 17, Line 49, replace "hydormorphone" with --hydromorphone--.

Column 28, Line 2, replace "10: 981-878" with --10: 871-878--.

Column 30, Line 28, replace "where R is a" with --where $R^6$ is a--.

Column 31, Lines 43-51, replace " 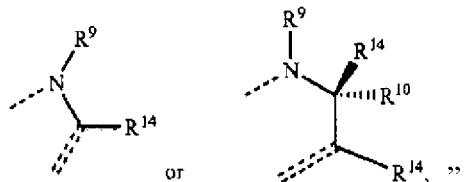 with -- 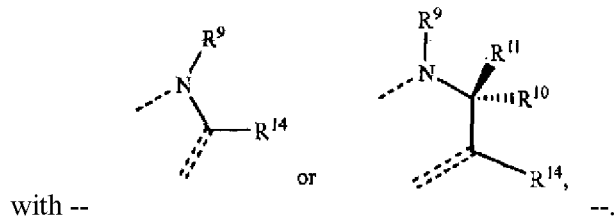 --.

Column 33, Lines 2-11, replace " 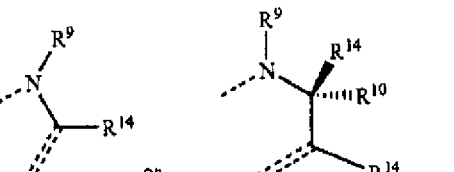 with -- 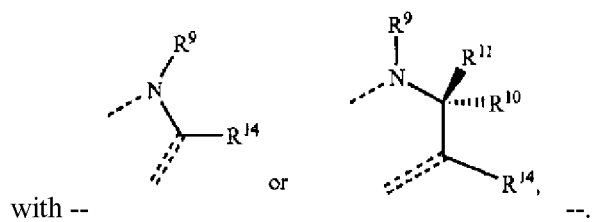 --.

Column 34, Line 28, replace "BH4.2HCl" with --BH4·2HCl--.

Column 35, Line 58, replace "hydromoiphone" with --hydromorphone--.

Column 57, Line 58, replace "polvoxyethylene" with --polyoxyethylene--.

CERTIFICATE OF CORRECTION (continued)
U.S. Pat. No. 7,906,520 B2

Column 63, Claim 17, Line 19, replace " 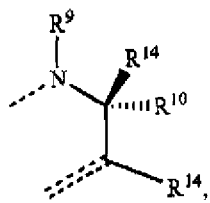 " with 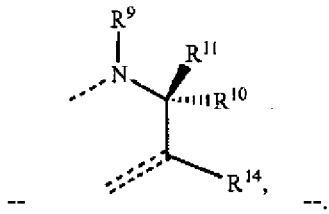 --.

Column 64, Claim 18, Line 10, remove " 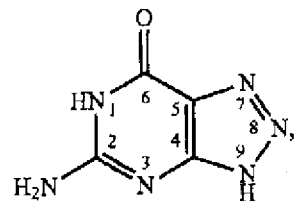 ".

UNITED STATES PATENT AND TRADEMARK OFFICE
CERTIFICATE OF CORRECTION

| | |
|---|---|
| PATENT NO. | : 7,906,520 B2 |
| APPLICATION NO. | : 10/987289 |
| DATED | : March 15, 2011 |
| INVENTOR(S) | : Clifford J. Woolf et al. |

It is certified that error appears in the above-identified patent and that said Letters Patent is hereby corrected as shown below:

In the Specification

Column 1, Line 3, insert:
-- STATEMENT AS TO FEDERALLY FUNDED RESEARCH
This invention was made with government support under NS038253 awarded by the National Institutes of Health. The government has certain rights in the invention. --

Signed and Sealed this
Second Day of May, 2023

*Katherine Kelly Vidal*

Katherine Kelly Vidal
*Director of the United States Patent and Trademark Office*